United States Patent
Hedrick et al.

(10) Patent No.: US 9,637,592 B2
(45) Date of Patent: May 2, 2017

(54) VITAMIN FUNCTIONALIZED GEL-FORMING BLOCK COPOLYMERS FOR BIOMEDICAL APPLICATIONS

(71) Applicants: International Business Machines Corporation, Armonk, NY (US); Agency For Science, Technology and Research, Singapore (SG)

(72) Inventors: James L. Hedrick, Pleasanton, CA (US); Ashlynn L. Z. Lee, Singapore (SG); Victor W. L. Ng, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 0 days.

(21) Appl. No.: 15/343,537

(22) Filed: Nov. 4, 2016

(65) Prior Publication Data
US 2017/0051105 A1 Feb. 23, 2017

Related U.S. Application Data

(62) Division of application No. 14/697,878, filed on Apr. 28, 2015, now Pat. No. 9,511,146, which is a division of application No. 13/859,062, filed on Apr. 9, 2013, now Pat. No. 9,040,034.

(51) Int. Cl.
*A61K 47/34* (2006.01)
*C08G 64/18* (2006.01)
*A61K 47/48* (2006.01)

(52) U.S. Cl.
CPC ...... *C08G 64/183* (2013.01); *A61K 47/48215* (2013.01); *C08G 2210/00* (2013.01)

(58) Field of Classification Search
None
See application file for complete search history.

(56) References Cited

U.S. PATENT DOCUMENTS

| | | | |
|---|---|---|---|
| 5,235,073 A | 8/1993 | Kim et al. | |
| 5,441,725 A | 8/1995 | Kim et al. | |
| 6,294,192 B1 | 9/2001 | Patel et al. | |
| 8,192,722 B2 | 6/2012 | Arkenau-Maric et al. | |
| 8,241,664 B2 | 8/2012 | Dudley et al. | |
| 8,633,296 B1 | 1/2014 | Coady et al. | |
| 2003/0049320 A1 | 3/2003 | Bhagwatwar et al. | |
| 2004/0258754 A1 | 12/2004 | Alakhov et al. | |
| 2006/0034923 A1 | 2/2006 | Li et al. | |
| 2006/0286143 A1 | 12/2006 | Shalaby et al. | |
| 2007/0196416 A1 | 8/2007 | Li et al. | |
| 2007/0218099 A1 | 9/2007 | Kim et al. | |
| 2008/0166382 A1 | 7/2008 | Hsieh et al. | |
| 2009/0214419 A1 | 8/2009 | Therien et al. | |
| 2009/0297609 A1 | 12/2009 | Shoichet et al. | |
| 2010/0055068 A1 | 3/2010 | Santerre et al. | |
| 2010/0137206 A1* | 6/2010 | Lavasanifar | A61K 9/1075 514/1.1 |
| 2011/0054064 A1 | 3/2011 | Fukushima et al. | |
| 2012/0231060 A1 | 9/2012 | Coady et al. | |
| 2012/0232018 A1 | 9/2012 | Hedrick et al. | |
| 2012/0270822 A1 | 10/2012 | Wasan et al. | |
| 2013/0017249 A1* | 1/2013 | Niitsu | A61K 47/48107 424/450 |

FOREIGN PATENT DOCUMENTS

| | | |
|---|---|---|
| CN | 102670509 A | 9/2010 |
| JP | 2002541216 A | 4/1999 |
| KR | 1019950007044 B1 | 6/1995 |
| WO | 2011078804 A1 | 6/2011 |

OTHER PUBLICATIONS

Fujiwara, et al., "Novel Thermo-Responsive Formation of a Hydrogel by Stereo-Complexation between PLLA-PEG-PLLA and PDLA-PEG-PDLA Block Copolymers," Macromol. Biosci. 2001, 1, 204-208.
Li, et al., "Synthesis and Characterization of Amphiphilic Lipopolymers for Micellar Drug Delivery", Biomacromolecules, 2010, 11, pp. 2510-2620, Abstract.
Prasad, et al., "alpha-Tocopheryl Succinate, the Most Effective Form of Vitamin E for Adjuvant Cancer Treatment: A Review," Journal of the American College of Nutrition, vol. 22, No. 2, 108-117 (2003).
Pratt, et al., "Exploration, Optimization, and Application of Supramolecular Thiourea-Amine Catalysts for the Synthesis of Lactide (Co)polymers," Macromolecules 2006, 39, 7863-7871; Published on Web Oct. 18, 2006.
Pratt, et al., "Tagging alcohols with cyclic carbonate: a versatile equivalent of (meth)acrylate for ring opening polymerization," Chem.Commun., 2008, 114-116; publishe Oct. 25, 2007.
Qiao, et al., "Highly dynamic biodegradable micelles capable of lysing Gram-positive and Gram-negative bacterial membrane", Biomaterials 33 (2012) 1146-1153; Available online Nov. 5, 2011.
Spasic, M. B., "Molecular pathways in induction of cancer cell apoptosis by Vitamin E analogues," Arch Oncol 2007, 15(3-4), p. 63.

(Continued)

Primary Examiner — Brian Gulledge
(74) Attorney, Agent, or Firm — Michael R. Roberts

(57) ABSTRACT

Gel-forming block copolymers were prepared comprising i) a central hydrophilic block consisting essentially of a divalent poly(ethylene oxide) chain and ii) two peripheral monocarbonate or polycarbonate hydrophobic blocks. The hydrophobic blocks comprise one or more vitamin-bearing subunits. The vitamin-bearing subunits comprise a carbonate backbone portion and a side chain comprising a covalently bound form of a vitamin. The gel-forming block copolymers can be used to prepare various biodegradable and/or biocompatible hydrogel and organogel drug compositions, in particular antimicrobial and/or anti-tumor drug compositions. The hydrogel compositions can be suitable for depot injections. Synergistic enhancement of toxicity to microbes was observed with compositions comprising an antimicrobial cationic polymer and an antimicrobial compound.

20 Claims, 27 Drawing Sheets

(56) References Cited

OTHER PUBLICATIONS

USPTO, International Search Report, mailed Aug. 21, 2014, PCT application PCT/US2014/032314, filing date Mar. 31, 2014.
USPTO, Written Opinion, mailed Aug. 21, 2014, PCT application PCT/US2014/032314, filing date Mar. 31, 2014.
Van Vlerken, et al., "Poly(ethylene glycol)-modified Nanocarriers for Tumor-targeted and Intracellular Delivery," Pharm Res. Aug. 2007;24(8):1405-14. Epub Mar. 29, 2007.
Zhang, et al.,"Vitamin E TPGS as a molecular biomaterial for drug delivery," Biomaterials 33 (2012) 4889-4906; Available online Apr. 11, 2012.

* cited by examiner

|  | Heart | Lung | Liver | Kidney |
|---|---|---|---|---|
| Ctrl | 100 μm | 100 μm | 100 μm | 100 μm |
| Her Sol (I.V., weekly) | 100 μm | 100 μm | 100 μm | 100 μm |
| Her Sol (S.C., weekly) | 100 μm | 100 μm | 100 μm | 100 μm |
| Her Gel (S.C., one-time) | 100 μm | 100 μm | 100 μm | 100 μm |

FIG. 16

VITAMIN FUNCTIONALIZED GEL-FORMING BLOCK COPOLYMERS FOR BIOMEDICAL APPLICATIONS

PARTIES TO A JOINT RESEARCH AGREEMENT

This invention was made under a joint research agreement between International Business Machines Corporation and the Agency For Science, Technology and Research.

BACKGROUND

Hydrogels and organogels produced from the self-assembly of synthetic polymers have an inexhaustible potential to serve as a delivery matrix for a vast range of pharmaceutical, cosmetic and dietary products. Recent developments in polymer chemistry have enabled polymers to be synthesized with well-controlled composition and architecture. Highly versatile orthogonal functionalization strategies also allow gelation of such polymers and containment of drug payload through one or a combination of the following association mechanisms: hydrophobic interactions, ionic interactions, hydrogen bonding, physical entanglement of macromolecules and chemical crosslinking of the matrix.

A number of physical gel systems have been formulated using the 'ABA'-type triblock copolymers, and the polymeric amphiphiles can be designed with either the 'A' or 'B' constituent blocks to be hydrophilic or hydrophobic. Many of such systems engage the use of poly(ethylene glycol) (PEG) as the uncharged hydrophilic constituent block for its biocompatibility and non-toxicity. As for hydrophobic portion(s), some of commonly selected blocks are poly(L-lactide) (PLLA), poly(D-lactide) (PDLA), poly(glycolide) (PGA), and poly(caprolactone) (PCL), which can be prepared either as the middle 'B' block (e.g., PEG-b-PGA-b-PEG) or as the terminus 'A' blocks (e.g., PLLA-b-PEG-b-PLLA). Aqueous mixture of enantiomeric triblock copolymers of the PLLA and PDLA-containing polymers could also give rise to physical gels formed via stereocomplexation.

Polymeric gel systems can be broadly classified as organogels or hydrogels, depending on the dispersion media used. Organogels have an organic liquid phase that is immobilized by a 3D physically crosslinked network of intertwined fibers of self-assembled polymer chains. Various kinds of organic material can be used to make up the liquid phase (e.g., organic solvents, mineral oil, plant oil, and combinations of the foregoing). Organogels are mainly used for cosmetics/dietary applications while relatively much fewer organogels are being evaluated as drug/vaccine delivery matrices. This is primarily due to the scarce amount of information available regarding the toxicology and biocompatibility of the gel-forming polymers and their degraded products. Nevertheless, when toxicity concerns are circumvented, organogels have potential for use as topical formulations owing to the enhanced dermal permeation capacities of typical organogels. Alternative modes of application include oral and trans-mucosal as well as subcutaneous depot injections. Herein, a depot is a body area in which a substance (e.g., a drug) can be accumulated, deposited, or stored and from which it can be distributed. A depot injection is an injection of a substance in a form that tends to keep it at or near the site of injection so that absorption occurs over a prolonged period.

Hydrogels, which are prepared in water, are more widely-studied compared to organogel systems. Most of the commonly used hydrogel-forming 'ABA'-type triblock copolymers (e.g., PLLA-b-PEG-b-PLLA and PCL-b-PEG-b-PCL) require high polymer concentration and hydrophobic content for hydrogel formation. For instance, (PLLA-b-PEG-b-PLLA) containing lactide content of 17 wt. % to 37 wt. % requires a minimum concentration of about 16 wt. % of the triblock copolymer for gelation. Such a high proportion of hydrophobic constituents could give rise to adverse physiological effects during in vivo degradation. Thus, it is desirable to develop polymeric materials that can form hydrogels at a low concentration.

According to a 2008 World Health Organization (WHO) survey, breast cancer comprises of 22.9% of all cancers (excluding non-melanoma skin cancer) and its mortality rate is around 13.7% worldwide. In Europe, the incident rate of breast cancer is even higher, reaching 28%. Treatment of breast cancer may vary according to the size, stage and rate of growth, as well as the type of tumor. There are currently three main categories of adjuvant, or post-surgery, therapy. These include hormone-blocking therapy, chemotherapy and monoclonal antibodies (mAbs) therapy. The latter involves the utilization of mAbs to target specific cells or proteins towards the treatment of disease by inducing, enhancing, or suppressing an immune response. It can be used in conjunction with either hormone-blocking therapy or chemotherapy to enhance the efficacy of cancer treatment.

Studies have shown that the human epidermal growth factor receptor 2 (HER2) genes are amplified and/or over-expressed in 20% to 25% of invasive breast cancers. These HER2-positive breast cancers have significantly lower survival rates compared to HER2-negative breast tumors. The HER2-positive breast tumors are most likely to show unrestrained growth and division of cells, thus increasing the incidence of cancer development. Herceptin is a recombinant humanized mAb that can selectively bind to HER2 proteins, thereby regulating the otherwise uncontrollable cancer cell growth. It is also a US Food and Drug Administration (FDA)-approved therapeutic for the treatment of HER2-positive breast cancer. Intravenous administration is the current mode of herceptin delivery in most clinics. However, many controversies surround the optimal mode of delivery in terms of duration and dosage. Recently, F Hoffmann-La Roche reported a phase 3 clinical trial (HannaH study) involving the subcutaneous (versus intravenous) administration of (neo)adjuvant herceptin in patients with HER2-positive breast cancer. The formulation contained a fixed dose of herceptin and recombinant human hyaluronidase (rHuPH-20), a class of enzymes that temporarily degrades interstitial hyaluronan in the subcutaneous space, as an excipient. The study found that therapeutic efficacy of subcutaneous delivery of herceptin was comparable to the traditional intravenous route but the therapy had the advantage of improved patient convenience, better compliance, reduced pharmacy preparation times, and optimization of medical resources.

The foregoing illustrates that an ongoing need exists for more efficacious drug and antibiotic formulations. More specifically, formulations are needed for improved efficacy of subcutaneous treatments used in cancer therapy.

SUMMARY

Accordingly, a drug composition is disclosed, comprising:
about 4 wt. % to about 10 wt. % of a gel-forming block copolymer;
a solvent; and about 0.0001 wt. % to about 10 wt. % of a drug;
wherein
the gel-forming block copolymer has a structure in accordance with formula (1):

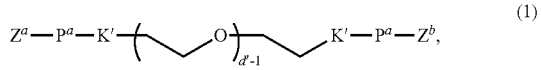
(1)

wherein
d' is a positive number having a value of about 100 to about 600,
each K' is an independent divalent linking group selected from the group consisting of O, NH, S, and combinations thereof,
each $P^a$ is an independent monocarbonate or polycarbonate chain comprising 1 to about 10 vitamin-bearing subunits, wherein each of the vitamin-bearing subunits comprises a carbonate backbone portion and a side chain linked to the carbonate backbone portion, the side chain comprising a covalently bound form of a vitamin,
$Z^a$ is a first end group selected from the group consisting of hydrogen and groups comprising 1 to about 15 carbons, and
$Z^b$ is a second end group selected from the group consisting of hydrogen and groups comprising 1 to about 15 carbons;
and wherein
weight percent (wt. %) is based on total weight of the drug composition,
the drug composition is a gel formed by noncovalent interactions of polymer chains of the block copolymer in the solvent, and
the drug is contained in the gel.

Also disclosed is an antimicrobial drug composition, comprising:
about 4 wt. % to about 10 wt. % of a gel-forming block copolymer;
a solvent; and
about 0.0001 wt. % to about 10 wt. % of an antimicrobial cationic polycarbonate (first drug);
wherein
the gel-forming block copolymer has a structure in accordance with formula (1):

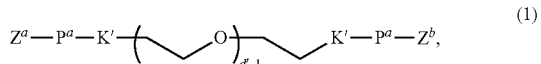
(1)

wherein
d' is a positive number having a value of about 100 to about 600,
each K' is an independent divalent linking group selected from the group consisting of O, NH, S, and combinations thereof,
each $P^a$ is an independent monocarbonate or polycarbonate chain comprising 1 to about 10 vitamin-bearing subunits, wherein each of the vitamin-bearing subunits comprises a carbonate backbone portion and a side chain linked to the carbonate backbone portion, the side chain comprising a covalently bound form of a vitamin,
$Z^a$ is a first end group selected from the group consisting of hydrogen and groups comprising 1 to about 15 carbons, and
$Z^b$ is a second end group selected from the group consisting of hydrogen and groups comprising 1 to about 15 carbons;
and wherein
weight percent (wt. %) is based on total weight of the antimicrobial drug composition, the antimicrobial drug composition is a gel formed by noncovalent interactions of polymer chains of the gel-forming block copolymer in the solvent,
the antimicrobial cationic polycarbonate is contained in the gel.

Further disclosed is an aqueous solution for killing a microbe, comprising:
about 0.0001 wt. % to about 10 wt. % of an antimicrobial cationic polycarbonate (first drug); and
about 0.0001 wt. % to about 10 wt. % of an antimicrobial compound (second drug);
wherein
weight percent (wt. %) is based on total weight of the aqueous solution,
the first drug and the second drug are associated by noncovalent interactions in the aqueous solution.

Also disclosed is a gel-forming block copolymer having a structure in accordance with formula (1):

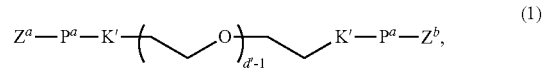
(1)

wherein
d' is a positive number having a value of about 100 to about 600,
each K' is an independent divalent linking group selected from the group consisting of O, NH, S, and combinations thereof,
each $P^a$ is an independent monocarbonate or polycarbonate chain comprising 1 to about 10 vitamin-bearing subunits, wherein each of the vitamin-bearing subunits comprises a carbonate backbone portion and a side chain linked to the carbonate backbone portion, the side chain comprising a covalently bound form of a vitamin,
$Z^a$ is a first end group selected from the group consisting of hydrogen and groups comprising 1 to about 15 carbons, and
$Z^b$ is a second end group selected from the group consisting of hydrogen and groups comprising 1 to about 15 carbons.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 16 is a series of photomicrographs of mice heart, lung, liver and kidney cells after H&E staining at 28 days post injection of herceptin solution formulations (intravenous and subcutaneous) performed on a weekly basis and herceptin loaded hydrogel (Example 24) injected subcutaneously once on the first day of treatment, as described above for FIG. 15. The scale bar represents 100 micrometers.

FIG. 26 shows the drug combination is effective at extremely low doxycycline concentration.

DETAILED DESCRIPTION

Figure 1A:
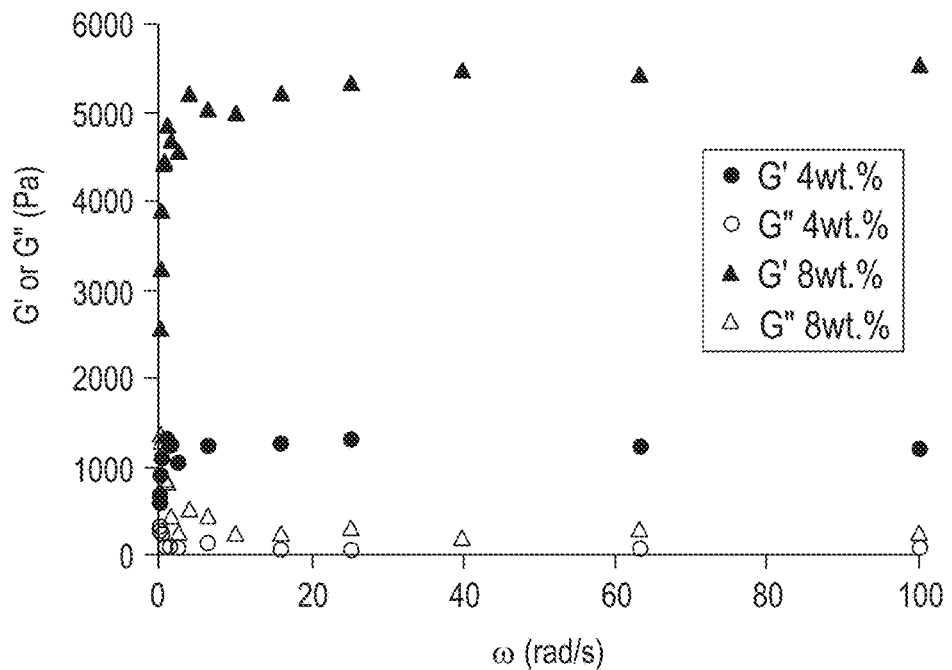
FIG. 1A is a graph showing the storage (G') and loss (G") moduli of blank hydrogels containing 4 wt. % and 8 wt. % VitE1.25-PEG(20k)-VitE1.25 in HPLC water (Example 15 and Example 16, respectively). Herein, weight percent (wt. %) is based on total weight of the hydrogel unless otherwise indicated.

Gel-forming block copolymers are disclosed that comprise i) a central hydrophilic block, ii) two peripheral hydrophobic blocks linked to respective ends of the hydrophilic block, and iii) two end groups linked to respective ends of the hydrophobic blocks. The hydrophilic block consists essentially of a divalent poly(ethylene oxide) chain having a degree of polymerization (DP) of about 100 to about 600. Each of the hydrophobic blocks can be a monocarbonate or a polycarbonate comprising 1 to about 10 carbonate subunits, which comprise a covalently bound form of a vitamin. These carbonate subunits are referred herein as vitamin-bearing subunits. The vitamin-bearing subunits comprise a carbonate backbone and a side chain bearing the covalently bound form of a vitamin. The end groups are selected from the group consisting of hydrogen and $C_1$-$C_{15}$ groups.

The hydrophobic blocks can comprise an optional second carbonate subunit, which can act as a diluent for the vitamin-bearing subunits and/or provide additional functionality (e.g., charge-containing amine or carboxylic acid groups) for enhancing the payload-carrying capacity and/or bioactive properties of the gel-forming block copolymers. In a preferred embodiment, the gel-forming block copolymers are non-charged. In another embodiment, each of the hydrophobic blocks consists essentially of 1 to about 4 vitamin-bearing subunits, and each of the end groups is hydrogen.

The gel-forming block copolymers and the antimicrobial cationic polymers described further below can be biodegradable. The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

The gel-forming block copolymers and antimicrobial cationic polymers can be biocompatible. A "biocompatible" material is defined herein as a material capable of performing with an appropriate host response in a specific application.

The gel-forming block copolymers can form a gel in a solvent at a temperature of about 20° C. to about 40° C., at a gel-forming block copolymer concentration of about 4 wt. % or more, preferably about 4 wt. % to about 10 wt. %, based on total weight of the gel including solvent. Stiffness of the physical gels, represented by the storage modulus (G'), can vary from about 300 Pascals (Pa) to about 12,000

Pa by adjusting the gel-forming block copolymer structure and/or the concentration. The solvent can be water, an organic solvent, or a mixture thereof. Organic solvents include volatile organic liquids (e.g., ethanol) and organic liquids having little or no volatility (e.g., mineral oils, plant oils) at standard temperatures and pressures.

Herein, "gels" means "hydrogels and/or organogels" unless otherwise indicated. The gels are formed by noncovalent interactions of polymer chains of the gel-forming block copolymer in a given solvent. The gel network is composed of physical crosslinks of these polymer chains. The gels can serve as a matrix for delivering a variety of medically useful materials, including one or more drugs, which can be physically loaded into the gels. Herein, a "drug" can be any substance recognized or defined by the U.S. Food, Drug, and Cosmetic Act that can be effectively formulated with the disclosed gels and provide an effective therapeutic use. Drugs include substances used in the diagnosis, treatment, and/or prevention of a disease, and/or treatment of wounds. Drugs also include materials used in topically applied cosmetics products and cosmetic surgery products. Drugs also include dietary products such as vitamins. Drugs also include living cells if used for a therapeutic treatment. The drugs are preferably contained in the gel without being covalently bound to the gel-forming block copolymer. The drugs can be dissolved or dispersed in the gel matrix.

A drug can be a naturally produced or synthetic compound, a naturally produced or synthetic polymer, or combinations of the foregoing materials. Non-limiting exemplary naturally produced compounds include paclitaxel, artemisinin, alkaloids, terpenoids, phytosterols, natural phenols, ciclosporin, lovastatin, morphine, quinine, tubocurarine, nicotine, muscarine, asperlicin, eleutherobin, discodermolide, bryostatins, dolostatins, cephalostatins, and vitamins. Exemplary synthetic compounds include the antimicrobial drugs cephalosporins, tetracyclines, aminoglycosides, rifamycins, chloramphenicol, fluconazole and doxycycline. Exemplary naturally produced polymers include genes, nucleotides, proteins, and peptides. Exemplary synthetic polymers include antimicrobial cationic polycarbonates and monoclonal antibodies produced artificially by a genetic engineering technique.

Herein, a vitamin is defined as any of a group of organic compounds that are essential in small quantities for normal metabolism of a living body, and generally cannot be synthesized in the body. Exemplary vitamins include vitamin A (retinol), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12 (cobalamines), beta-carotene, vitamin C (ascorbic acid), vitamin D compounds (which include vitamin D1 (calciferol), vitamin D2 (ergocalciferol), and/or vitamin D3 (cholecalciferol)), vitamin E compounds (which include alpha-tocopherol, beta-tocopherol, gamma-tocopherol, delta-tocopherol, alpha-tocotrienol, beta-tocotrienol, gamma-tocotrienol, and/or delta-tocotrienol), and vitamin K1 (phylloquinone).

A loaded gel (also referred to as a drug composition) comprises a solvent, about 4 wt. % to about 10 wt. % of a gel-forming block copolymer, and about 0.0001 wt. % to about 10 wt. % of a drug, more specifically about 0.0001 wt. % to about 2 wt. % of the drug, and even more specifically about 0.0001 wt. % to about 1 wt. % of the drug. For example, a loaded gel can comprise an anti-tumor drug suitable for treating a cancer. As another example, a loaded gel can comprise an antimicrobial cationic polymer (a first drug). The antimicrobial cationic polymer can be a homopolymer, random copolymer, block copolymer, star polymer, star polymer having a crosslinked microgel core, dendritic polymer, or a combination of the foregoing polymer types. Preferably, the antimicrobial cationic polymer is one or more of the cationic polymers described further below, which are cationic polycarbonates. The antimicrobial cationic polycarbonate is preferably contained in the gel without being covalently bound to the gel-forming block copolymer. The loaded gel can further comprise an antimicrobial compound (a second drug) such as, for example, fluconazole, which is suitable for eradicating biofilms. The loaded gels can include one or more drugs, which are associated by noncovalent interactions in the gel. The loaded gels provide a means for controlling the release rate of a drug and localizing the drug in the vicinity of the application site or injection site, thereby increasing the efficacy of the drug.

The loaded gel compositions can be delivered by various types of injection, including intradermal, subcutaneous, intramuscular, intravenous, intraosseous, and/or intraperitoneal injection. The loaded gels can be applied topically to a skin surface (e.g., for transdermal delivery of biologically active substances), and/or to other body surfaces, including the eyes and body cavities. The loaded gels can also be applied to wounds.

The solvent for the loaded gel can be water and/or an organic solvent. A non-limiting example of a organic solvent is KOLLIPHOR RH40 (registered trademark of BASF). KOLLIPHOR RH40, also known as PEG-40 castor oil, is a non-ionic polyethoxylated detergent.

The gel-forming block copolymers have a structure in accordance with formula (1):

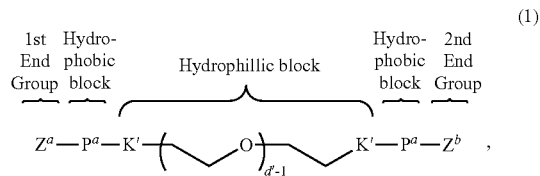

wherein d' is a positive number having a value of about 100 to about 600, each K' is an independent divalent linking group selected from the group consisting of O, NH, S, and combinations thereof, each $P^a$ is an independent monocarbonate or polycarbonate chain comprising 1 to about 10 vitamin-bearing subunits, wherein each of the vitamin-bearing subunits comprises a carbonate backbone portion and a side chain linked to the carbonate backbone portion, the side chain comprising a covalently bound form of a vitamin, $Z^a$ is a first end group selected from the group consisting of hydrogen and groups comprising 1 to about 15 carbons, and $Z^b$ is a second end group selected from the group consisting of hydrogen and groups comprising 1 to about 15 carbons.

Preferably the vitamin-bearing subunits are non-charged. In an embodiment, each $P^a$ consists essentially of 1 to about 10 vitamin-bearing subunits. In another embodiment, each K' is O.

The vitamin-bearing subunits of $P^a$ can have a structure in accordance with formula (2):

(2)

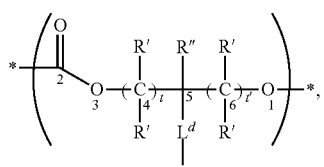

wherein
the carbonate backbone atoms are numbered 1 to 6,
$L^d$ is a single bond or a divalent linking group comprising 1 to about 15 carbons,
V' is a moiety comprising a covalently bound form of a vitamin,
each R' is an independent monovalent radical selected from the group consisting of hydrogen, halogens, methyl, and ethyl,
R" is a monovalent radical selected from the group consisting of hydrogen and alkyl groups comprising 1 to 6 carbons,
t is a positive integer having a value of 0 to 2,
t' is a positive integer having a value of 0 to 2, and
t and t' cannot both be zero.

Herein, a starred bond (*-) represents an attachment point to another portion of a chemical structure.

More specific vitamin-bearing subunits comprise a covalently bound form of a vitamin selected from the group consisting of vitamin D compounds, vitamin E compounds, and combinations thereof.

Still more specific vitamin-bearing subunits comprise a covalently bound form of a vitamin selected from the group consisting of alpha-tocopherol, beta-tocopherol, gamma-tocopherol, delta-tocopherol, alpha-tocotrienol, beta-tocotrienol, gamma-tocotrienol, delta-tocotrienol, and combinations thereof Even more specific vitamin-bearing subunits comprise a carbonate backbone portion and a side chain linked to the backbone portion, the side chain comprising a covalently bound form of alpha-tocopherol (a vitamin E compound):

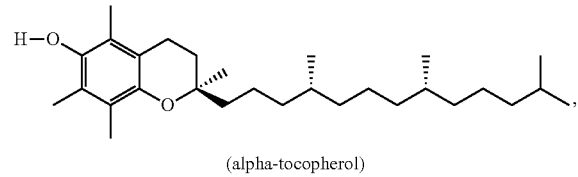 [SMILES: Cc1c(C)c2c(c(C)c1O)CC[C@@](C)(CCC[C@H](C)CCC[C@H](C)CCCC(C)C)O2]

(alpha-tocopherol)

a known antioxidant. The introduction of hydrophobic alpha-tocopherol moieties into the A block has a significant influence on the threshold concentration for gelation and the rheological properties of the hydrogels. Moreover, alpha-tocopherol and poly(ethylene glycol) (PEG) are biocompatible and FDA-approved chemical compounds, which gives the hydrogel system added advantage in the evaluation of its use in a pharmaceutical application.

The covalently bound form of the vitamin can be present as a single stereoisomer or as a mixture of stereoisomers.

$Z^a$ and $Z^b$ are independent end groups. In an embodiment, each of $Z^a$ and $Z^b$ is an acyl group (e.g., acetyl, benzoyl). In another embodiment, $Z^a$ is hydrogen and $Z^b$ is hydrogen.

A more specific vitamin-bearing subunit has a structure in accordance with formula (3):

(3)

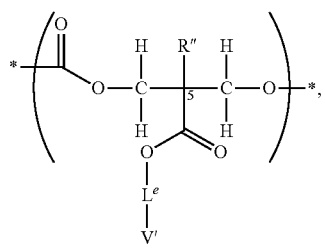

wherein
$L^e$ is a single bond or a divalent linking group comprising 1 to about 14 carbons,
V' is a moiety comprising a covalently bound form of a vitamin, and
R" is a monovalent radical selected from the group consisting of hydrogen and alkyl groups comprising 1 to 6 carbons.

In an embodiment, $L^e$ comprises 1 to about 10 carbons.

Another more specific vitamin-bearing subunit has a structure in accordance with formula (4):

(4)

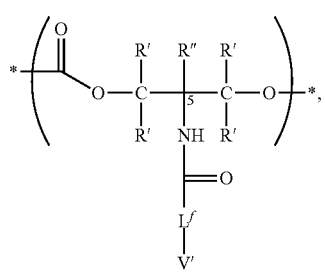

wherein
$L^f$ is a single bond or a divalent linking group comprising 1 to about 14 carbons,
V is a moiety comprising a covalently bound form of a vitamin,
each R' is an independent monovalent radical selected from the group consisting of hydrogen, halogens, methyl, and ethyl, and
R" is a monovalent radical selected from the group consisting of hydrogen and alkyl groups comprising 1 to 6 carbons.

In an embodiment, $L^f$ comprises 1 to about 10 carbons.

A more specific gel-forming block copolymer has a structure according to formula (1-A):

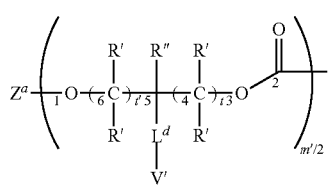
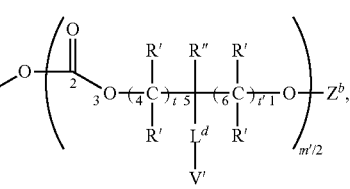

(1-A)

wherein the carbonate backbone atoms are numbered 1 to 6 in each carbonate subunit, d' is a positive number having a value of about 100 to about 600, each m' is an independent positive number having a value of 2 to about 20, each $L^d$ is independently a single bond or a divalent linking group comprising 1 to about 15 carbons, each V' is an independent moiety comprising a covalently bound form of a vitamin, each R' is an independent monovalent radical selected from the group consisting of hydrogen, halogens, methyl, and ethyl, each R" is an independent monovalent radical selected from the group consisting of hydrogen and alkyl groups comprising 1 to 6 carbons, each t is an independent positive integer having a value of 0 to 2, each t' is an independent positive integer having a value of 0 to 2, no carbonate subunit has t=0 and t'=0, $Z^a$ is a first end group selected from the group consisting of hydrogen and groups comprising 1 to about 15 carbons, and $Z^b$ is a second end group selected from the group consisting of hydrogen and groups comprising 1 to about 15 carbons.

In an embodiment, each R' is hydrogen, each R" is methyl or ethyl, each t' is 1, each t" is 1, $Z^a$ is hydrogen, and $Z^b$ is hydrogen.

An even more specific gel-forming block copolymer has a structure according to formula (1-B):

each $L^e$ is independently a single bond or a divalent linking group comprising 1 to about 15 carbons, each V' is an independent moiety comprising a covalently bound form of a vitamin, each R' is an independent monovalent radical selected from the group consisting of hydrogen, halogens, methyl, and ethyl, each R" is an independent monovalent radical selected from the group consisting of hydrogen and alkyl groups comprising 1 to 6 carbons, $Z^a$ is a first end group selected from the group consisting of hydrogen and groups comprising 1 to about 15 carbons, and $Z^b$ is a second end group selected from the group consisting of hydrogen and groups comprising 1 to about 15 carbons.

In an embodiment, each R" is methyl or ethyl, $Z^a$ is hydrogen, and $Z^b$ is hydrogen.

A preferred method of preparing the gel-forming block copolymers utilizes an organocatalyzed ring opening polymerization of a cyclic carbonate monomer that comprises a covalently bound form of a vitamin, referred to as a vitamin-bearing monomer. The ring opening polymerization can be initiated by a poly(ethylene glycol) (PEG) having a number

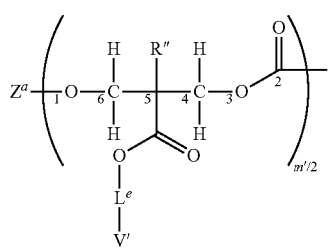
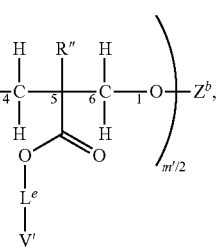

(1-B)

wherein the carbonate backbone atoms are numbered 1 to 6 in each carbonate subunit, d' is a positive number having a value of about 100 to about 600, each m' is an independent positive number having a value of 2 to about 20, average molecular weight (Mn) of about 5000 to about 25,000, more particularly 10,000 to about 20,000. The vitamin-bearing monomers can also be used for the preparation of the antimicrobial cationic copolymers described further below.

The vitamin bearing monomers can have a structure according to formula (5):

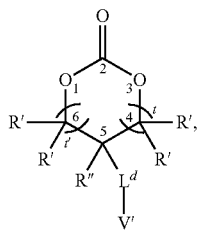

(5)

wherein
the ring atoms are shown numbered 1 to 6,
$L^d$ is a single bond or a divalent linking group comprising 1 to about 15 carbons,
V is a moiety comprising a covalently bound form of a vitamin,
each R' is an independent monovalent radical selected from the group consisting of hydrogen, halogens, methyl, and ethyl,
R" is a monovalent radical selected from the group consisting of hydrogen and alkyl groups comprising 1 to 6 carbons,
t is a positive integer having a value of 0 to 2,
t' is a positive integer having a value of 0 to 2, and
t and t' cannot both be zero.

In an embodiment, t and t' are each 1, each R' at carbon 4 is hydrogen, each R' at carbon 6 is hydrogen, and R" at carbon 5 is selected from the group consisting of hydrogen, methyl, and ethyl.

The cyclic carbonate monomers of formula (5) can be stereospecific or non-stereospecific.

Ring opening polymerization of vitamin-bearing monomers of formula (5) produces an initial polycarbonate having a vitamin-bearing subunit of formula (2) described further above.

The vitamin-bearing monomers can have the formula (6):

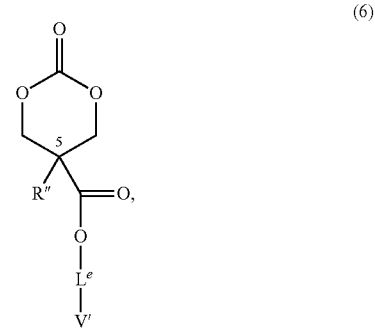

(6)

wherein
ring atom 5 is labeled,
$L^e$ is a single bond or a divalent linking group comprising 1 to about 14 carbons,
V' is a moiety comprising a covalently bound form of a vitamin, and
R" is a monovalent radical selected from the group consisting of hydrogen and alkyl groups comprising 1 to 6 carbons.

Ring opening polymerization of vitamin-bearing monomers of formula (6) produces an initial polycarbonate having a vitamin-bearing subunit of formula (3) described further above.

An exemplary compound of formula (6) is MTC-VitE:

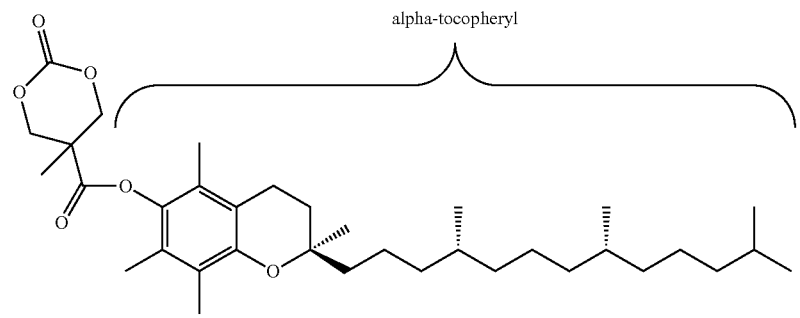 [SMILES: Cc1c(C)c2c(c(C)c1OC(=O)C1(C)COC(=O)OC1)CC[C@@](C)(CCC[C@H](C)CCC[C@H](C)CCCC(C)C)O2]

having a pendant alpha-tocopheryl group. MTC-VitE undergoes a ring opening polymerization forming a carbonate subunit having the structure:

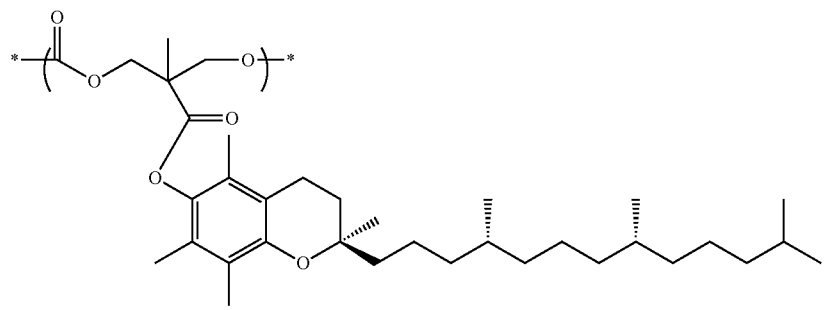

Another compound of formula (6) is MTC-VitD2, which has the structure:

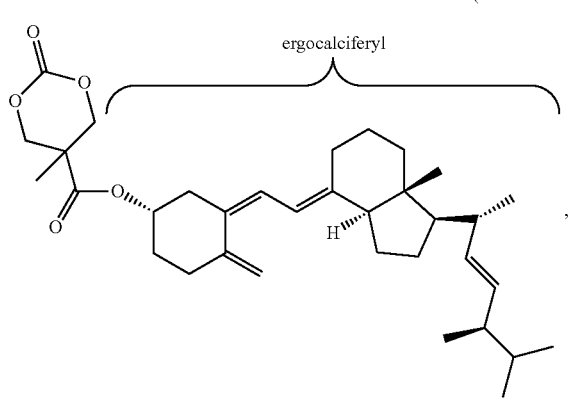

(MTC-VitD2)

which has a pendant ergocalciferyl group. MTC-VitD2 undergoes a ring opening polymerization forming a carbonate subunit having the structure:

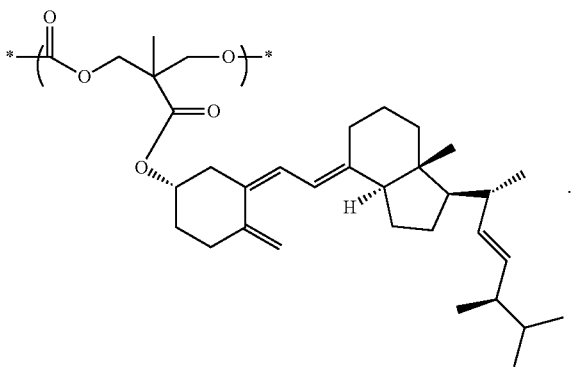

The vitamin-bearing monomers can have the formula (7):

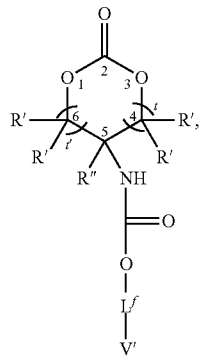

(7)

wherein the ring atoms are shown numbered 1 to 6, $L^f$ is a single bond or a divalent linking group comprising 1 to about 14 carbons, V' is a covalently bound form of a vitamin, each R' is an independent monovalent radical selected from the group consisting of hydrogen, halogens, methyl, and ethyl, R" is a monovalent radical selected from the group consisting of hydrogen and alkyl groups comprising 1 to 6 carbons, t is a positive integer having a value of 0 to 2, t' is a positive integer having a value of 0 to 2, and t and t' cannot both be zero.

Ring opening polymerization of vitamin-bearing monomers of formula (7) produces an initial polycarbonate having a vitamin-bearing subunit of formula (4) described further above.

Several preferred types of antimicrobial cationic polymers are described in the following section.

Antimicrobial Cationic Polymers Having One Polymer Chain (One-Armed)

A first antimicrobial cationic polymer has a structure in accordance with formula (8):

$$Z'—P'—Z'' \qquad (8),$$

wherein

Z' is a monovalent $C_1$-$C_{15}$ first end group, wherein Z' is linked to a backbone carbonyl group of P', Z" is a monovalent second end group selected from the group consisting of hydrogen and $C_1$-$C_{15}$ moieties, P' is a polymer chain consisting essentially of cationic carbonate subunits, wherein i) P' has a degree of polymerization (DP) of about 5 to about 45, ii) each of the cationic carbonate subunits comprises a backbone portion of the polymer chain and a $C_6$-$C_{25}$ cationic side chain linked to the backbone portion, and iii) the cationic side chain comprises a positive-charged heteroatom Q' of a quaternary ammonium group and/or quaternary phosphonium group, about 25% to about 100% of the cationic carbonate subunits, designated first cationic carbonate subunits, have a cationic side chain comprising 13 to about 25 carbons, and about 0% to about 75% of the cationic carbonate subunits, designated second cationic carbonate subunits, have a cationic side chain comprising 6 to 12 carbons.

Z' can be any suitable end group comprising 1 to 15 carbons. Z' comprises an oxygen, nitrogen or sulfur heteroatom that is linked to a backbone carbonyl of P' in the form of a carbonate, carbamate or thiocarbonate group, respectively. Z' can be a residue of an initiator used in a ring opening polymerization to form the cationic polymer. In an embodiment, Z' is a covalently bound form of $C_1$-$C_{15}$ compound. In another embodiment, Z' is a $C_1$-$C_{15}$ alkoxy or aryloxy group.

Z" is preferably linked to a backbone oxygen of P'. When Z" is hydrogen, the cationic polymer has a terminal hydroxy group. When Z" is not hydrogen, Z" can be any suitable end group comprising 1 to 15 carbons. In an embodiment, Z" is a covalently bound form of $C_1$-$C_{15}$ compound. In another embodiment, Z" is a $C_1$-$C_{15}$ acyl group.

The first cationic carbonate subunits preferably comprise a cationic side chain having 13 to about 20 carbons, even more preferably 15 to about 20 carbons.

In an embodiment, P' consists essentially of 25 mol % to about 75 mol % of the first cationic carbonate subunits and about 75 mol % to about 25 mol % of the second cationic carbonate subunits. In another embodiment, P' consists essentially of 25 mol % to about 50 mol % of the first cationic carbonate subunits and about 75 mol % to about 25 mol % of the second cationic carbonate subunits.

The cationic carbonate subunits can have a structure according to formula (9):

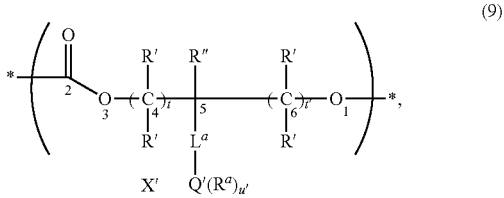

(9)

wherein $L^a$-$Q'(R^a)_{u'}$ is a $C_6$-$C_{25}$ cationic side chain comprising a quaternary ammonium group and/or quaternary phosphonium group, wherein $L^a$ is a divalent linking group comprising at least 3 carbons, $Q'$ is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, t is a positive integer having a value of 0 to 2,
t' is a positive integer having a value of 0 to 2,
t and t' cannot both be zero, and
X' is a negative-charged ion.

The starred bonds are attachment points to other portions of the polymer structure. The polymer backbone atoms of the cationic carbonate subunit are labeled 1 to 6 in formula (9). In this instance, the cationic side chain group is linked to backbone carbon 5 of the subunit. In an embodiment, t and t' are both 1, each R' is hydrogen, and R" is methyl or ethyl.

In a cationic polymer of formula (8) whose cationic carbonate subunits are of formula (9), each of the first cationic carbonate subunits has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

More specific cationic subunits have a structure in accordance with formula (10):

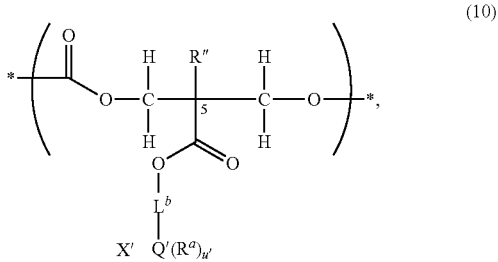

(10)

wherein $L^b$-$Q'(R^a)_{u'}$, is a $C_5$-$C_{24}$ cationic moiety comprising a quaternary ammonium group and/or quaternary phosphonium group, wherein $L^b$ is a divalent linking group comprising at least 2 carbons, $Q'$ is a tetravalent positive-charged nitrogen or phosphorus, u' has a value of 1 to 3, each $R^a$ is an independent radical having a valency of 1 to 3, and each $R^a$ comprises at least 1 carbon, R" is a monovalent radical selected from the group consisting of hydrogen, halogens, and alkyl groups comprising 1 to 6 carbons, and X' is a negative-charged ion.

In this instance, the cationic side chain group is $C(=O)O$-$L^b$-$Q'(R^a)_{u'}$, and $C(=O)O$-$L^b$ corresponds to divalent linking group $L^a$ of formula (9). The cationic side chain is linked to backbone carbon labeled 5.

In a cationic polymer of formula (8) whose cationic carbonate subunits are of formula (10), each of the first cationic carbonate subunits has a cationic side chain $C(=O)O$-$L^b$-$Q'(R^a)_{u'}$, comprising 13 to about 25 carbons, and each of the second cationic carbonate subunits has a cationic side chain $C(=O)O$-$L^b$-$Q'(R^a)_{u'}$, comprising 6 to 12 carbons.

Another more specific cationic subunit has a structure in accordance with formula (11):

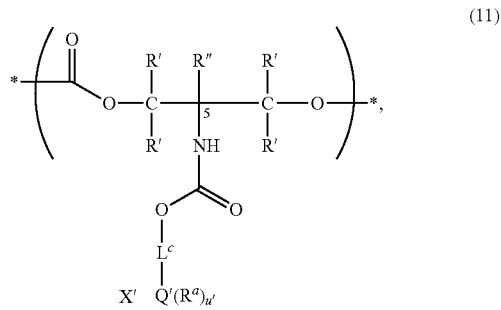

(11)

wherein $L^c$-$Q'(R^a)_{u'}$, is a $C_5$-$C_{24}$ cationic moiety comprising a quaternary ammonium group and/or quaternary phosphonium group, wherein $L^c$ is a divalent linking group comprising at least 2 carbons, $Q'$ is a tetravalent positive-charged nitrogen or phosphorus, u' has a value of 1 to 3, and each $R^a$ is an independent radical having a valency of 1 to 3, wherein each $R^a$ comprises at least 1 carbon, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, and X' is a negative-charged ion.

In this instance the cationic side chain is $N(H)C(=O)O$-$L^c$-$Q'(R^a)_{u'}$, and $N(H)C(=O)O$-$L^c$ corresponds to divalent linking group $L^a$ of formula (9). The cationic side chain is linked to backbone carbon labeled 5. Serinol and/or threoninol provide useful starting materials for the formation of subunits of formula (11).

In a cationic polymer of formula (8) whose cationic carbonate subunits are of formula (11), each of the first cationic carbonate subunits has a cationic side chain $N(H)C(=O)O$-$L^c$-$Q'(R^a)_{u'}$, comprising 13 to about 25 carbons, and each of the second cationic carbonate subunits has a cationic side chain $N(H)C(=O)O$-$L^c$-$Q'(R^a)_{u'}$, comprising 6 to 12 carbons.

Using the cationic subunit of formula (9), the cationic polymers of formula (8) can have a structure in accordance with formula (12):

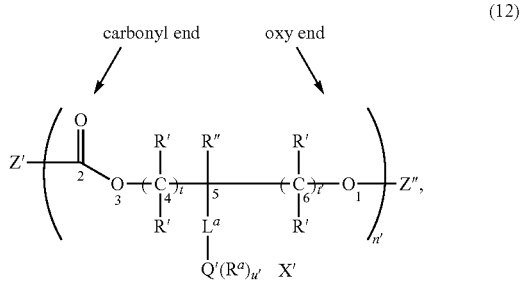

(12)

wherein:
n' represents the number of cationic carbonate subunits, wherein n' has a value of about 5 to about 45, Z' is a monovalent $C_1$-$C_{15}$ first end group, Z" is a monovalent second end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;

and wherein about 25% to 100% of the cationic carbonate subunits of the cationic polymer, designated first cationic carbonate subunits, have a cationic side chain $L^a$-$Q'(R^a)_{u'}$ comprising 13 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 12 carbons.

As shown in formula (12), the polymer chain comprises a backbone portion comprising a oxycarbonyl group at a first end of the chain (referred to as the "carbonyl end"), and a backbone oxygen at a second end of the chain (referred to as the "oxy end"). The backbone atoms of the cationic carbonate subunit are shown numbered 1 to 6.

In formula (12), $L^a$ and $Q'(R^a)_{u'}$ of the first cationic carbonate subunits can individually have 3 to about 22 carbons, with the proviso that $L^a$-$Q'(R^a)_{u'}$ has a total of 13 to about 25 carbons. Preferably, the $L^a$ group of the first cationic carbonate subunits comprises 5 to about 12 carbons, or more preferably 8 to about 12 carbons. Preferably, $Q'(R^a)_{u'}$ of the first cationic carbonate subunits comprise 3 to about 18 carbons, more preferably 4 to about 18 carbons.

Likewise, $L^a$ and $Q'(R^a)_{u'}$ of the second cationic carbonate subunits of formula (12) can each have at least 3 carbons, with the proviso that $L^a$-$Q'(R^a)_{u'}$ has a total of 6 to 12 carbons.

In an embodiment, Z" is hydrogen. In another embodiment, the first cationic carbonate subunits have a cationic side chain $L^a$-$Q'(R^a)_{u'}$ comprising 15 to about 20 carbons.

As more specific non-limiting examples, Z' can be benzyloxy and/or 4-methylbenzyloxy, and Z" can be hydrogen and/or acetyl.

The end groups Z' and/or Z", and end groups described below, can enhance antimicrobial efficacy and or stabilize the cationic polymer from potential unwanted side reactions (e.g., chain scission) caused by, for example, an unblocked nucleophilic hydroxy end group. Bulkier end groups can also provide hydrophobicity allowing control of the amphiphilic properties of the cationic polymers.

The antimicrobial cationic polymers can have a structure in accordance with formula (13):

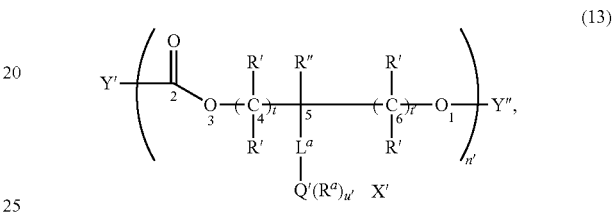

(13)

wherein
n' represents the number of cationic carbonate subunits, and n' has a value of about 5 to about 45, Y' is a monovalent first end group comprising a covalently bound form of a biologically active compound selected from the group consisting of steroids, non-steroid hormones, vitamins, and drugs, Y" is a monovalent second end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;

and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (13) can individually have 3 to about 22 carbons, with the proviso that $L^a$-$Q'(R^a)_{u'}$ has a total of 10 to about 25 carbons. In an embodiment, each of the first cationic carbonate subunits of formula (13) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

The biologically active compound can be stereospecific or non-stereospecific. In an embodiment, Y' comprises a covalently bound form of a steroid (e.g., cholesterol), designated S'. The steroid group can enhance biocompatibility of the cationic polymer.

In another embodiment, Y' comprises a covalently bound form of a vitamin, (e.g., alpha-tocopherol (a vitamin E compound) and/or ergocalciferol (vitamin D2)).

Y' can have a structure S'-L'-* wherein S' is a steroid group and L' is a single bond or any suitable divalent linking group comprising 1 to about 10 carbons. In this instance, L' links S' to the carbonyl end of the polycarbonate backbone.

The antimicrobial cationic polymers can have a structure in accordance with formula (14):

$$W'-\left(\underset{2}{\overset{O}{\parallel}}{C}-\underset{3}{O}-(\underset{4}{\overset{R'}{\underset{R'}{C}}})_t-\underset{5}{\overset{R''}{\underset{L^a}{C}}}-(\underset{6}{\overset{R'}{\underset{R'}{C}}})_{t'}-\underset{1}{O}\right)_{n'}-W'', \quad (14)$$
$$Q'(R^a)_{u'} \quad X'$$

wherein n' represents the number of cationic carbonate subunits, and n' has a value of about 5 to about 45, W' is a monovalent $C_1$-$C_{15}$ first end group, W'' is a monovalent second end group comprising a covalently bound form of a biologically active compound selected from the group consisting of steroids, non-steroid hormones, vitamins, and drugs, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R'' is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;

and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (14) can individually have 3 to about 22 carbons, with the proviso that $L^a$-$Q'(R^a)_{u'}$ has a total of 10 to about 25 carbons. In an embodiment, each of the first cationic carbonate subunits of formula (14) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

W'' can comprise a stereospecific or non-stereospecific form of the biologically active compound. In an embodiment, W'' comprises a covalently bound form of cholesterol, alpha-tocopherol (a vitamin E compound), ergocalciferol (vitamin D2), or combinations thereof.

W'' can have the general structure S'-L''-* wherein S' is a steroid group and L'' is a single bond or any suitable divalent linking group comprising 1 to about 10 carbons. In this instance, L'' links S' to the oxy end of the polycarbonate backbone.

The antimicrobial cationic polymer can be a random copolymer having a structure in accordance with formula (15):

$$Z'-P''-Z'' \quad (15),$$

wherein

Z' is a monovalent $C_1$-$C_{15}$ first end group,

Z'' is a monovalent second end group selected from the group consisting of hydrogen and $C_1$-$C_{15}$ moieties, P'' is a polymer chain consisting essentially of I) about 85 mol % to 99.9 mol % of cationic carbonate subunits, and II) 0.1 mol % to about 15 mol % of carbonate subunits comprising a covalently bound form of a steroid and/or a vitamin compound, wherein i) P'' has a degree of polymerization (DP) of about 5 to about 45, ii) each of cationic carbonate subunits comprises a polymer backbone portion and a cationic side chain portion linked to the polymer backbone portion, and iii) each cationic side chain portion comprises a positively charged heteroatom of a quaternary ammonium group and/or a quaternary phosphonium group, about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (15) can individually have 3 to about 22 carbons, with the proviso that $L^a$-$Q'(R^a)_{u'}$ has a total of 10 to about 25 carbons. In an embodiment, each of the first cationic carbonate subunits of formula (15) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

The antimicrobial cationic polymers of formula (15) can have a structure in accordance with formula (16):

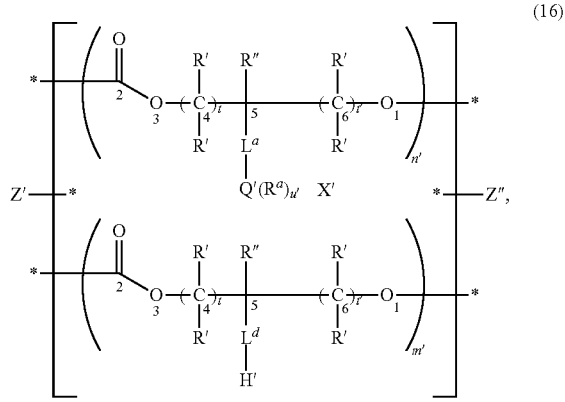

(16)

wherein n' represents the number of cationic carbonate subunits, wherein n' has a value greater than 0, m' represents the number of carbonate subunits, wherein m' has a value greater than 0, n'+m' has a value of about 5 to about 45, a ratio of m':n' is about 15:85 to about 0.1:99.9, Z' is a monovalent $C_1$-$C_{15}$ first end group, Z" is a monovalent second end group selected from the group consisting of hydrogen and $C_1$-$C_{15}$ moieties, each $L^d$ is an independent divalent linking group selected from the group consisting of single bond and monovalent radicals comprising 1 to about 10 carbons, each H' is an independent monovalent radical comprising a covalently bound form of a steroid and/or a vitamin compound, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;

and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

The vertical stacking of subunits within the square brackets of formula (16) indicates a random distribution of subunits within the polymer chain.

$L^a$ and $Q'(R^a)_{u'}$ of the first cationic carbonate subunits of formula (16) can individually have 3 to about 22 carbons, with the proviso that $L^a$-$Q'(R^a)_{u'}$ has a total of 10 to about 25 carbons. In an embodiment, each of the first cationic carbonate subunits of formula (16) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

H' can comprise a covalently bound form of a vitamin E compound, vitamin D compound, or combinations thereof. Preferably, the vitamin compound is alpha-tocopherol (a vitamin E compound), ergocalciferol (vitamin D2), or a combination thereof.

The discussion that follows applies generally to all of the above-described cationic polymers.

Exemplary non-limiting divalent $L^a$ groups include:

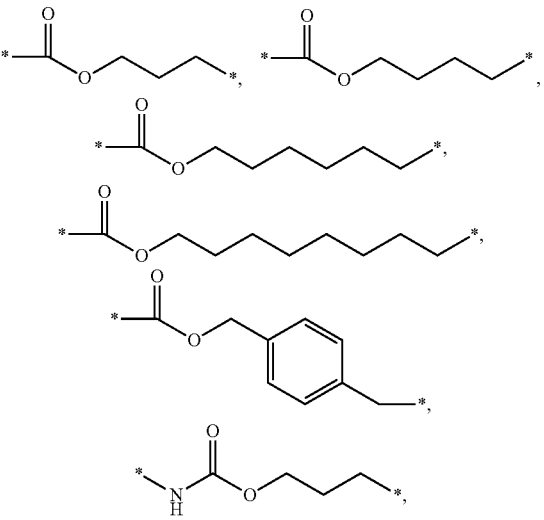

and combinations thereof. In these examples, the starred bonds of the carbonyl and carbamate nitrogen are linked to the polycarbonate backbone (e.g., the backbone carbon labeled 5 in the above cationic carbonate subunits), and the starred bonds of the methylene groups are linked to Q'.

Together, $L^a$ and $Q'(R^a)_{u'}$ form a quaternary ammonium group or a quaternary phosphonium group, meaning the positive-charged heteroatom Q' is bonded to a carbon of $L^a$ and up to three independent $R^a$ groups.

Each $R^a$ comprises at least one carbon. Each $R^a$ can be a monovalent hydrocarbon substituent (e.g., methyl, ethyl, etc.), in which case u' is 3.

An $R^a$ can form a ring with Q', in which case the $R^a$ of the ring has a valency of 2. For example, $Q'(R^a)_{u'}$ can be:

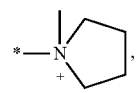

wherein the starred bond is linked to $L^a$, Q' is nitrogen, and u' is 2. In this example, a first $R^a$ is a divalent butylene group (*—$(CH_2)_4$—*), and a second $R^a$ is methyl.

$R^a$ can form a multi-cyclic moiety with Q'. For example $Q'(R^a)_{u'}$ can be:

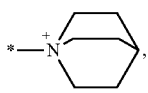

wherein the starred bond is linked to $L^a$, Q' is nitrogen, u' is 1, and $R^a$ is the fragment

having a valency of 3.

The $R^a$ groups can also independently comprise oxygen, nitrogen, sulfur, and/or another heteroatom. In an embodiment, each $R^a$ is an independent monovalent branched or unbranched hydrocarbon substituent.

Exemplary non-limiting $R^a$ groups include methyl, ethyl, n-propyl, iso-propyl, n-butyl, iso-butyl, n-pentyl, n-hexyl, n-heptyl, n-octyl, and benzyl.

Exemplary non-limiting $Q'(R^a)_{u'}$ groups include:

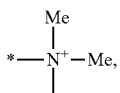 (trimethyl ammonium)

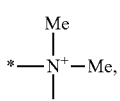 (dimethyl ethyl ammonium)

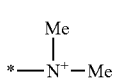 (dimethyl butyl ammonium)

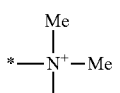 (dimethyl hexyl ammonium)

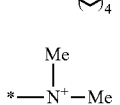 (dimethyl octyl ammonium)

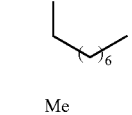 (dimethyl benzyl ammonium)

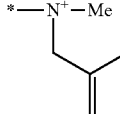 (methyl imidazolium)

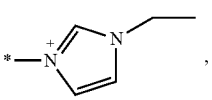 (ethyl imidazolium)

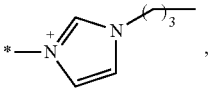 (butyl imidazolium)

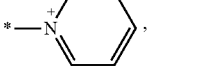 (pyridinium)

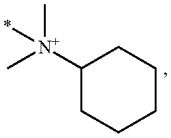 (dimethyl cyclohexyl ammonium)

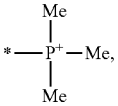 (trimethyl phosphonium)

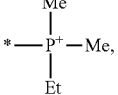 (dimethyl ethyl phosphonium)

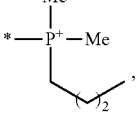 (dimethyl butyl phosphonium)

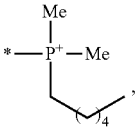 (dimethyl hexyl phosphonium)

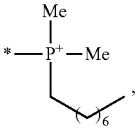 (dimethyl octyl phosphonium)

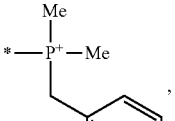 (dimethyl benzyl phosphonium)

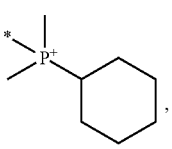 (dimethyl cyclohexyl phosphonium)

, and combinations thereof.

In the foregoing examples, it should be understood that the positive-charged nitrogen and phosphorus are tetravalent, and the starred bond is linked to a carbon of $L^a$. The $Q'$ groups can be present in the cationic polymer singularly or in combination.

Exemplary negative-charged ions X' include halides (e.g., chloride, bromide, and iodide), carboxylates (e.g., acetate and benzoate), and/or sulfonates (e.g., tosylate). The X' ions can be present singularly or in combination.

Exemplary non-limiting cationic carbonate subunits include the following:

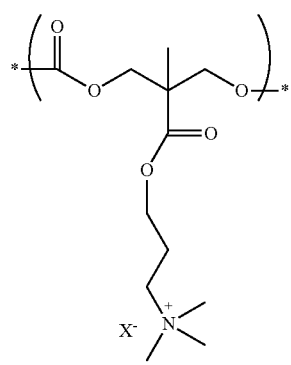

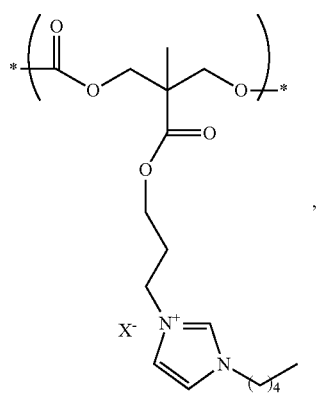

-continued

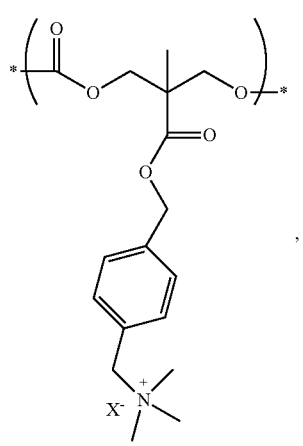

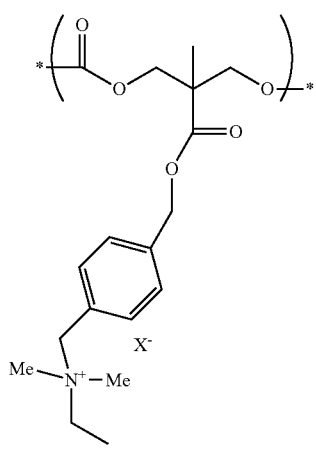

33
-continued
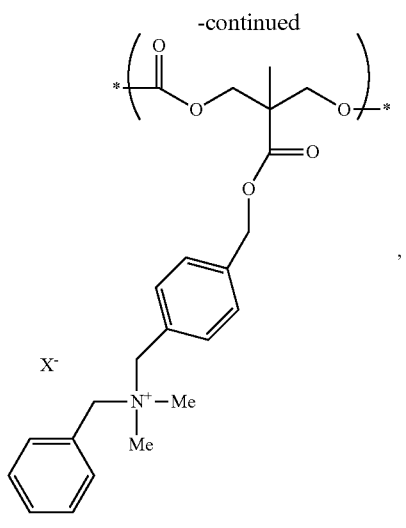
,
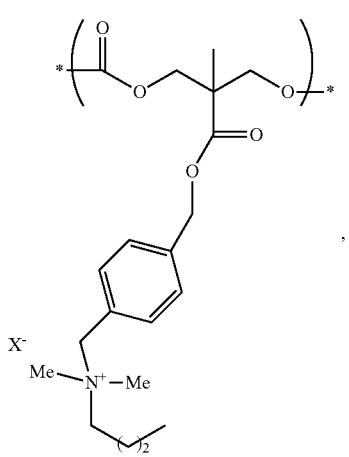
,
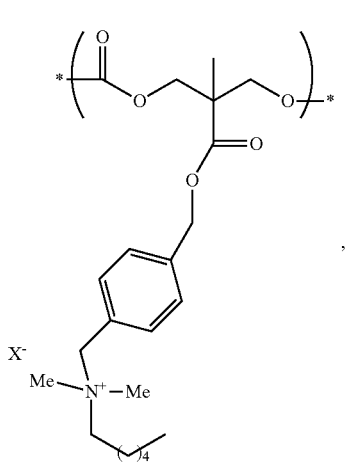
,
34
-continued
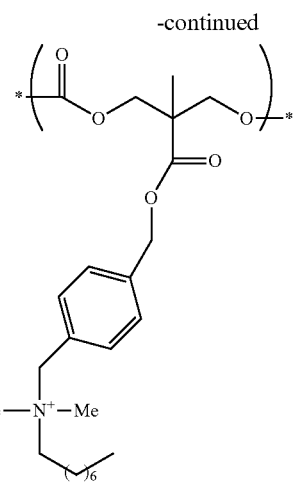
,
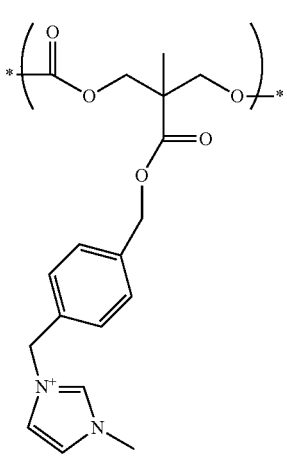
,
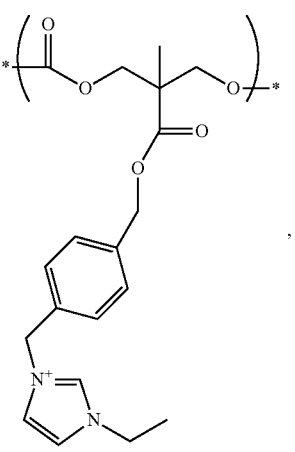
, 35
-continued
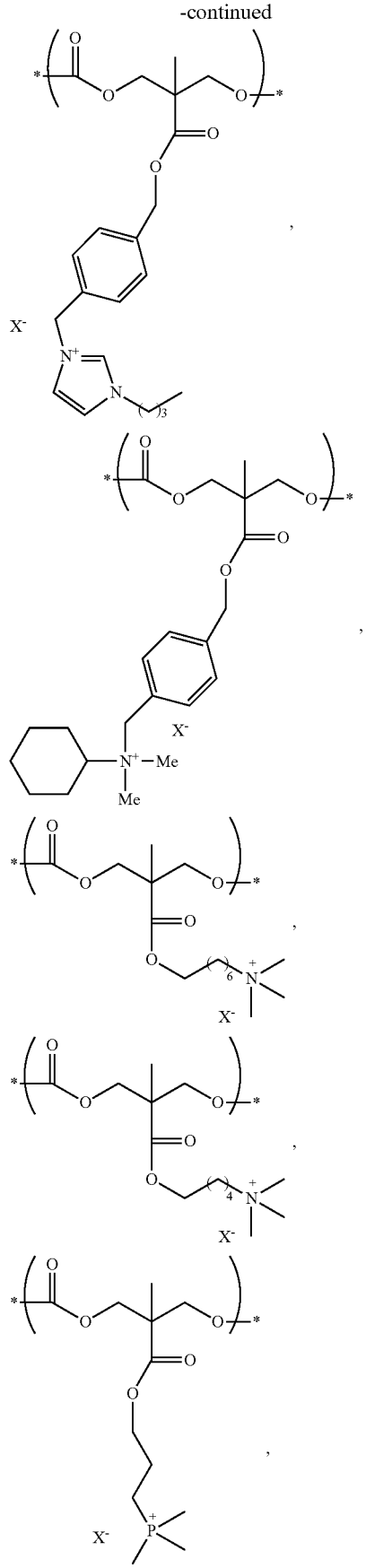
36
-continued
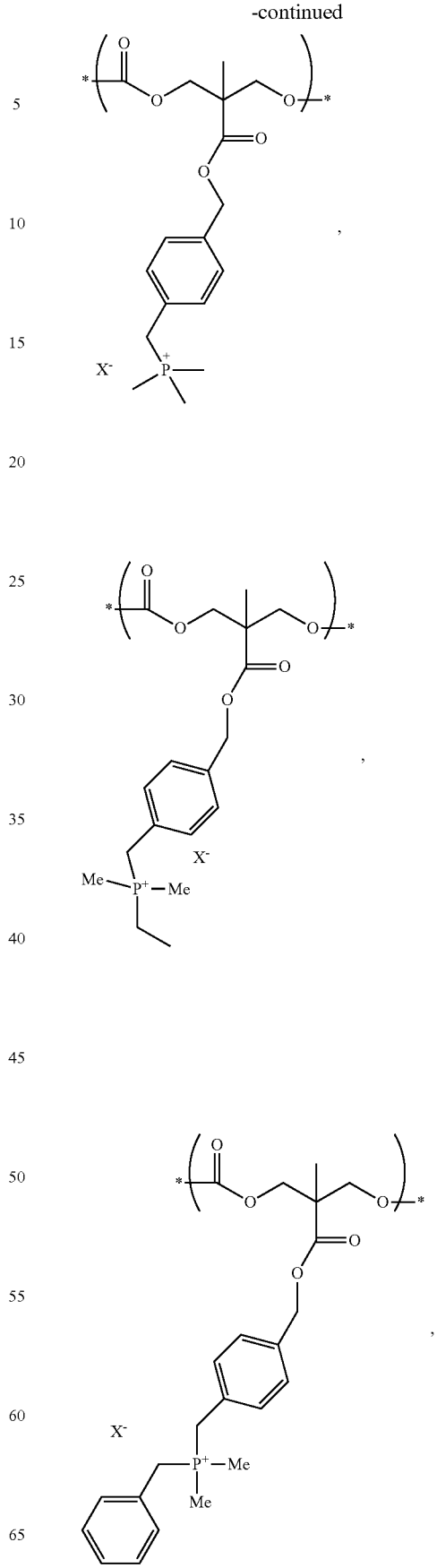

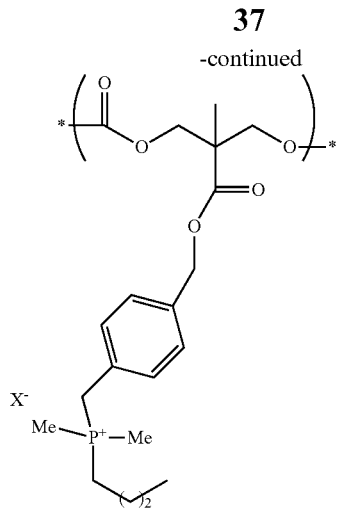

,

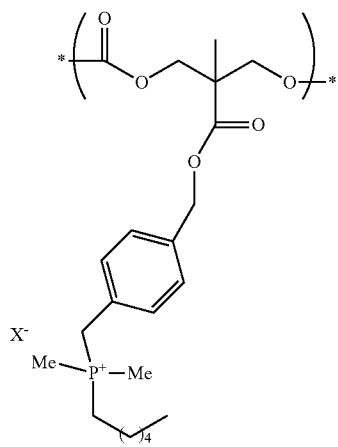

,

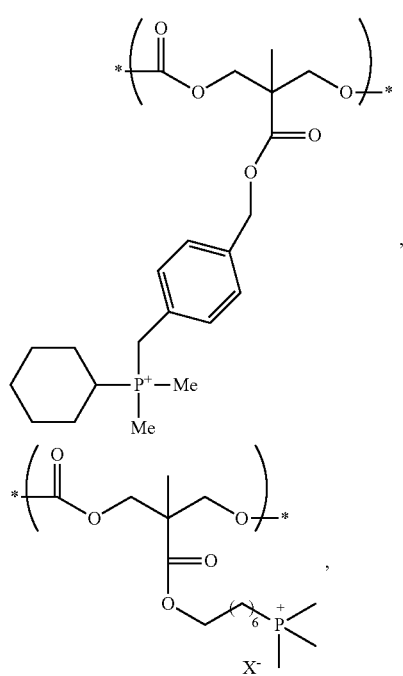

,

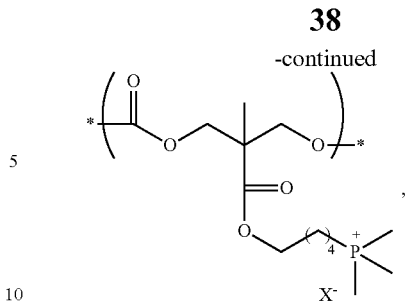

, and combinations thereof, wherein $X^-$ is a negative-charged ion associated ionically with the cation.

In general, antimicrobial activity of the cationic polymers is favored by spacing the positive-charged heteroatom Q' from the polycarbonate backbone in 25 mol % to 100 mol % of the cationic carbonate subunits (first cationic carbonate subunits) by the shortest path having 6 or more contiguously linked atomic centers from the polymer backbone. The shortest path is defined as the lowest number of contiguously linked atomic centers joining Q' to the polymer backbone. The contiguously linked atomic centers should be understood to be between the polycarbonate backbone and Q'. For example, if $L^\alpha$-Q' is:

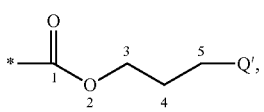

then the shortest path from the polymer backbone to Q' has 5 contiguously linked atomic centers, as numbered. The shortest path does not include the carbonyl oxygen. As another example, if $L^\alpha$-Q' is

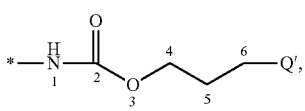

then the shortest path from the polymer backbone to Q' has 6 contiguously linked atomic centers, as numbered. The shortest path does not include the amide hydrogen and the carbonyl oxygen. As another example, if $L^\alpha$-Q' is

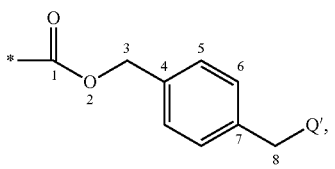

then the shortest path from the polymer backbone to Q' has 8 contiguously linked atomic centers, as numbered. The shortest path does not include two carbons of the aromatic ring and the carbonyl oxygen. As another example, if $L^\alpha$-Q' is

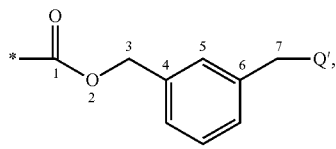

then the shortest path from the polymer backbone to Q' has 7 contiguously linked atomic centers, as numbered. The shortest path does not include three carbons of the aromatic ring and the carbonyl oxygen. Finally, as another example, if $L^a$-Q' is

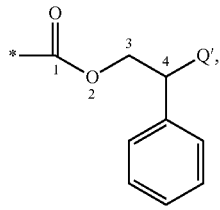

then the shortest path from the polymer backbone to Q' has 4 contiguously linked atomic centers, as numbered. The shortest path does not include the aromatic ring and the carbonyl oxygen.

Preferably, Q' of the first carbonate subunits is spaced from the polymer backbone by the shortest path having 6 to about 15 contiguously linked atomic centers, and more preferably 8 to about 15 contiguously linked atomic centers.

The steroid group S' can originate from a naturally occurring human steroid, non-human steroid, and/or a synthetic steroid compound. Herein, a steroid group comprises a tetracyclic ring structure:

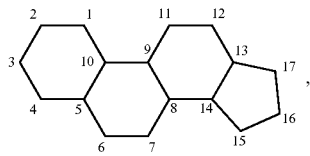

wherein the 17 carbons of the ring system are numbered as shown. The steroid group can comprise one or more additional substituents attached to one or more of the numbered ring positions. Each ring of the tetracyclic ring structure can independently comprise one or more double bonds.

Exemplary steroid groups include cholesteryl, from cholesterol, shown below without stereochemistry:

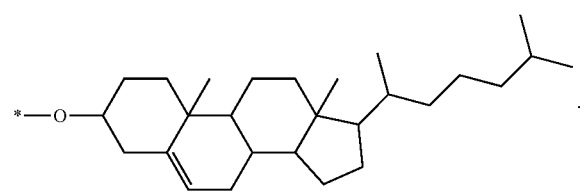 [SMILES: *OC1CCC2(C)C(=CCC3C2CCC2(C)C(C(C)CCCC(C)C)CCC32)C1]

Non-limiting stereospecific structures of cholesteryl include

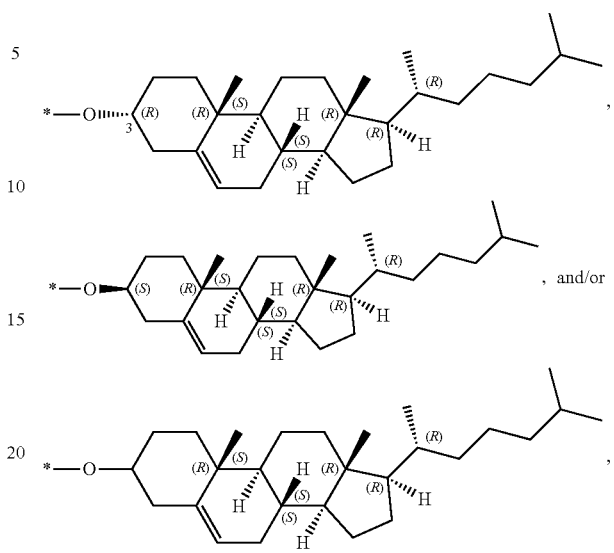

where the R,S stereoconfiguration of each stereospecific asymmetric center is labeled.

Additional non-limiting steroid groups include

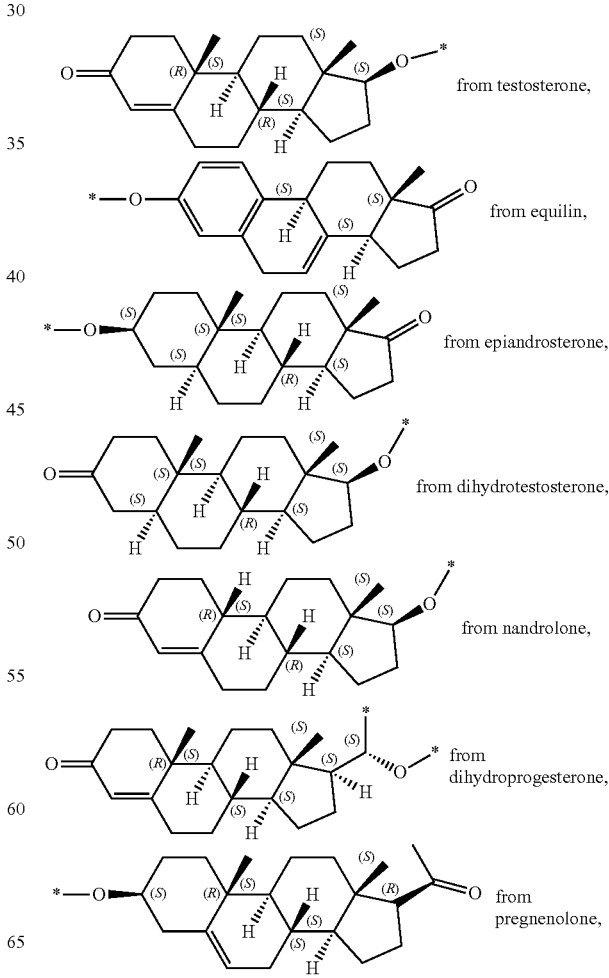

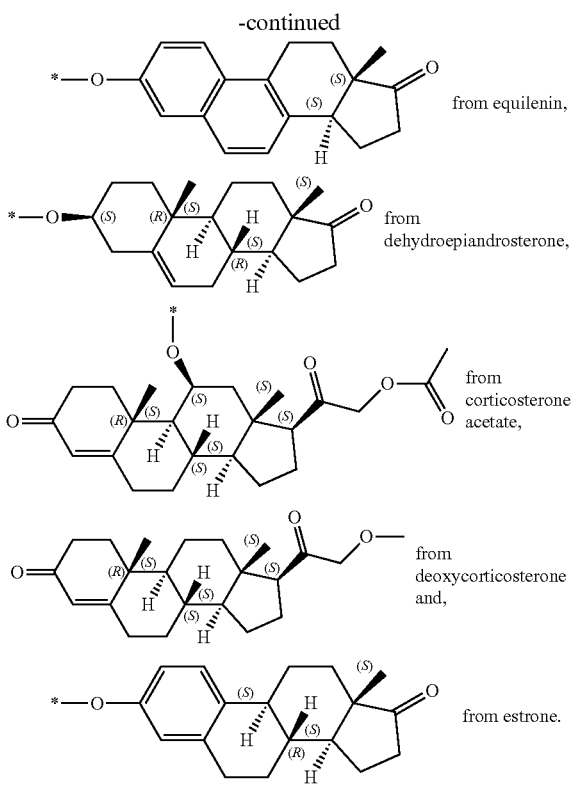

from equilenin, from dehydroepiandrosterone, from corticosterone acetate, from deoxycorticosterone and, from estrone.

The starred bonds represent attachment points. For example, the starred bond of each of the above steroid groups can be linked to a terminal carbonyl group of the polycarbonate backbone by way of a divalent linking group L'. Alternatively, the starred bond of the steroid group can be directly linked to a terminal carbonyl group of the polycarbonate backbone (i.e., L' can be a single bond).

Those of skill in the art will recognize that each asymmetric center of the steroid groups can be present as the R stereoisomer, S stereoisomer, or as a mixture of R and S stereoisomers. Additional steroid groups S' include the various stereoisomers of the above structures. The cationic polymer can comprise a steroid group as a single stereoisomer or as a mixture of stereoisomers.

In an embodiment, S' is cholesteryl group, wherein the cholesteryl group is a mixture of isomers

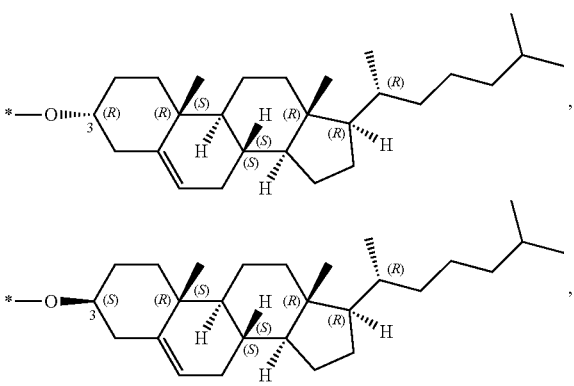

indicated by the structure

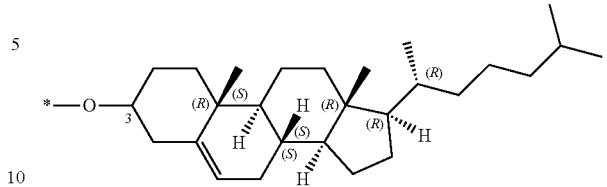

More specific steroid-containing cationic polymers have a structure in accordance with formula (17):

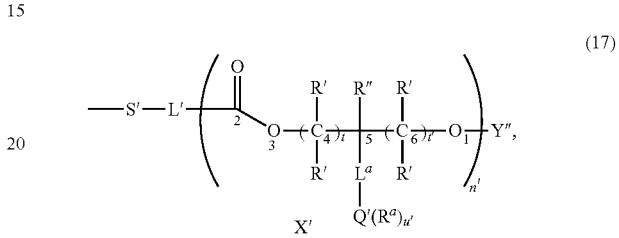

(17)

wherein n' represents the number of cationic carbonate subunits, and has a value of about 5 to about 45, S'-L' is a first end group, wherein L' is a single bond or a divalent linking group comprising 1 to about 10 carbons, and S' comprises a covalently bound form of a steroid, Y" is a monovalent second end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;

and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (17) can individually have 3 to about 22 carbons, with the proviso that $L^a$-$Q'(R^a)_{u'}$ has a total of 10 to about 25 carbons. In an embodiment, each of the first cationic carbonate subunits of formula (17) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

In formula (17), when L' is a single bond, S' is linked directly to the terminal carbonyl group of the polycarbonate backbone. In an embodiment, L' is a divalent linking group comprising an alkylene oxide selected from the group consisting of ethylene oxide (*—CH$_2$CH$_2$O—*), propylene oxide *—CH$_2$CH$_2$CH$_2$O—*, and/or tri(ethylene oxide) (*—CH$_2$CH$_2$OCH$_2$CH$_2$OCH$_2$CH$_2$O—*), wherein the starred bond of the oxygen is linked to the terminal carbonyl group of the polycarbonate backbone and the starred bond of the carbon is linked to S'.

The steroid-containing cationic polymers can comprise one or a combination of the cationic carbonate subunits described further above.

The steroid-containing cationic polymers can have a structure in accordance with formula (18):

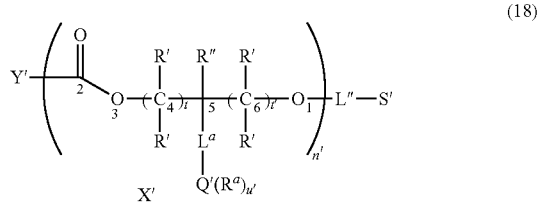

wherein n' represents the number of cationic carbonate subunits, and has a value of about 5 to about 45, Y' is a monovalent C$_1$-C$_{15}$ first end group, S'-L" is a second end group, wherein L" is a single bond or a divalent linking group comprising 1 to about 10 carbons and S' comprises a covalently bound form of a steroid, each L$^a$-Q'(R$^a$)$_{u'}$ is an independent C$_6$-C$_{25}$ cationic side chain comprising a quaternary ammonium group and/or quaternary phosphonium group, wherein L$^a$ is a divalent linking group comprising at least 3 carbons, Q' is a tetravalent positive-charged nitrogen or phosphorus, u' has a value of 1 to 3, each R$^a$ is an independent radical having a valency of 1 to 3, and each R$^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;
and wherein about 25% to 100% of the cationic carbonate subunits of the cationic polymer, designated first cationic carbonate subunits, have a cationic side chain L$^a$-Q'(R$^a$)$_{u'}$ comprising 10 to about 25 carbons, and 0% to about 75% of the cationic carbonate subunits of the cationic polymer, designated second cationic carbonate subunits, have a cationic side chain L$^a$-Q'(R$^a$)$_{u'}$ comprising 6 to 9 carbons.

The group S'-L" is linked to the oxy end of the polycarbonate backbone, and Y' is linked to the carbonyl end of the polycarbonate backbone.

L$^a$ and Q'(R$^a$)$_{u'}$ of the first cationic carbonate subunits of formula (18) can individually have 3 to about 22 carbons, with the proviso that L$^a$-Q'(R$^a$)$_{u'}$ has a total of 10 to about 25 carbons. In an embodiment, each of the first cationic carbonate subunits of formula (18) has a cationic side chain L$^a$-Q'(R$^a$)$_{u'}$ comprising 13 to about 25 carbons, and each of the second cationic carbonate subunits has a cationic side chain L$^a$-Q'(R$^a$)$_{u'}$ comprising 6 to 12 carbons.

Cationic Polymers Having Two Cationic Polymer Chains (Two-Armed Cationic Polymers)

The antimicrobial cationic polymers can have a structure in accordance with formula (19):

$$Z^c-P^b-C'-P^b-Z^c \qquad (19),$$

wherein

C' is a C$_2$-C$_{15}$ divalent linking group joining polymer chains P$^b$, wherein C' comprises i) a first heteroatom linked to a first polymer chain P$^b$, wherein the first heteroatom is selected from the group consisting of nitrogen, oxygen, and sulfur, and ii) a second heteroatom linked to a second polymer chain P$^b$, wherein the second heteroatom is selected from the group consisting of nitrogen, oxygen, and sulfur, each Z$^c$ is an independent monovalent end group selected from the group consisting of hydrogen and C$_1$-C$_{15}$ moieties, each polymer chain P$^b$ consists essentially of cationic carbonate subunits, wherein i) the cationic polymer comprises a total of 5 to about 45 cationic carbonate subunits, ii) each of the cationic carbonate subunits comprises a backbone portion of the polymer chain and a cationic side chain linked to the backbone portion, and iii) the cationic side chain comprises a positive-charged heteroatom Q' of a quaternary ammonium group and/or quaternary phosphonium group, about 25% to 100% of all the cationic carbonate subunits of the cationic polymer, designated first cationic carbonate subunits, have a cationic side chain comprising 10 to about 25 carbons, and 0% to about 75% of the cationic carbonate subunits of the cationic polymer, designated second cationic carbonate subunits, have a cationic side chain comprising 6 to 9 carbons.

L$^a$ and Q'(R$^a$)$_{u'}$ of the first cationic carbonate subunits of formula (19) can individually have 3 to about 22 carbons, with the proviso that L$^a$-Q'(R$^a$)$_{u'}$ has a total of 10 to about 25 carbons. In an embodiment, each of the first cationic carbonate subunits of formula (19) has a cationic side chain L$^a$-Q'(R$^a$)$_{u'}$ comprising 13 to about 25 carbons, and each of the second cationic carbonate subunits has a cationic side chain L$^a$-Q'(R$^a$)$_{u'}$ comprising 6 to 12 carbons.

In an embodiment, each Z$^c$ is hydrogen. In another embodiment, the positive-charged heteroatom Q' of the first cationic carbonate subunits is spaced from the backbone portion by the shortest path having 6 to about 15 contiguously linked atomic centers between Q' and the backbone portion.

More specific cationic polymers of formula (19) have a structure according to formula (20):

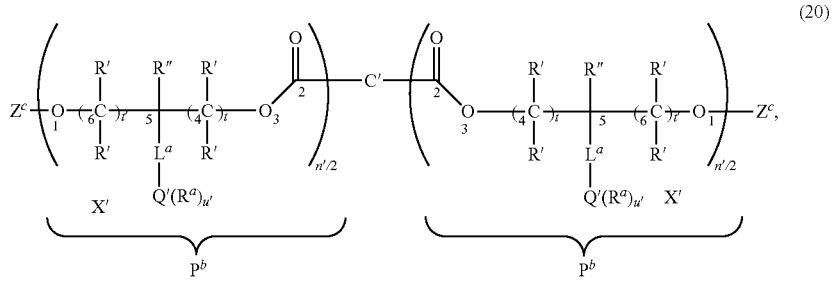

(20)

wherein n' represents the total number of cationic carbonate subunits of the cationic polymer, and has a value of about 5 to about 45, C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, the polymer chains $P^b$ consist essentially of the cationic carbonate subunits, each $Z^c$ is an independent monovalent end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;
and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (20) can individually have 3 to about 22 carbons, with the proviso that $L^a$-$Q'(R^a)_{u'}$ has a total of 10 to about 25 carbons. In an embodiment, each of the first cationic carbonate subunits of formula (20) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

C' can be a residue of a non-polymeric di-nucleophilic initiator used to prepare the cationic polymer by ring opening polymerization.

In another antimicrobial polymer, the fragment linking the two cationic polymer chains comprises a covalently bound form of a biologically active compound selected from the group consisting of steroids, non-steroid hormones, vitamins, and drugs. These antimicrobial cationic polymers have a structure in accordance with formula (21):

$$Z^c-P^b-C''-P^b-Z^c \qquad (21),$$

wherein

C" is a divalent linking group joining polymer chains $P^b$, wherein C" comprises i) a first heteroatom linked to a first polymer chain $P^b$, wherein the first heteroatom is selected from the group consisting of nitrogen, oxygen, and sulfur, ii) a second heteroatom linked to a second polymer chain $P^b$, wherein the second heteroatom is selected from the group consisting of nitrogen, oxygen, and sulfur, and iii) a covalently bound form of a compound selected from the group consisting of steroids, non-steroid hormones, vitamins, and drugs, each $Z^c$ is an independent monovalent end group selected from the group consisting of hydrogen and $C_1$-$C_{15}$ moieties, each polymer chain $P^b$ consists essentially of cationic carbonate subunits, wherein i) the cationic polymer comprises a total of 5 to about 45 cationic carbonate subunits, ii) each of the cationic carbonate subunits comprises a backbone portion of the polymer chain and a $C_6$-$C_{25}$ cationic side chain linked to the backbone portion, and iii) the cationic side chain comprises a positive-charged heteroatom Q' of a quaternary ammonium group and/or quaternary phosphonium group, about 25% to 100% of the cationic carbonate subunits of the cationic polymer, designated first cationic carbonate subunits, have a cationic side chain group comprising 10 to about 25 carbons, and 0% to about 75% of the cationic carbonate subunits of the cationic polymer, designated second cationic carbonate subunits, have a cationic side chain group comprising 6 to 9 carbons.

$L^a$ and $Q'(R^a)_{u'}$ of the first cationic carbonate subunits of formula (21) can individually have 3 to about 22 carbons, with the proviso that $L^a$-$Q'(R^a)_{u'}$ has a total of 10 to about 25 carbons. In an embodiment, each of the first cationic carbonate subunits of formula (21) has a cationic side chain comprising 13 to about 25 carbons, and each of the second cationic carbonate subunits has a cationic side chain comprising 6 to 12 carbons.

The positive-charged heteroatom Q' of the first cationic carbonate subunits can be spaced from the backbone portion by the shortest path having 6 to about 18 contiguously linked atomic centers between Q' and the backbone portion.

In an embodiment, C" comprises a covalently bound form of cholesterol. In another embodiment, C" comprises a covalently bound form of a vitamin selected from the group consisting of alpha-tocopherol, ergocalciferol, and combinations thereof.

More specific cationic polymers of formula (21) have a structure according to formula (22):

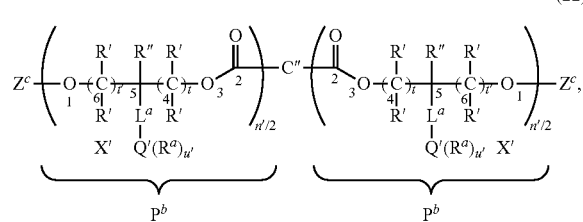

wherein n' represents the total number of cationic carbonate subunits of the cationic polymer, and has a value of about 5 to about 45, C" is a divalent linking group joining polymer chains $P^b$, wherein C" comprises i) a first heteroatom linked to a first polymer chain $P^b$, wherein the first heteroatom is selected from the group consisting of nitrogen, oxygen, and sulfur, ii) a second heteroatom linked to a second polymer chain $P^b$, wherein the second heteroatom is selected from the group consisting of nitrogen, oxygen, and sulfur, and iii) a covalently bound form of a compound selected from the group consisting of steroids, non-steroid hormones, vitamins, and drugs, each of the polymer chains $P^b$ consists essentially of cationic carbonate subunits, each $Z^c$ is an independent monovalent end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;
and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (22) can individually have 3 to about 22 carbons, with the proviso that $L^a$-$Q'(R^a)_{u'}$ has a total of 10 to about 25 carbons. In an embodiment, each of the first cationic carbonate subunits of formula (22) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

The antimicrobial cationic polymers can have a structure in accordance with formula (23):

$$Z^c\text{—}P^c\text{—}C'\text{—}P^c\text{—}Z^c \qquad (23),$$

wherein

C' is a $C_2$-$C_{15}$ divalent linking group joining polymer chains $P^c$, wherein C' comprises i) a first heteroatom linked to a first polymer chain $P^c$, wherein the first heteroatom is selected from the group consisting of nitrogen, oxygen, and sulfur, and ii) a second heteroatom linked to a second polymer chain $P^c$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each $P^c$ is a polymer chain consisting essentially of I) about 85 mol % to 99.9 mol % of cationic carbonate subunits, and II) 0.1 mol % to about 15 mol % of carbonate subunits comprising a covalently bound form of a steroid and/or a vitamin compound, wherein i) the cationic polymer has a total number of subunits of about 5 to about 45, ii) each of the cationic carbonate subunits comprises a polymer backbone portion and a $C_6$-$C_{25}$ cationic side chain portion linked to the polymer backbone portion, and iii) each cationic side chain portion comprises a positive-charged heteroatom Q' of a quaternary ammonium group and/or quaternary phosphonium group, about 25% to 100% of the cationic carbonate subunits of the cationic polymer, designated first cationic carbonate subunits, have a cationic side chain group comprising 10 to about 25 carbons, and 0% to about 75% of the cationic carbonate subunits of the cationic polymer, designated second cationic carbonate subunits, have a cationic side chain group comprising 6 to 9 carbons.

$L^a$ and $Q'(R^a)_{u'}$ of the first cationic carbonate subunits of formula (23) can individually have 3 to about 22 carbons, with the proviso that $L^a$-$Q'(R^a)_{u'}$ has a total of 10 to about 25 carbons. In an embodiment, each of the first cationic carbonate subunits of formula (23) has a cationic side chain comprising 13 to about 25 carbons, and each of the second cationic carbonate subunits has a cationic side chain comprising 6 to 12 carbons.

The cationic polymers of formula (23) can have a structure according to formula (24):

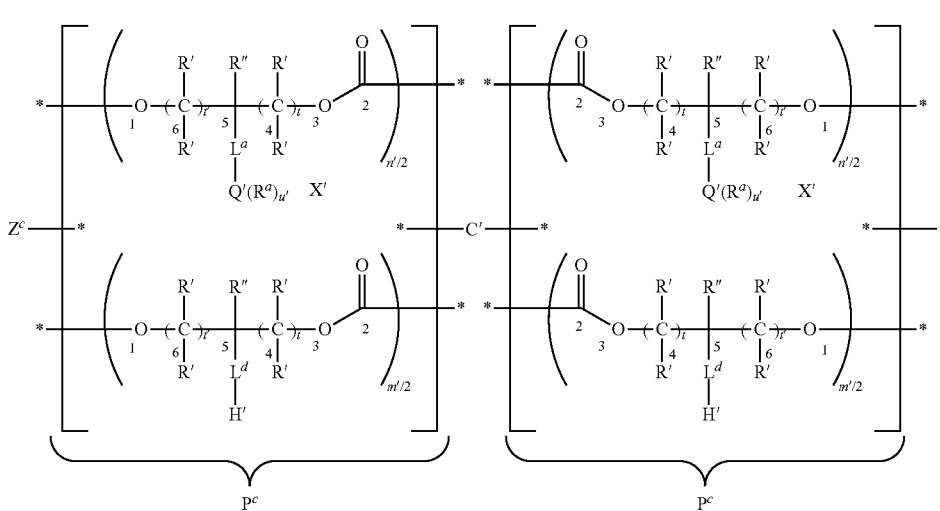

(24)

wherein n' represents the total number of cationic carbonate subunits, wherein n' has a value greater than 0, m' represents the total number of carbonate subunits, wherein m' has a value greater than 0, n'+m' has a value of about 5 to about 45, and a ratio m':n' is about 15:85 to about 0.1:99.9, C' is a $C_2$-$C_{15}$ non-polymeric divalent linking group joining polymer chains $P^c$, wherein C' comprises i) a first heteroatom linked to a first polymer chain $P^c$, wherein the first heteroatom is selected from the group consisting of nitrogen, oxygen, and sulfur, and ii) a second heteroatom linked to a second polymer chain $P^c$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each $L^d$ is an independent divalent linking group selected from the group consisting of single bond and monovalent radicals comprising 1 to about 10 carbons, each H' is an independent monovalent radical comprising a covalently bound form of a steroid and/or a vitamin compound, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;

and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (24) can individually have 3 to about 22 carbons, with the proviso that $L^a$-$Q'(R^a)_{u'}$ has a total of 10 to about 25 carbons. In an embodiment, each of the first cationic carbonate subunits of formula (24) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

H' can comprise a covalently bound form of a vitamin E compound, vitamin D compound, or combinations thereof. In an embodiment, H' comprises a covalently bound form of a vitamin compound selected from the group consisting of alpha-tocopherol (a vitamin E compound), ergocalciferol (vitamin D2), and combinations thereof.

The antimicrobial cationic polymers can have a structure in accordance with formula (25):

$$Y^c-P^b-C'-P^b-Y^d \qquad (25),$$

wherein

C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, $Y^c$ is a monovalent first end group selected from the group consisting of hydrogen, groups comprising a covalently bound form of a steroid, and groups comprising a covalently bound form of a vitamin, $Y^d$ is a monovalent second end group selected from the group consisting of hydrogen, groups comprising a covalently bound form of a steroid, and groups comprising a covalently bound form of a vitamin, each polymer chain $P^b$ consists essentially of cationic carbonate subunits, wherein i) the cationic polymer comprises a total of 5 to about 45 cationic carbonate subunits, ii) each of the cationic carbonate subunits comprises a backbone portion of the polymer chain and a cationic side chain linked to the backbone portion, and iii) the cationic side chain comprises a positive-charged heteroatom Q' of a quaternary ammonium group and/or quaternary phosphonium group, about 25% to 100% of all the cationic carbonate subunits of the cationic polymer, designated first cationic carbonate subunits, have a cationic side chain comprising 10 to about 25 carbons, and 0% to about 75% of the cationic carbonate subunits of the cationic polymer, designated second cationic carbonate subunits, have a cationic side chain comprising 6 to 9 carbons.

$L^a$ and $Q'(R^a)_{u'}$ of the first cationic carbonate subunits of formula (25) can individually have 3 to about 22 carbons, with the proviso that $L^a$-$Q'(R^a)_{u'}$ has a total of 10 to about 25 carbons. In an embodiment, each of the first cationic carbonate subunits of formula (25) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

$Y^c$ and/or $Y_d$ can comprise a covalently bound form of a steroid and/or a vitamin.

More specific cationic polymers of formula (25) have a structure according to formula (26):

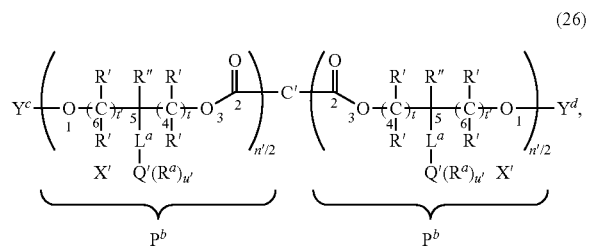

(26)

wherein n' represents the total number of cationic carbonate subunits of the cationic polymer, and has a value of about 5 to about 45, C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, the polymer chains $P^b$ consist essentially of the cationic carbonate subunits, $Y^c$ is an independent monovalent end group selected from the group consisting of hydrogen, groups comprising a covalently bound form of a steroid, and groups comprising a covalently bound form of a vitamin, $Y^d$ is an independent monovalent end group selected from the group consisting of hydrogen, groups comprising a covalently bound form of a steroid, and groups comprising a covalently bound form of a vitamin, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate subunit has t=0 and t'=0, and each X' is an independent negative-charged ion;

and wherein about 25% to 100% of the cationic carbonate subunits of the cationic polymer, designated first cationic carbonate subunits, have a cationic side chain $L^a$-$Q'(R^a)_{u'}$ comprising 10 to about 25 carbons, and 0% to about 75% of the cationic carbonate subunits of the cationic polymer, designated second cationic carbonate subunits, have a cationic side chain $L^a$-$Q'(R^a)_{u'}$ comprising 6 to 9 carbons.

$L^a$ and $Q'(R^a)_{u'}$ of the first cationic carbonate subunits of formula (26) can individually have 3 to about 22 carbons, with the proviso that $L^a$-$Q'(R^a)_{u'}$ has a total of 10 to about 25 carbons. In an embodiment, each of the first cationic carbonate subunits of formula (26) has a cationic side chain $L^a$-$Q'(R^a)_{u'}$ comprising 13 to about 25 carbons, and each of the second cationic carbonate subunits has a cationic side chain $L^a$-$Q'(R^a)_{u'}$ comprising 6 to 12 carbons.

Cation-Forming Cyclic Carbonate Monomers

A preferred method of preparing the disclosed cationic polymers utilizes a cyclic carbonate monomer capable of forming a cationic moiety before or after the polymerization. These are referred to as cation-forming monomers, which have the formula (27):

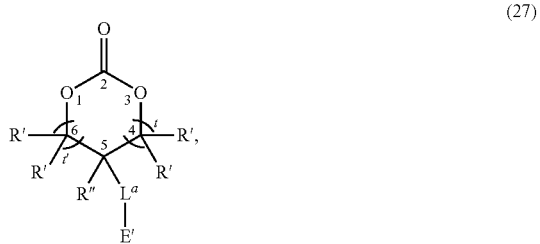

(27)

wherein the ring atoms are shown numbered 1 to 6, $L^a$ is a divalent linking group comprising at least 3 carbons, E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises 1 or more carbons, and together $Q'(R^a)_{u'}$ and $L^a$ comprise 6 to about 25 carbons, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, t is a positive integer having a value of 0 to 2, t' is a positive integer having a value of 0 to 2, and t and t' cannot both be zero.

The cation-forming monomers of formula (27) have a ring substituent $L^a$-E'. This ring substituent $L^a$-E' becomes a side chain of the initial polymer formed by the ring opening polymerization of the cation-forming monomer. E' can be an electrophilic and/or nucleophilic group so long as the side chain $L^a$-E' is capable of reacting to produce a $C_6$-$C_{25}$ cationic side chain $L^a$-Q'$(R^a)_{u'}$ of the cationic polymer. Preferably, E' is a leaving group capable of reacting with a tertiary amine to form a quaternary ammonium group, and/or reacting with a tertiary phosphine to form a quaternary phosphonium group.

The cation-forming monomers can be stereospecific or non-stereospecific.

In an embodiment, t and t' of formula (27) are each 1, each R' at carbon 4 is hydrogen, each R' at carbon 6 is hydrogen, and R" at carbon 5 is selected from the group consisting of hydrogen, methyl, and ethyl.

Ring opening polymerization of cation-forming monomers of formula (27) produces an initial polycarbonate having a subunit according to formula (28):

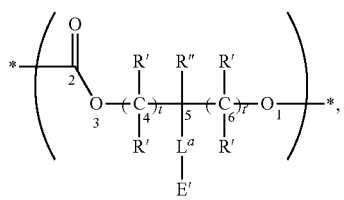

(28)

wherein
backbone atoms are shown numbered 1 to 6,
$L^a$ is a divalent linking group comprising at least 3 carbons,
E' is a substituent capable of reacting to produce a cationic moiety Q'$(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together Q'$(R^a)_{u'}$ and $L^a$ comprise 6 to about 25 carbons,
each R' is an independent monovalent radical selected from the group consisting of hydrogen, halogens, methyl, and ethyl,
R" is a monovalent radical selected from the group consisting of hydrogen, halogens, and alkyl groups comprising 1 to 6 carbons,
t is a positive integer having a value of 0 to 2,
t' is a positive integer having a value of 0 to 2, and
t and t' cannot both be zero.

More specific cation-forming monomers have the formula (29):

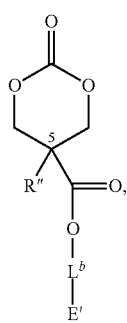

(29)

wherein
ring atom 5 is labeled,
$L^b$ is a divalent linking group comprising at least 2 carbons,
E' is a substituent capable of reacting to produce a cationic moiety Q'$(R^a)_{u'}$ linked to $L^b$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together Q'$(R^a)_{u'}$ and $L^b$ comprise 5 to about 24 carbons, and
R" is a monovalent radical selected from the group consisting of hydrogen, halogens, and alkyl groups comprising 1 to 6 carbons.

Ring opening polymerization of cation-forming monomers of formula (29) produces a polycarbonate having a subunit according to formula (30):

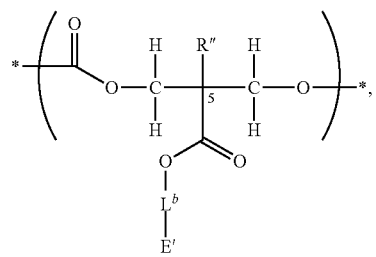

(30)

wherein
ring atom 5 is labeled,
$L^b$ is a divalent linking group comprising at least 2 carbons,
E' is a substituent capable of reacting to produce a cationic moiety Q'$(R^a)_{u'}$ linked to $L^b$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together Q'$(R^a)_{u'}$ and $L^b$ comprise 5 to about 24 carbons, and
R" is a monovalent radical selected from the group consisting of hydrogen, halogens, and alkyl groups comprising 1 to 6 carbons.

The cation-forming monomers can have the formula (31):

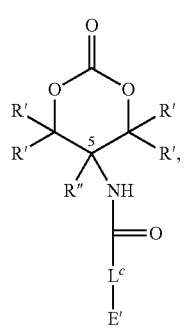

(31)

wherein
ring atom 5 is labeled,
$L^c$ is a divalent linking group comprising at least 2 carbons,
E' is a substituent capable of reacting to produce a cationic moiety Q'$(R^a)_{u'}$ linked to $L^c$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^c$ comprise 5 to about 24 carbons, each R' is an independent monovalent radical selected from the group consisting of hydrogen, halogens, methyl, and ethyl, and R" is a monovalent radical selected from the group consisting of hydrogen, halogens, and alkyl groups comprising 1 to 6 carbons.

Ring opening polymerization of cation-forming monomers of formula (31) produces an initial polycarbonate having a subunit according to formula (32):

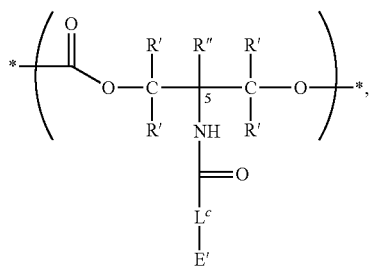

(32)

wherein ring atom 5 is labeled, $L^c$ is a divalent linking group comprising at least 2 carbons, E' is a substituent capable of reacting to produce a cationic moiety $Q'(R^a)_{u'}$ linked to $L^c$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^c$ comprise 5 to about 24 carbons, each R' is an independent monovalent radical selected from the group consisting of hydrogen, halogens, methyl, and ethyl, and R" is a monovalent radical selected from the group consisting of hydrogen, halogens, and alkyl groups comprising 1 to 6 carbons.

Exemplary cation-forming monomers include the cyclic carbonate monomers of Table 1.

TABLE 1

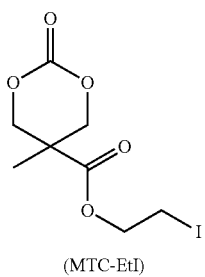

(MTC-EtI)

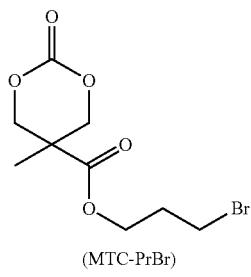

(MTC-PrBr)

TABLE 1-continued

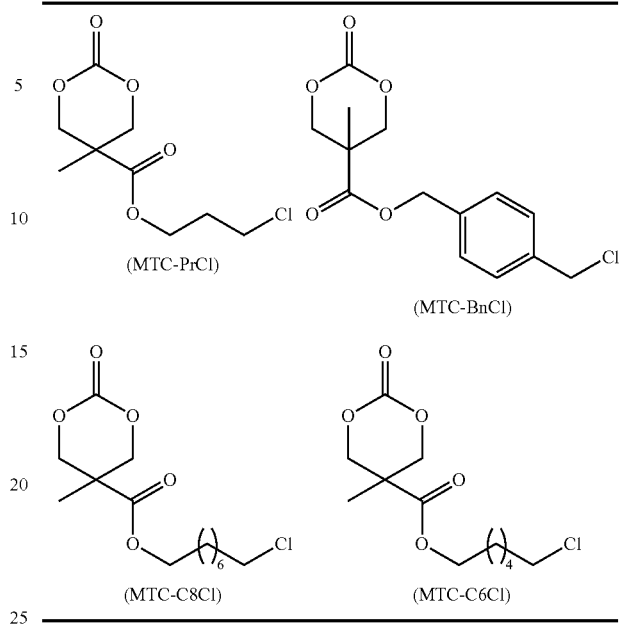

(MTC-PrCl)

(MTC-BnCl)

(MTC-C8Cl)

(MTC-C6Cl)

Ring Opening Polymerizations

The method of ring opening polymerization for forming the disclosed gel-forming block copolymers and antimicrobial cationic polymers utilizes a solvent, an organocatalyst, a nucleophilic initiator, an optional accelerator, and one or more cyclic carbonate monomers.

Using a vitamin-bearing monomer of formula (5) to illustrate a method of forming a gel-forming block copolymer of formula (1) by ring opening polymerization, a reaction mixture is formed that comprises a vitamin-bearing monomer of formula (5), a catalyst, an optional accelerator, a di-nucleophilic poly(ethylene oxide) initiator, and a solvent. Agitating the reaction mixture produces a living gel-forming block copolymer of formula (1) having terminal subunits comprising a nucleophilic group capable of initiating a ROP. Optionally, the initial gel-forming block copolymer is end capped with a suitable end capping agent.

Using a cation-forming monomer of formula (27) to illustrate a method of making the disclosed cationic polymers, a reaction mixture is formed which comprises a cyclic carbonate monomer of formula (27), a catalyst, an optional accelerator, a mono-nucleophilic ROP initiator (optionally comprising a steroid group), and a solvent. Agitating the reaction mixture forms an initial polymer. Optionally the initial polymer can be endcapped to form an endcapped initial polymer. The resulting polymer has a structure according to formula (33):

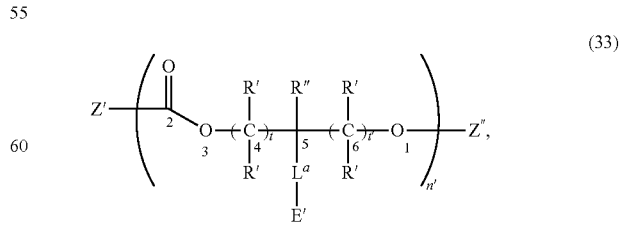

(33)

wherein n' represents the number of cationic carbonate subunits, wherein n' has a value of about 5 to about 45, Z' is a monovalent $C_1$-$C_{15}$ first end group, Z" is a monovalent second end group selected from the group consisting of hydrogen and $C_1$-$C_{15}$ moieties, $L^a$ is a divalent linking group comprising at least 3 carbons, E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises 1 or more carbons, and together $Q'(R^a)_{u'}$ and $L^a$ comprise 6 to about 25 carbons, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, and no carbonate subunit has t=0 and t'=0.

Z' can be a residue of the ROP initiator. In an embodiment, Z' is an S'-L' group comprising a steroid moiety. In this instance, each carbonate subunit of the initial polymer comprises a side chain E' group.

The living end (oxy end) of the initial polymer formed by the ROP has a reactive hydroxy group (second end group Z"=H), which is capable of initiating another ROP. The living end can be treated with an endcap agent, thereby forming a second end group Z" that is capable of preventing further chain growth and stabilizing the polymer against unwanted side reactions such as chain scission. The polymerization and endcapping can occur in the same pot without isolating the initial polymer. Endcap agents include, for example, materials for converting terminal hydroxy groups to esters, such as carboxylic acid anhydrides, carboxylic acid chlorides, and reactive esters (e.g., p-nitrophenyl esters). In an embodiment, the endcap agent is an acylating agent, and the second end group Z" is an acyl group. In another embodiment the acylating agent is acetic anhydride, and the second end group Z" is an acetyl group. In another embodiment, the endcap agent comprises a covalently bound form of a steroid group, a vitamin, or a combination thereof.

The initial polymer and/or the endcapped initial polymer can be treated chemically, thermally, and/or photochemically to convert E' to a positive-charged $Q'(R^a)_{u'}$ group, thereby forming a cationic polymer. For example, E' can be an electrophilic leaving group (e.g., chloride, bromide, iodide, sulfonate ester, and the like), which is capable of undergoing a nucleophilic displacement reaction with a Lewis base (e.g., tertiary amine, trialkyl phosphine) to form a quaternary ammonium group and/or a phosphonium group. In an embodiment, E' is chloride, bromide, and/or iodide. In another embodiment, the cyclic carbonate monomer is a compound of formula (29) and the initial polymer comprises a subunit of formula (30). In another embodiment, the cyclic carbonate monomer is a compound of formula (31) and the initial polymer comprises a subunit of formula (32).

Also contemplated is a method of forming the cationic polymer using a cationic cyclic carbonate monomer that comprises a positive-charged Q' group. In this instance, the ROP forms an initial cationic polymer having a living end unit (i.e., a nucleophilic hydroxy end group capable of initiating a subsequent ROP). The living end unit can be endcapped to prevent unwanted side reactions.

Exemplary non-limiting tertiary amines for forming quaternary amines by a nucleophilic substitution reaction with electrophilic E' groups include trimethylamine, triethylamine, tri-n-propylamine, tri-iso-propylamine, tri-n-butylamine, tri-n-pentylamine, dimethylethylamine, dimethylpropylamine, dimethyl-iso-propylamine, dimethylbutylamine, dimethylpentylamine, dimethylbenzylamine, diethylmethylamine, diethylpentylamine, diethylbutylamine, N,N-dimethylcyclohexylamine, N-methylimidazole, N-ethylimidazole, N-(n-propyl)imidazole, N-i sopropylimidazole, N-(n-butyl)imidazole, N,N-diethylcyclohexylamine, N,N-dimethylaniline, N,N-diethylaniline, pyridine, and combinations thereof.

Exemplary non-limiting tertiary phosphines for forming quaternary phosphonium groups by a nucleophilic substitution reaction with electrophilic E' groups include trimethylphosphine, triethylphosphine, tripropylphosphine, tributylphosphine, ethyldimethylphosphine, propyldimethylphosphine, butyldimethylphosphine, pentyldimethylphosphine, hexyldimethylphosphine, heptyldimethylphosphine, octyldimethylphosphine, methyldiethylphosphine, propyldiethylphosphine, butyldiethylphosphine, pentyldiethylphosphine, hexyldiethylphosphine, heptyldiethylphosphine, octyldiethylphosphine, pentyldipropylphosphine, pentyldibutylphosphine, dipentylmethylphosphine, dipentylethylphosphine, dipentylpropylphosphine, dipentylbutylphosphine, tripentylphosphine, hexyldipropylphosphine, hexyldibutylphosphine, cyclohexyl-dimethylphosphine, cyclohexyldiethylphosphine, dihexylmethylphosphine, dihexyl-ethylphosphine, dihexylpropylphosphine, benzyldimethylphosphine, and combinations thereof.

ROP Initiators

Nucleophilic initiators for ROP generally include alcohols, amines, and/or thiols.

Mononucleophilic Initiators

For the above described cationic polymers having one cationic polymer chain (on-armed cationic polymers), the ROP initiator is a mono-nucleophilic non-polymeric initiator (e.g., ethanol, n-butanol, benzyl alcohol, and the like). In some instances, the ROP initiator can comprise a covalently bound form of a biologically active compound selected from the group consisting of steroids, non-steroid hormones, vitamins, and drugs. For example, mono-nucleophilic ROP initiators include cholesterol, alpha-tocopherol, and ergocalciferol.

More specific mono-nucleophilic ROP initiators comprise a non-charged steroid group S'. The initiator can have a structure according to formula (34):

$$S'-L^e \qquad (34),$$

wherein S' is a steroid group and $L^e$ is a monovalent group comprising i) 1 to about 10 carbons and ii) a nucleophilic initiating group for the ROP. Non-limiting examples of ROP initiators of formula (34) include Chol-OPrOH:

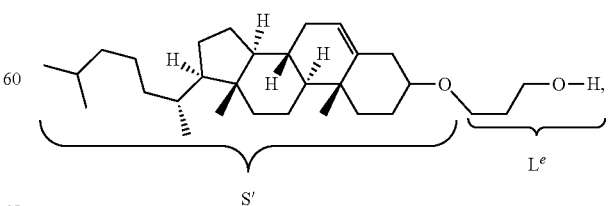

and Chol-OTEG-OH:

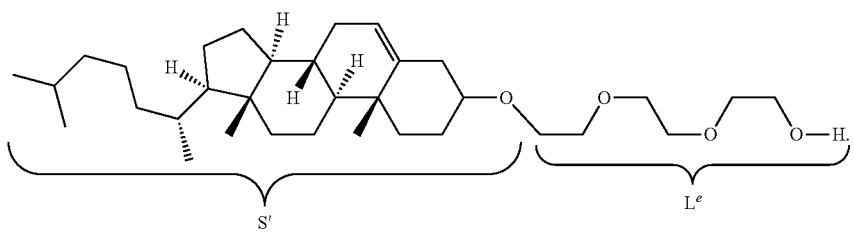

In the above examples, S' is a cholesteryl group. Using the preferred method of preparing the cationic polymers described below, the S'L'-* fragment of the cationic polymer is a residue of the ROP initiator when linked to the carbonyl end of the polycarbonate backbone. The S'-L'-* fragment derived from Chol-OPrOH has the structure:

The S'-L'-* fragment derived from Chol-OTEG-OH has the structure:

The ROP initiator can be used singularly or in combination with a different ROP initiator (e.g., initiators having different steroid groups and/or different $L^e$ groups.) The ROP initiator can be stereospecific or non-stereospecific.

Di-Nucleophilic Initiators for Two-Armed Cationic Polymers

The ROP initiator used to form the above described cationic polymers having two polymer chains (two-armed cationic polymers) is a di-nucleophilic initiator. Exemplary di-nucleophilic ROP initiators include ethylene glycol, butanediol, 1,4-benzenedimethanol, and Bn-MPA:

(Bn-MPA)

An exemplary di-nucleophilic ROP initiator comprising a steroid group is Chol-MPA:

Polyethyleneoxide Initiators for Preparing Gel-Forming Block Copolymers

The ROP initiator used to prepare gel-forming block copolymers is a di-nucleophilic poly(ethylene oxide) having a number average molecular weight (Mn) of about 5000 to about 25000, and preferably about 10,000 to about 20000. The di-nucleophilic poly(ethylene oxide) has independent terminal ROP initiating groups selected from the group consisting of amines, alcohols, thiols, and combinations thereof. Exemplary di-nucleophilic poly(ethylene oxide) initiators include the following materials:

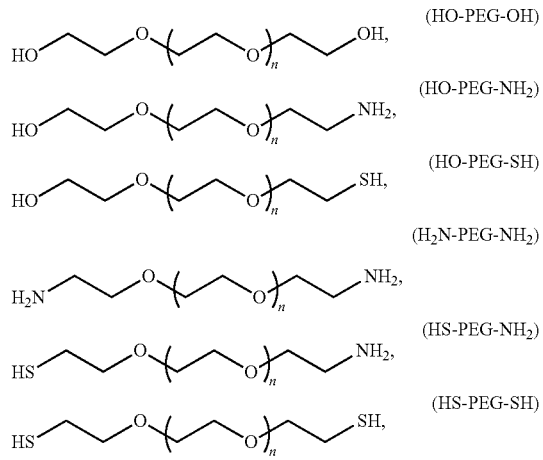

and combinations thereof.

In an embodiment the ROP initiator used to form the gel-forming block copolymer is a poly(ethylene glycol) (HO-PEG-OH), also referred to simply as PEG.

ROP Solvents

Non-limiting solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

ROP Catalysts

Less preferred catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum trimethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

Preferably, the chemical formula of the catalyst used for the ring opening polymerization does not include an ionic or nonionic form of a metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Preferred catalysts are organocatalysts whose chemical formulas contain none of the above metals. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

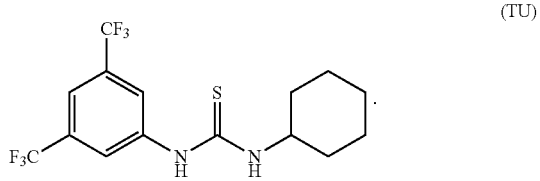 [SMILES: FC(F)(F)c1cc(NC(=S)NC2CCCCC2)cc(C(F)(F)F)c1]

Other ROP organocatalysts comprise at least one 1,1,1,3,3,3-hexafluoropropan-2-ol-2-yl (HFP) group. Singly-donating hydrogen bond catalysts have the formula (35):

$$R^2—C(CF_3)_2OH \quad (35),$$

wherein $R^2$ represents a hydrogen or a monovalent radical having 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 2.

TABLE 2

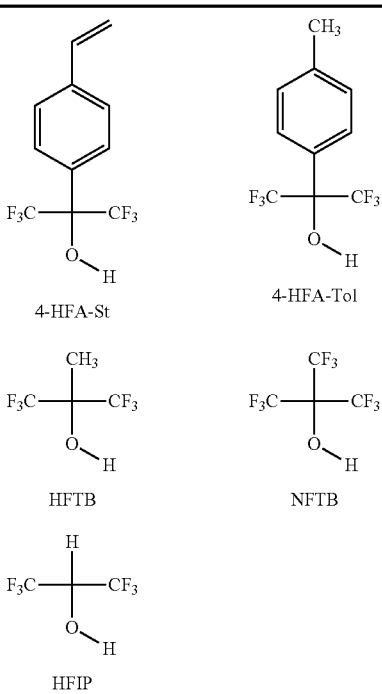

Doubly-donating hydrogen bonding catalysts have two HFP groups, represented by the formula (36):

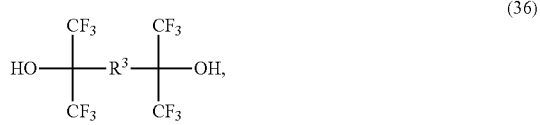

(36)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (36) include those listed in Table 3. In a specific embodiment, $R^2$ is an arylene or substituted arylene group, and the HFP groups occupy positions meta to each other on the aromatic ring.

TABLE 3

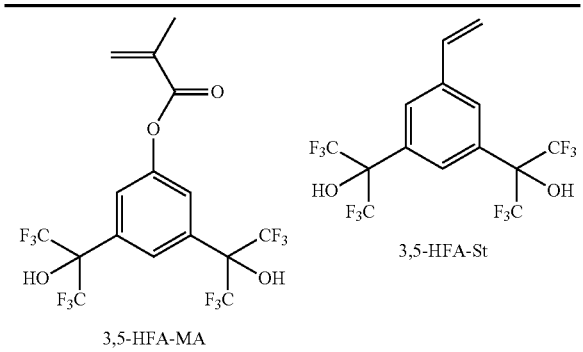

TABLE 3-continued

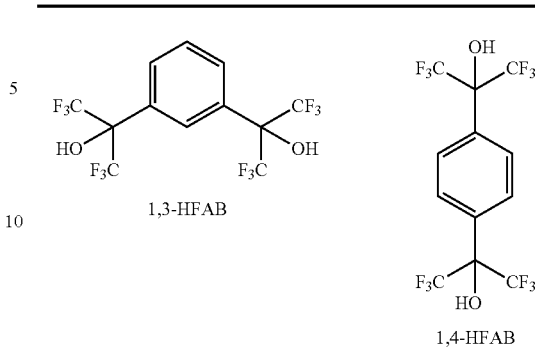

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators.

The ROP polymerization can be conducted in the presence of an optional accelerator, in particular a nitrogen base. Exemplary nitrogen base accelerators are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 4.

TABLE 4
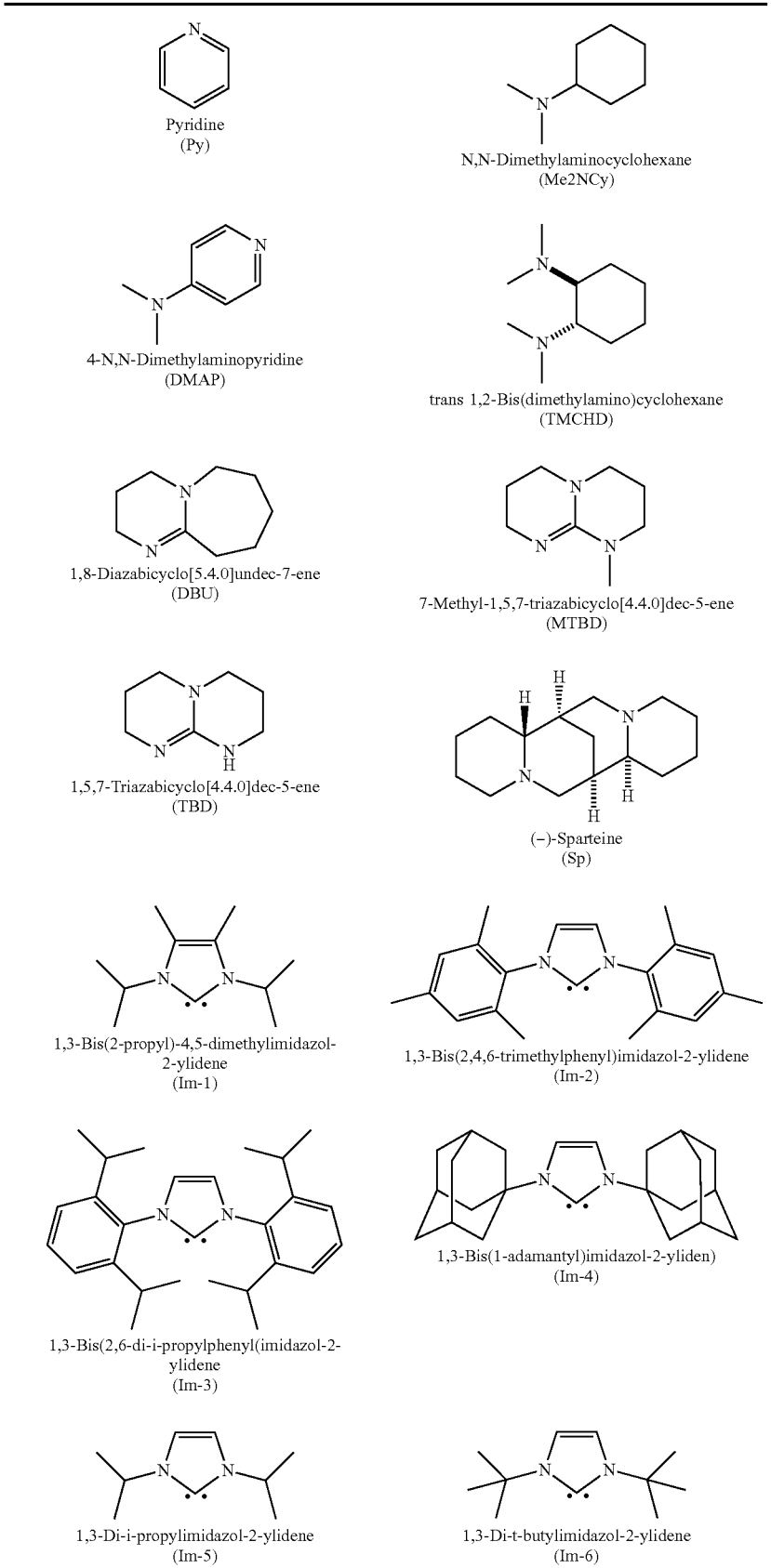

TABLE 4-continued

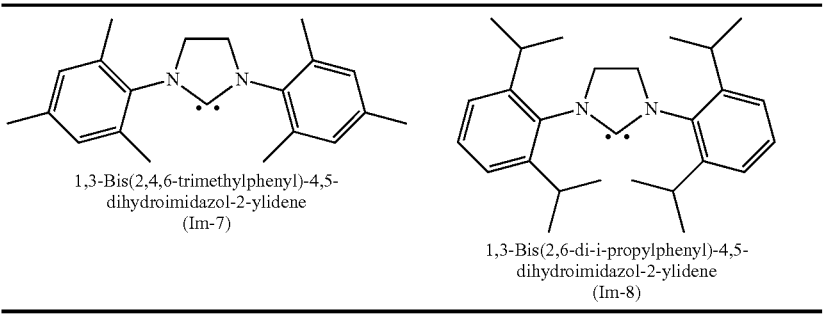

1,3-Bis(2,4,6-trimethylphenyl)-4,5-dihydroimidazol-2-ylidene
(Im-7)

1,3-Bis(2,6-di-i-propylphenyl)-4,5-dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The initiator groups are preferably present in an amount of 0.001 to 10.0 mol %, 0.1 to 2.5 mol %, 0.1 to 1.0 mol %, or 0.2 to 0.5 mol %, based on total moles of cyclic carbonyl monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on total moles of cyclic carbonate monomer.

The catalysts can be removed by selective precipitation or in the case of the solid supported catalysts, simply by filtration. The catalyst can be present in an amount of 0 wt % (weight percent) to about 20 wt %, preferably 0 wt % (weight percent) to about 0.5 wt % based on the total weight of the cationic oligomer and the residual catalyst. The cationic oligomer preferably comprises no residual catalyst.

The ring-opening polymerization can be performed at a temperature that is about ambient temperature or higher, more specifically 15° C. to 200° C., and even more specifically 20° C. to 80° C. Reaction times vary with solvent, temperature, agitation rate, pressure, and equipment, but in general the polymerizations are complete within 1 to 100 hours.

The ROP polymerization is conducted under an inert (i.e., dry) atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

Average Molecular Weight.

The gel-forming block copolymers can have a number average molecular weight (Mn) as determined by size exclusion chromatography of about 5500 to about 55000.

The cationic polymers have a number average molecular weight (Mn) as determined by size exclusion chromatography of about 1500 to about 50,000, more specifically about 1500 to about 30,000. The precursor polymer to the cationic polymer and/or the cationic polymer preferably can have a polydispersity index (PDI) of 1.01 to about 2.0, more particularly 1.01 to 1.30, and even more particularly 1.01 to 1.25.

In some instances the cationic polymers alone can self-assemble into nanoparticulate micelles in de-ionized water. The cationic polymers can have a critical micelle concentration (CMC) of about 15 mg/L to about 45 mg/L. The micelles can have a minimum inhibitory concentration (MIC) for microbial growth of about 7 mg/L to about 500 mg/L. In some instances, the MIC is below the CMC, meaning the antimicrobial activity is not dependent on self-assembly of the cationic polymers.

In general, cationic polymers having a DP of 5 to about 45 in which greater than 75% of the side chain $L^a$-$Q'(R^a)_{u'}$ groups of the cationic carbonate subunits contained 8 carbons or less were weakly active against Gram-negative and/or Gram-positive microbes and fungi. Moreover, at low DP (<10) the HC50 and/or HC20 values of the cationic polymers generally fell below 500 mg/L, indicating a trend toward biocidal properties. Higher HC50 and/or HC20 values (500 mg/L or higher) were generally favored by a DP of about 10 to about 45. The examples further below also show that when at least 25% of the side chain groups of the cationic carbonate subunits contained 13 or more carbons and the DP was about 10 to about 30, the cationic polymers were highly active (MIC<500 mg/L) against both Gram-negative and Gram-positive microbes and fungi, and had HC50 values of 500 mg/L or higher. Increased inhibition efficacy and lower red blood cell toxicity (higher HC50 values) were obtained using a steroid end group Z'. Hemolytic selectivity (HC50/MIC) also rose. The groups Z', Z", $Z^c$, and C' can be used to further adjust antimicrobial activity, hemolytic selectivity, or to provide a secondary function (e.g., cell recognition capability, enhancement of cell membrane permeability, and so on).

Moreover, 10 mol % or less of carbonate subunits comprising an alpha-tocopheryl(a vitamin E compound) and/or an ergocalciferyl (vitamin D2) side chain moiety was also effective in lowering MIC (i.e., increasing toxicity to microbes) and/or increasing HC50 values (lowering toxicity to mammalian red blood cells) when 25% to 100% of the cationic carbonate subunits comprised 10 to 25 carbons.

Also disclosed is an antimicrobial drug composition comprising a solvent, about 4 wt. % to about 10 wt. % of a gel-forming block copolymer, and about 0.0001 wt. % to about 10 wt. % of an antimicrobial cationic polymer, wherein weight percent (wt. %) is based on total weight of the drug composition, the drug composition is a gel formed by noncovalent interactions of polymer chains of the block copolymer in the solvent, and the antimicrobial cationic polymer is contained in the gel. The antimicrobial cationic polymer can be present in the gel in the form of non-associated polymer chains, self-assembled particles (e.g., micelles), and/or other complexes formed by noncovalent interactions.

Another antimicrobial drug composition comprises a solvent, about 4 wt. % to about 10 wt. % of a gel-forming block copolymer, and about 0.0001 wt. % to about 10 wt. % of an antimicrobial cationic polymer (first drug), and about 0.0001 wt. % to about 10 wt. % an antimicrobial compound (second drug); wherein weight percent (wt. %) is based on total weight of the drug composition, the drug composition is a gel formed by noncovalent interactions of polymer chains of the block copolymer in the solvent, and the first drug and the second drug are contained in the gel, associated by noncovalent interactions. The examples below show that combinations of this type can exhibit significant synergistic enhancement in toxicity to microbes compared to the same composition lacking the antimicrobial cationic polymer or the antimicrobial drug compound when tested under otherwise identical conditions.

Also disclosed is an antimicrobial aqueous solution for killing a microbe. The solution comprises about 0.0001 wt. % to about 10 wt. % of an antimicrobial cationic polycarbonate (first drug) and about 0.0001 wt. % to about 10 wt. % of an antimicrobial compound (second drug), wherein weight percent (wt. %) is based on total weight of the aqueous solution. The first drug and the second drug are associated by noncovalent interactions in the aqueous solution. In an embodiment, the antimicrobial compound (second drug) is fluconazole, doxycycline, or combinations thereof. The examples below show that these combinations also can exhibit synergistic enhancement in toxicity to microbes compared to the same composition lacking either the antimicrobial cationic polymer or the antimicrobial compound when tested under otherwise identical conditions. The antimicrobial aqueous solution can be suitable for eradicating a microbial biofilm.

Further disclosed is a method of killing a microbe, comprising contacting a microbe with any of the foregoing antimicrobial compositions.

Exemplary microbes include *Staphylococcus epidermidis* (*S. epidermidis*), *Staphylococcus aureus* (*S. aureus*), *Escherichia coli* (*E. coli*), *Pseudomonas aeruginosa* (*P. aeruginosa*), *Candida albicans* (*C. albicans*), Methicillin-resistant *Staphylococcus aureus* (MRSA), Vancomycin-resistant *Enterococcus* (VRE), *Acinetobacter baumannii* (*A. baumannii*), *Cryptococcus neoformans* (*C. neoformans*), and *Klebsiella pneumoniae* (*K. pneumoniae*).

Additionally disclosed is a method of treating a cancer, comprising performing a in vivo depot injection of a gel composition near or in contact with a tumor, thereby inhibiting growth of the tumor. The gel composition comprises a solvent, a disclosed gel-forming block copolymer, and an anti-tumor agent. In an embodiment, the anti-tumor agent is a monoclonal antibody. In another embodiment, the anti-tumor agent is herceptin.

For the examples below, the following definitions are applicable.

HC50 is defined as the concentration (in mg/L) of cationic polymer that causes 50% of mammalian red blood cells to undergo hemolysis. HC50 values of 500 mg/L or higher are desirable.

HC20 is defined as the concentration (in mg/L) of cationic polymer that causes 20% of mammalian red blood cells to undergo hemolysis. HC20 values of 500 mg/L or higher are desirable.

Minimum inhibitory concentration (MIC) is defined as the minimum concentration (in mg/L) of cationic polymer required to inhibit growth of a given microbe for a twenty-four period. An MIC less than 500 mg/L is desirable. Even more desirable is a MIC of 250 mg/L or less. A lower MIC indicates higher antimicrobial activity.

Minimum bactericidal concentration (MBC) is defined as the minimum concentration (in mg/L) of cationic polymer required to kill a given microbe. A lower MBC indicates higher antimicrobial activity.

HC50 selectivity is defined as the ratio of HC50/MIC. An HC50 selectivity of 4 or more is desirable. Higher HC50 selectivity values indicate more activity against microbial cells and less toxicity to mammalian cells. Likewise, HC20 selectivity is defined as the ratio of HC20/MIC. An HC20 selectivity of 4 or more is desirable.

The examples further below demonstrate that the gel-forming triblock copolymers have a large payload-carrying capacity and tunable release properties, enabling numerous pharmaceutical-driven applications. In some examples the hydrogels were mixed with an antimicrobial cationic polycarbonate and/or molecular antibiotic drug, conferring antimicrobial activity to the hydrogel and/or providing controlled release of the cationic polycarbonate and/or molecular antibiotic drugs. Synergistic enhancement using combinations of antimicrobial cationic polycarbonate and molecular antibiotic were observed. In other examples, anti-cancer agents were incorporated into hydrogels and delivered by depot injection, which show potent in vivo selective toxicity against tumor cells.

EXAMPLES

Materials used in the following examples are listed in Table 5.

TABLE 5

| ABBREVIATION | DESCRIPTION | SUPPLIER |
|---|---|---|
| | Alpha-Tocopherol | Alfa Aesar |
| | Sodium Nicotinate | Alfa Aesar |
| | Herceptin (Mw: 145.5 kDa) | Roche, Switzerland |
| MTT | 3-[4,5-Dimethylthiazol-2-yl]-2,5-Diphenyl Tetrazolium Bromide | Sigma-Aldrich |
| PBS | Phosphate-Buffered Saline (PBS, pH 7.4) | 1$^{st}$ Base |
| | KOLLIPHOR RH40; PEG-40 hydrogenated castor oil; derived from hydrogenated castor oil and ethylene oxide, | Sigma-Aldrich |
| TMA | Trimethylamine | Sigma-Aldrich |
| MeIm | Methyl Imidazole | Sigma-Aldrich |
| EtIm | Ethyl Imidazole | Sigma-Aldrich |
| Fluc | Fluconazole | Sigma-Aldrich |
| DXY | Doxycycline | Sigma-Aldrich |
| HDF | Human dermal fibroblasts | Sigma-Aldrich |
| HO-PEG-OH | Poly(ethylene glycol), Mn 10 kDa or 20 kDa | Sigma-Aldrich |

Herein, Mn is the number average molecular weight, Mw is the weight average molecular weight, and MW is the molecular weight of one molecule.

A p-value is the probability of obtaining a test statistic at least as extreme as the one that was actually observed, assuming that the null hypothesis is true. The lower the p-value, the less likely the result is if the null hypothesis is true, and consequently the more "significant" the result is, in the sense of statistical significance. The null hypothesis is oftentimes rejected when the p-value is less than the significance level a (Greek alpha), which is often 0.05 or 0.01. P-values are reported below simply as "P".

Apoptosis refers to the death of cells which occurs as a normal and controlled part of an organism's growth or development process. Biochemical events lead to characteristic cell changes (morphology) and death. These changes include blebbing, loss of cell membrane asymmetry and attachment, cell shrinkage, nuclear fragmentation, chromatin condensation, and chromosomal DNA fragmentation.

Unless indicated otherwise, materials were purchased from Sigma-Aldrich, TCI or Merck. All solvents were of analytical grade, purchased from Fisher Scientific or J. T. Baker and used as received. Before transferring into the glove box, monomers and other reagents (e.g., initiator, monomer, etc.) were dried extensively by freeze-drying under high vacuum.

N-bis(3,5-trifluoromethyl)phenyl-N'-cyclohexylthiourea (TU) was prepared as reported by R. C. Pratt, et al., Macromolecules, 2006, 39 (23), 7863-7871, and dried by stirring in dry THF over $CaH_2$, filtering, and removing solvent under vacuum.

1,8-Diazabicyclo[5,4,0]undec-7-ene (DBU) was stirred over $CaH_2$ and vacuum distilled before being transferred to a glove box.

Human dermal fibroblasts were cultured in RPMI1640 medium. All culture media were supplemented with 10% fetal calf serum, 100 U/ml penicillin and 100 micrograms/mL streptomycin (HyClone, U.S.A.). MTT was dissolved in phosphate-buffered saline (PBS, pH 7.4) with a concentration of 5 mg/mL, and the solution was filtered with a 0.22 micrometer filter to remove blue formazan crystals prior to use.

Nuclear Magnetic Resonance (NMR) Spectroscopy

The $^1H$— and $^{13}C$-NMR spectra of monomers and polymers were recorded using a Bruker Avance 400 spectrometer, and operated at 400 and 100 MHz respectively, with the solvent proton signal as the internal reference standard.

Molecular Weight Determination by Size Exclusion Chromatography (SEC)

SEC was conducted using tetrahydrofuran (THF) as the eluent for monitoring the polymer conversion and also for the determination of polystyrene equivalent molecular weights of the macro-transfer agents. THF-SEC was recorded on a Waters 2695D (Waters Corporation, U.S.A.) Separation Module equipped with an Optilab rEX differential refractometer (Wyatt Technology Corporation, U.S.A.) and Waters HR-4E as well as HR 1 columns (Waters Corporation, U.S.A.). The system was equilibrated at 30° C. in THF, which served as the polymer solvent and eluent with a flow rate of 1.0 mL/min. Polymer solutions were prepared at a known concentration (ca. 3 mg/mL) and an injection volume of 100 microliters was used. Data collection and analysis were performed using the Astra software (Wyatt Technology Corporation, U.S.A.; version 5.3.4.14). The columns were calibrated with series of polystyrene standards ranging from Mp=360 Da to Mp=778 kDa (Polymer Standard Service, U.S.A.).

Rheological Experiments

Hydrogels and organogels of known concentrations (4 to 8 wt. %) were prepared by dissolving the copolymers in deionized (DI) water at 25° C. The rheological analysis of the hydrogels was performed on an ARES-G2 rheometer (TA Instruments, USA) equipped with a plate-plate geometry of 8 mm diameter. Measurements were taken by equilibrating the gels at 25° C. between the plates at a gap of 1.0 mm. The data were collected under controlled strain of 0.2% and a frequency scan of 1.0 to 100 radians/second. Gelation properties of the polymer suspension was monitored by measuring the shear storage modulus (G') and the loss modulus (G") at each point. For shear-thinning studies, the viscosity of the hydrogels was monitored as function of shear rate from 0.1 to 10 $sec^{-1}$.

Scanning Electron Microscope (SEM) Imaging of Hydrogel

To minimize morphological perturbations, the hydrogels were cryo-fixed by transferring the sample into a chamber filled with liquid nitrogen. A day of freeze-drying process was then followed. The morphology of the gel was observed using SEM (Jeol JSM-7400F, Japan).

I. Preparation of Monomers

Preparation of MTC-OH (MW 160.1).

MTC-OH can be prepared by the method of R. C. Pratt, et al., Chemical Communications, 2008, 114-116.

Preparation of MTC-C6H5 (MW 326.2).

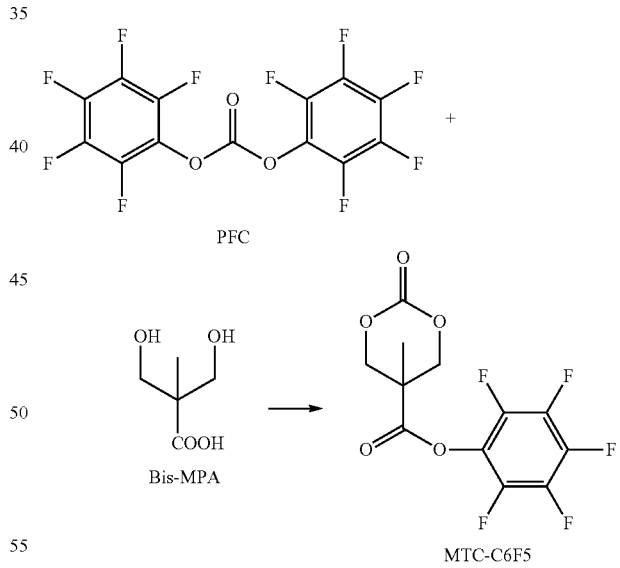

A 100 mL round bottom flask was charged with bis-MPA, (7), (5.00 g, 37 mmol, MW 134.1), bis-(pentafluorophenyl) carbonate (PFC, 31.00 g, 78 mmol, MW 394.1), and CsF (2.5 g, 16.4 mmol) rinsed with 70 mls of tetrahydrofuran (THF). Initially the reaction was heterogeneous, but after one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}$F NMR of pentafluorophenol and a single peak in the GCMS with a mass of 184. The filtrate was extracted with sodium bicarbonate, water and was dried with MgSO$_4$. The solvent was evaporated in vacuo and the product was recrystallized (ethyl acetate/hexane mixture) to give MTC-C6F5 as a white crystalline powder. The GCMS had a single peak with mass of 326 g/mol. The calculated molecular weight for $C_{12}H_7F_5O_5$ was consistent with the assigned structure. $^1$H-NMR (400 MHz in CDCl$_3$): delta 4.85 (d, J=10.8 Hz, 2H, CH$_a$H$_b$), 4.85 (d, J=10.8 Hz, 2H, CH$_a$H$_b$), 1.55 (s, 3H, CCH$_3$).

Preparation of MTC-BnCl (MW 298.7).

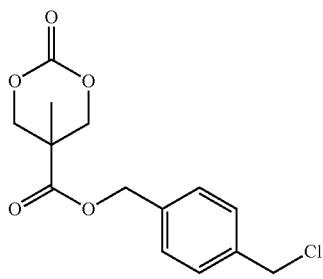

MTC-BnCl

A flask was charged with MTC-C6F5 (10 g, 30.6 mmol), p-chloromethyl benzyl alcohol (4.8 g, 30.6 mmol), PROTON SPONGE (2 g, 9.3 mmol) and THF (30 mL). The reaction mixture was stirred for 12 hours then added directly to a silica gel column. The product was isolated using diethyl ether as the eluent to yield 7.45 g (81%) white crystalline powder.

Preparation of MTC-PrCl (MW 236.65).

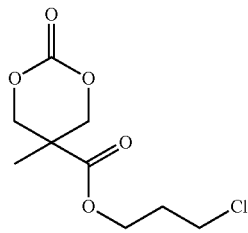

MTC-PrCl

MTCOH (8.82 g, 55 mmol) was converted to MTCOCl using standard procedures with oxalyl chloride. In a dry 250 mL round bottom flask equipped with a stir bar, the formed intermediate was dissolved in 150 mL of dry methylene chloride. Under nitrogen flow an addition funnel was attached in which 3-chloropropanol (4.94 g, 4.36 mL, 52.25 mmol), pyridine (3.95 g, 4.04 mL, 55 mmol), and 50 mL of dry methylene chloride was charged. The flask was cooled to 0° C. using an ice bath and the top solution was added drop wise during a period of 30 minutes. The formed solution was stirred for an additional 30 minutes before the ice bath was removed and the solution was stirred for an additional 16 hours under nitrogen. The crude product MTC-PrCl was directly applied onto a silica gel column and the product was separated by eluting with 100% methylene chloride. The product fractions were removed and the solvent was evaporated, yielding the product as off-white oil, which crystallized upon standing. Yield 11 g (85%). $^1$H-NMR (CDCl$_3$) delta: 4.63 (d, 2H, CH$_2$), 4.32 (t, 2H, CH$_2$), 4.16 (d, 2H, CH$_2$), 3.55 (t, 2H, CH$_2$), 2.09 (m, 2H, CH$_2$), 1.25 (s, 3H, CH$_3$).

Preparation of 5-methyl-5-(3-bromopropyl)oxycarboxyl-1,3-dioxan-2-one, (MTC-PrBr), (MW 281.10).

MTC-PrBr

MTCOPrBr was prepared by the procedure for MTCO-PrCl on a 45 mmol scale using 3-bromo-1-propanol as the alcohol. The product was purified by column chromatography, and subsequently recrystallized to yield white crystals (6.3 g, 49%). $^1$H NMR (400 MHz, CDCl$_3$): delta 4.69 (d, 2H; CH$_2$OCOO), 4.37 (t, 2H; OCH$_2$), 4.21 (d, 2H; CH$_2$OCOO), 3.45 (t, 2H; CH$_2$Br), 2.23 (m, 2H; CH$_2$), 1.33 (s, 3H; CH$_3$). $^{13}$C NMR (100 MHz, CDCl$_3$): delta 171.0, 147.3, 72.9, 63.9, 40.2, 31.0, 28.9, 17.3.

Preparation of MTC-VitE Monomer.

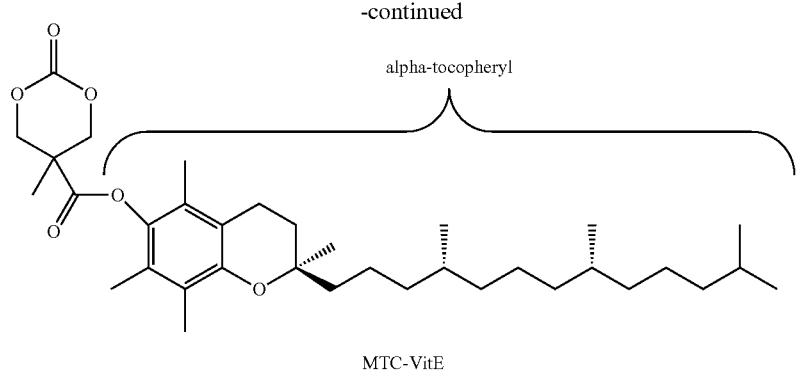

MTC-VitE

MTC-OH (3.08 g, 19.3 mmol) was dissolved in anhydrous THF (50 mL) with a few drops of DMF. Oxalyl chloride (3.3 mL, 39.4 mmol) was then added dropwise and the reaction mixture stirred under a flow of nitrogen for 1 hour before volatiles were removed under vacuum. The resultant off-white solid was heated to 65° C. for 2-3 minutes to remove any residual reagent and solvent to give the acyl chloride intermediate, MTC-Cl. The solid was redissolved in dry dichloromethane (50 mL) and chilled to 0° C. using an ice bath. A solution of alpha-tocopherol (8.30 g, 19.3 mmol) and dry triethylamine (3 mL, 21.6 mmol) in dry dichloromethane (50 mL) was subsequently added dropwise over 30 min. The mixture was allowed to warm up to ambient temperature and stirred for an additional 18 hours. A crude solid was obtained after removal of solvent, and was subjected to purification by column chromatography using silica gel. Hexane was initially used as the eluent before gently increasing the polarity to finally end with 50% ethyl acetate. A second chromatography separation was carried out using dichloromethane/ethyl acetate (4:1) in order to obtain the desired product in high purity as a white solid (6.05 g, 53%). $^1$H NMR (400 MHz, CDCl$_3$): delta 4.92 (d, 2H, J=10.8 Hz, MTC-CH$_2$), 4.34 (d, 2H, J=10.8 Hz, MTC-CH$_2$), 2.59 (d, 2H, J=6.7 Hz, tetrahydropyrano-CH$_2$), 2.09 (s, 3H, Ar—CH$_3$), 2.00 (s, 3H, Ar—CH$_3$), 1.96 (s, 3H, ArCH$_3$), 1.70-1.90 (m, 2H), 1.00-1.60 (overlapping peaks, 27H), 0.80-0.90 (m, 12H, 4×CH$_3$ on hydrophobic tail).

II. Preparation of Cationic Polymers

Examples 1 to 8

Random cationic copolymers were prepared using MTC-PrBr and MTC-BnCl precursors for the cationic subunits, MTC-VitE as the hydrophobic comonomer, benzyl alcohol (BnOH) initiator, and DBU/thiourea as catalysts. Quaternization was performed with trimethylamine. The reaction sequence is shown in Scheme 1.

Scheme 1.

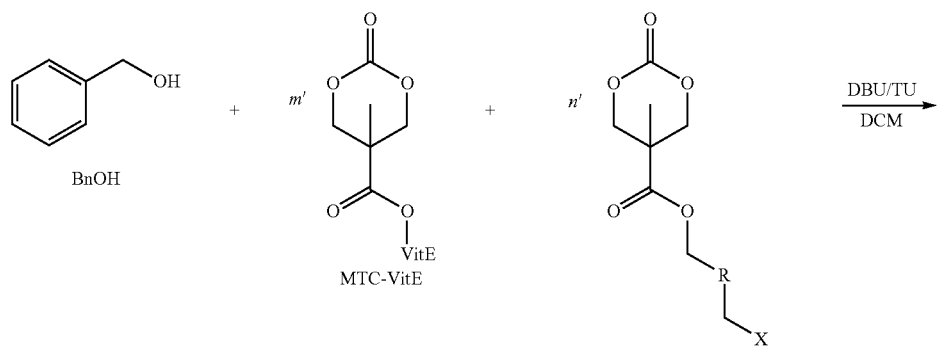

(1) R = CH$_2$; X = Br MTC-PrBr
(2) R = C$_6$H$_4$; X = Cl MTC-BnCl

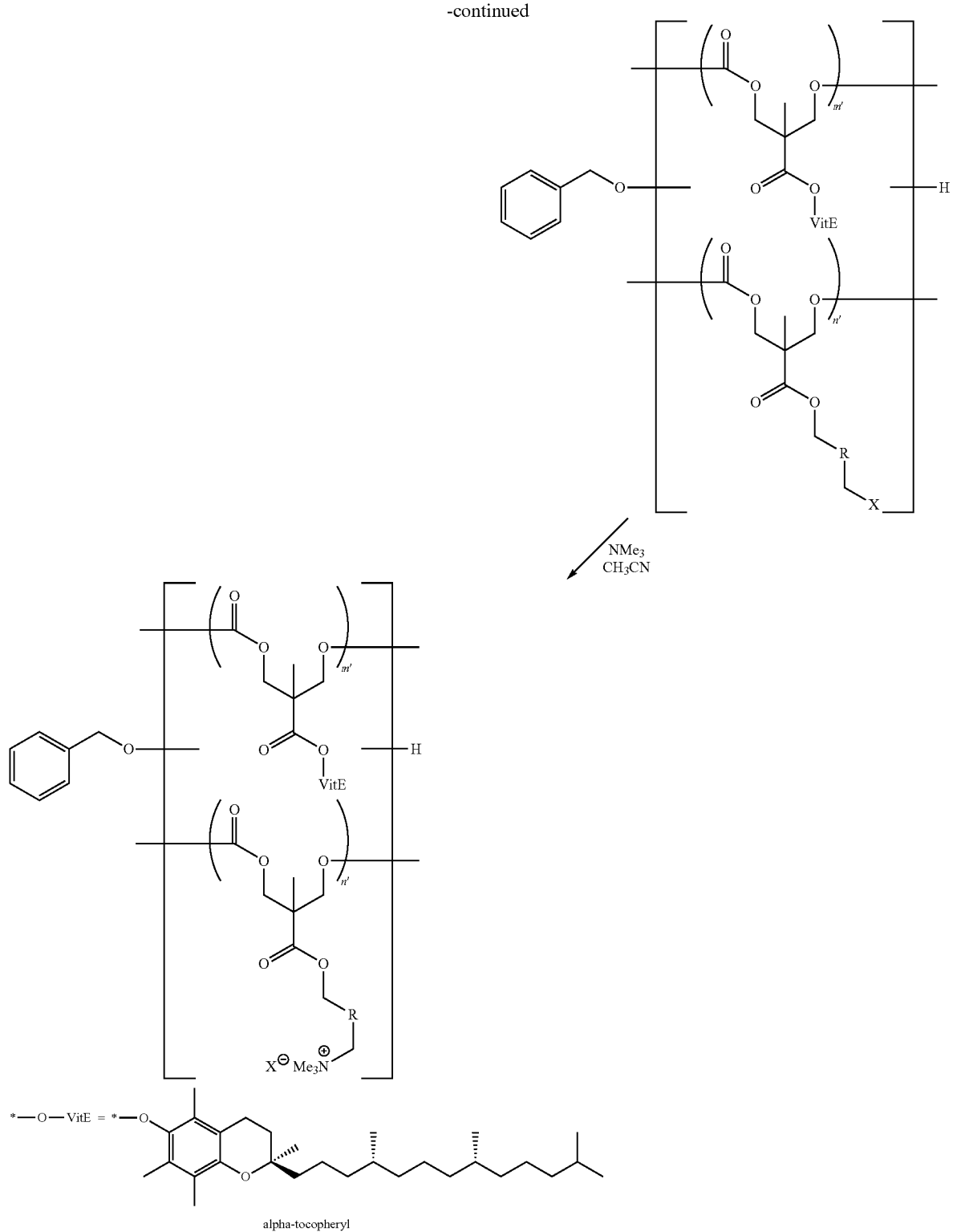

*—O—VitE = alpha-tocopheryl

The preparation of cationic polymer VE/BnCl (1:30) (i.e., m':n' is 1:30) is representative. In a 20 mL vial containing a magnetic stir bar in the glove box, MTC-BnCl (608.8 mg, 2.04 mmol, 30 equiv.), MTC-VitE (40.0 mg, 68 micromoles, 1.0 equiv.) and TU (25.2 mg, 68 micromoles, 1.0 equiv.) were dissolved in dichloromethane (3 mL). To this solution, benzyl alcohol (BnOH) (7.0 microliters, 68 micromoles, 1.0 equiv.) followed by DBU (10.2 microliters, 68 micromoles, 1.0 equiv.) were added to initiate polymerization. The reaction mixture was stirred at room temperature for 20 minutes and quenched by the addition of excess (~20 mg) of benzoic acid. The mixture was then precipitated into ice-cold methanol (50 mL) and centrifuged at −5° C. for 30 minutes. The resultant semi-transparent oil was dried under vacuum until a foamy white solid was obtained. GPC analysis of the intermediate was carried out and the polymer was used without further purification. The polymer was subsequently dissolved in acetonitrile, transferred to a Teflon-plug sealable tube and chilled to 0° C. Trimethylamine was added to start the quaternization process. The reaction mixture was stirred at room temperature for 18 hours in the sealed tube. Precipitation of an oily material was observed during the course of reaction. The mixture was evacuated to dryness under vacuum and freeze-dried to finally yield a white crisp-foamy solid. The final polymer is characterized by 1H NMR to determine the final composition and purity.

The polymerizations to form the cationic polymers was generally efficient and gave moderately high yields. In the case of MTC-BnCl, the reaction was quenched within 30 minutes. MTC-PrBr reactions typically required up to 4 hours. All pre-quaternized polymers were subjected to GPC analysis and all of them were unimodal with PDI<1.3, indicating well-controlled polymerization. Proton NMR analysis of the final quaternized polymers was also consistent with the formulations.

Table 6 lists the cationic random copolymers prepared with MTC-VitE and BnOH initiator, their degree of polymerization (DP), quaternizing agent, CMC, and the total number of carbons of each cationic subunit. For each polymer in Table 6, m'=1.

TABLE 6

| Ex. | Cationic Polymer | Initiator | Endcap[a] | Monomer 1/ Monomer 2 | Feed Mole Ratio | $DP^c$ (m':n') | Quaternizing agent | $CMC^b$ (mg/L) |
|---|---|---|---|---|---|---|---|---|
| 1 | VE/PrBr(1:15) | BnOH | None | MTC-VitE/ MTC-PrBr | 1:15 | 1:11 | TMA | N.D. |
| 2 | VE/PrBr(1:30) | BnOH | None | MTC-VitE/ MTC-PrBr | 1:30 | 1:20 | TMA | 105 |
| 3 | VE/PrBr(1:45) | BnOH | None | MTC-VitE/ MTC-PrBr | 1:45 | 1:35 | TMA | N.D. |
| 4 | VE/PrBr(1:30)/MeIm | BnOH | None | MTC-VitE/ MTC-PrBr | 1:30 | 1:24 | MeIm | N.D. |
| 5 | VE/PrBr(1:30)/EtIm | BnOH | None | MTC-VitE/ MTC-PrBr | 1:30 | 1:24 | EtIm | 52 |
| 6 | VE/BnCl(1:10) | BnOH | None | MTC-VitE/ MTC-BnCl | 1:10 | 1:8 | TMA | N.D. |
| 7 | VE/BnCl(1:20) | BnOH | None | MTC-VitE/ MTC-BnCl | 1:20 | 1:16 | TMA | N.D. |
| 8 | VE/BnCl(1:30) | BnOH | None | MTC-VitE/ MTC-BnC | 1:30 | 1:23 | TMA | N.D. |

[a]"None" means the terminal hydroxy group of the polycarbonate chain was not protected.
[b]N.D. means not determined.
[c]Actual, as determined by $^1$H NMR analysis Table 7 lists the analytical properties of the cationic random copolymers prepared using MTC-VitE.

TABLE 7

| Ex. | Cationic Polymer | Monomer 1/ Monomer 2 | Selected $^1$H NMR peaks (intensity) | Added ratio | Actual ratio | $GPC^a$ |
|---|---|---|---|---|---|---|
| 1 | VE/PrBr(1:15) | MTC-VitE/ MTC-PrBr | 7.10-7.60 (br, 5H, initiator Ph), 5.15 (br, 2H, initiator CH$_2$Ph), 4.00-4.50 (m, 66H) 3.55 (m, 22H), 3.30-3.20 (m, 99H, N(CH$_3$)), 2.10 (m, 22H), 1.00-2.00 (overlapping peaks, VitE), 0.70-0.90 (m, 12H, overlapping CH$_3$ on VitE) | 1:15 | 1:11 | 1.15 |
| 2 | VE/PrBr(1:30) | MTC-VitE/ MTC-PrBr | 7.10-7.60 (m, 5H, initiator Ph), 5.15 (m, 2H, initiator CH$_2$Ph), 4.00-4.50 (m, 120H), 3.46 (m, 40H), 3.30-3.20 (m, 180H, N(CH$_3$)), 2.10 (m, 40H), 1.00-2.00 (overlapping peaks, VitE), 0.70-0.90 (m, 12H, overlapping CH$_3$ on VitE) | 1:30 | 1:20 | 1.13 |
| 3 | VE/PrBr(1:45) | MTC-VitE/ MTC-PrBr | 7.10-7.60 (m, 5H, initiator Ph), 5.15 (m, 2H, initiator CH$_2$Ph), 4.00-4.50 (m, 120H), 3.46 (m, 70H), 3.30-3.20 (m, 315H, N(CH$_3$)), 2.10 (m, 70H), 1.00-2.00 (overlapping peaks, VitE), 0.70-0.90 (m, 12H, overlapping CH$_3$ on VitE) | 1:45 | 1:35 | 1.21 |
| 4 | VE/PrBr(1:30)/ MeIm | MTC-VitE/ MTC-PrBr | 9.00-9.50 (m, 24H, C—H Imdz), 7.50-8.00 (m, 48H, CH=CH Imdz), 4.00-4.50 (m, 192H, overlapping peaks), 3.80-4.00 (m, 72H, CH$_3$ Imdz), 2.20 (m, 48H), 1.00-2.00 (overlapping peaks, VitE), 0.80- | 1:30 | 1:24 | 1.22 |

TABLE 7-continued

| Ex. | Cationic Polymer | Monomer 1/ Monomer 2 | Selected ¹H NMR peaks (intensity) | Added ratio | Actual ratio | GPC[a] |
|---|---|---|---|---|---|---|
|  |  |  | 0.90 (m, 12H, overlapping CH₃ on VitE) |  |  |  |
| 5 | VE/PrBr(1:30)/ EtIm | MTC-VitE/ MTC-PrBr | 9.00-9.50 (m, 24H, C—H Imdz), 7.70-8.00 (m, 48H, CH=CH Imdz), 4.00-4.50 (m, 240H, overlapping peaks), 2.20 (m, 48H), 1.45 (t, 72H, CH₃ Imdz), 1.00-2.00 (overlapping peaks, VitE), 0.80-0.90 (m, 12H, overlapping CH₃ on VitE) | 1:30 | 1:24 | 1.22 |
| 6 | VE/BnCl(1:10) | MTC-VitE/ MTC-BnCl | 7.10-7.60 (m, 40H, overlapping peaks of initiator Ph and Bn), 5.00-5.40 (m, 18H, overlapping peaks of initiator CH₂Ph and Bn), 4.60 (m, 16H), 4.28 (m, 32H), 3.06 (m, 72H, N(CH₃)), 1.00-2.00 (overlapping peaks, VitE), 0.70-0.90 (m, 12H, overlapping CH3 on VitE) | 1:10 | 1:8 | 1.20 |
| 7 | VE/BnCl(1:20) | MTC-VitE/ MTC-BnCl | 7.10-7.70 (m, 69H, overlapping peaks of initiator Ph and Bn), 5.00-5.40 (m, 34H, overlapping peaks of initiator CH₂Ph and Bn), 4.68 (m, 32H), 4.29 (m, 64H), 3.07 (m, 144H, N(CH₃)), 1.00-2.00 (overlapping peaks, VitE), 0.70-0.90 (m, 12H, overlapping CH₃ on VitE) | 1:20 | 1:16 | 1.20 |
| 8 | VE/BnCl(1:30) | MTC-VitE/ MTC-BnCl | 7.20-7.70 (m, 97H, overlapping peaks of initiator Ph and Bn), 5.00-5.40 (m, 48H, overlapping peaks of initiator CH₂Ph and Bn), 4.67 (m, 46H), 4.30 (m, 92H), 3.07 (m, 207H, N(CH₃)), 1.00-2.00 (overlapping peaks, VitE), 0.70-0.90 (m, 12H, overlapping CH₃ on VitE) | 1:30 | 1:23 | 1.21 |

[a]GPC was performed on pre-quaternized polymers

III. Preparation of Triblock Copolymers

The organocatalytic ring opening polymerization (ROP) of MTC-VitE, initiated by poly(ethylene glycol) (HO-PEG-OH) was achieved using DBU/thiourea catalysts combination according to the Scheme 2.

Scheme 2.

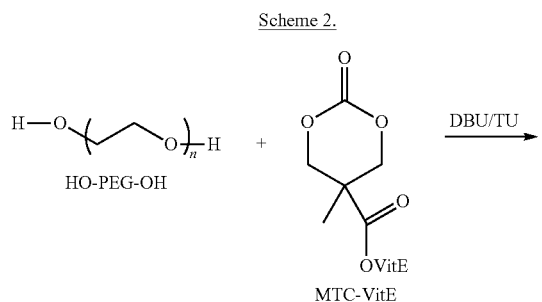

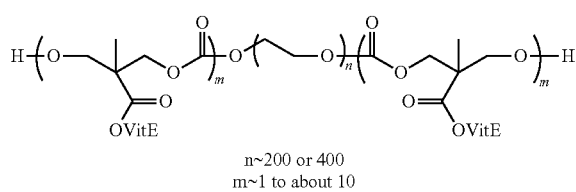

n~200 or 400
m~1 to about 10

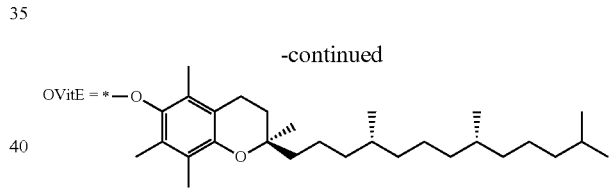

The ring opening polymerizations (ROP) with MTC-VitE were incomplete and the conversion efficiency was around 60%. The excess monomers and reagents were removed by repeated precipitation with diethyl ether. The final compositions of the polymers were confirmed by comparison of the OCH₂—CH₂ peak of PEG to the four CH₃ peaks on the MTC-VitE hydrophobic tail. The hydrophobicity of the polymer can be adjusted by varying the amount of MTC-VitE moiety. The hydrophilicity can be adjusted by varying the HO-PEG-OH length. The triblock copolymers was not endcapped.

Examples 9 to 14

The formation of Example 11, VitE1.25-PEG(20k)-VitE1.25, is representative. In a 20-mL vial containing a magnetic stir bar in the glove box, MTC-VitE (58.9 mg, 100 micromoles, 4.0 equivalent), HO-PEG-OH (Mn=20 kDa, 500 mg, 25 micromoles, 1.0 equivalent) and TU (9.3 mg, 25 micromoles, 1.0 equivalent) were dissolved in dichloromethane (4 mL). To this solution, DBU (3.7 microliters, 25 micromoles, 1.0 equivalent) was added to initiate polymerization. The reaction mixture was allowed to stir at room temperature and aliquots of samples were taken to monitor the monomer conversion and evolution of molecular weight by $^1$H NMR spectroscopy and SEC. After 120 minutes, the reaction mixture was quenched by the addition of excess (~20 mg) of benzoic acid and was precipitated into ice-cold diethyl ether (2×50 mL). The resultant polymer was dried in a vial for about 1-2 days until a constant sample mass was obtained, as white powder.

Table 8 summarizes the triblock copolymers formed using the reaction of Scheme 2.

TABLE 8

| Example | Name | Name 2 | $Mn^{PEG}$ (kDa)[a] | MTC-VitE Feed Ratio | $DP^b$ (m) | $f^{PEG}$ |
|---|---|---|---|---|---|---|
| 9 | PEG(10k)-4 | VitE1.25-PEG(10k)-VitE1.25 | 10 | 4 | 1.25 | 87.2 |
| 10 | PEG(10k)-8 | VitE2.5-PEG(10k)-VitE2.5 | 10 | 8 | 2.5 | 77.3 |
| 11 | PEG(20k)-4 | VitE1.25-PEG(20k)-VitE1.25 | 20 | 4 | 1.25 | 93.1 |
| 12 | PEG(20k)-8 | VitE2.5-PEG(20k)-VitE2.5 | 20 | 8 | 2.5 | 87.2 |
| 13 | PEG(20k)-20 | VitE6.5-PEG(20k)-VitE6.5 | 20 | 20 | 6.5 | 72.3 |
| 14 | PEG(20k)-30 | VitE8.5-PEG(20k)-VitE8.5 | 20 | 30 | 8.5 | 66.6 |

[a] Number average molecular weight data from supplier
[b] Based on 1H NMR spectroscopy
[c] Weight fraction of PEG, $f^{PEG} = Mn^{PEG}/(Mn^{PEG} + (2 \times DP \times 588.83))$ Table 9 lists the analysis of the triblock copolymers.

TABLE 9

| Example | Name | Name 2 | Selected 1HNMR peaks (intensity) | MTC-VitE Feed Mole Ratio | Actual Mole Ratio | GPC |
|---|---|---|---|---|---|---|
| 9 | PEG(10k)-4 | VitE1.25-PEG(10k)-VitE1.25- | 3.40-4.00 (s, 906H, OCH2CH2 PEG), 1.00-2.00 (overlapping peaks, VitE), 0.75-0.95 (m, 30H, overlapping CH3 on VitE) | 1:4 | 1:2.5 | 1.09 |
| 10 | PEG(10k)-8 | VitE2.5-PEG(10k)-VitE2.5 | 3.40-4.00 (s, 906H, OCH2CH2 PEG), 1.00-2.00 (overlapping peaks, VitE), 0.75-0.95 (m, 60H, overlapping CH3 on VitE) | 1:8 | 1:5 | 1.07 |
| 11 | PEG(20k)-4 | VitE1.25-PEG(20k)-VitE1.25 | 3.40-4.00 (s, 1815H, OCH2CH2 PEG), 1.00-2.00 (overlapping peaks, VitE), 0.75-0.95 (m, 30H, overlapping CH3 on VitE) | 1:4 | 1:2.5 | 1.07 |
| 12 | PEG(20k)-8 | VitE2.5-PEG(20k)-VitE2.5 | 3.40-4.00 (s, 1815H, OCH2CH2 PEG), 1.00-2.00 (overlapping peaks, VitE), 0.75-0.95 (m, 60H, overlapping CH3 on VitE) | 1:8 | 1:5 | 1.12 |
| 13 | PEG(20k)-20 | VitE6.5-PEG(20k)-VitE6.5 | 3.40-4.00 (s, 1815H, OCH2CH2 PEG), 1.00-2.00 (overlapping peaks, VitE), 0.75-0.95 (m, 156H, overlapping CH3 on VitE) | 1:20 | 1:13 | 1.15 |
| 14 | PEG(20k)-30 | VitE8.5-PEG(20k)-VitE8.5 | 3.40-4.00 (s, 1815H, OCH2CH2 PEG), 1.00-2.00 (overlapping peaks, VitE), 0.75-0.95 (m, 204H, overlapping CH3 on VitE) | 1:30 | 1:17 | 1.12 |

IV. Preparation of Hydrogels and Organogels
Preparation of Blank Hydrogels.

Example 15

VitE1.25-PEG(20k)-VitE1.25 (40 mg) was dissolved in HPLC grade water (1 ml) at 25° C. to form a 4 wt. % hydrogel.

Example 16

VitE1.25-PEG(20k)-VitE1.25 (80 mg) was dissolved in HPLC grade water (1 ml) at 25° C. to form an 8 wt. % hydrogel. The gel was formed in 4 hours.

Example 17

VitE2.5-PEG(20k)-VitE2.5 (40 mg) was dissolved in HPLC grade water (1 ml) at ambient temperature to form a 4 wt. % hydrogel. The gel was formed in 4 hours.

Example 18

VitE2.5-PEG(20k)-VitE2.5 (80 mg) was dissolved in HPLC grade water (1 ml) at ambient temperature to form a 8 wt. % hydrogel. The gel was formed in 4 hours.
Preparation of Blank ABA Organogels.

Example 19

A 10 wt. % organogel was formed by dissolving VitE6.5-PEG(20k)-VitE6.5 (20 mg) in KOLLIPHOR RH40 (200 microliters) and heating the mixture at 85° C. with stirring at 1400 rpm for 1 hour. HPLC grade water (10 microliters) was then added to the organogel with stirring.

Example 20

The procedure of Example 19 was used to prepare a 10 wt. % organogel of VitE8.5-PEG(20k)-VitE8.5.

Preparation of ABA Copolymer/Sodium Nicotinate Hydrogels.

Example 21

Sodium nicotinate was dissolved in HPLC grade water at a concentration of 3 g/L. This solution (1 ml) was then added to VitE1.25-PEG(20k)-VitE1.25 (40 mg) at 25° C. to form a hydrogel containing 4 wt. % VitE1.25-PEG(20k)-VitE1.25 and 0.3 wt. % sodium nicotinate based on total weight of the hydrogel.

Example 22

Sodium nicotinate was dissolved in HPLC grade water at a concentration of 3 g/L. This solution (1 ml) was then added to VitE1.25-PEG(20k)-VitE1.25 (80 mg) at 25° C. to form a hydrogel containing 8 wt. % VitE1.25-PEG(20k)-VitE1.25 and 0.3 wt. % sodium nicotinate based on total weight of the hydrogel.

Example 23

Sodium nicotinate was dissolved in HPLC grade water at a concentration of 3 g/L. This solution (1 ml) was then added to VitE2.5-PEG(20k)-VitE2.5 (40 mg) at ambient temperature to form a hydrogel containing 4 wt. % VitE2.5-PEG(20k)-VitE2.5 and 0.3 wt. % sodium nicotinate based on total weight of the hydrogel.

Preparation of ABA Copolymer/Herceptin Hydrogels.

Example 24

The antibody herceptin was dissolved in HPLC grade water at a concentration of 10 g/L. This solution (1 ml) was then added to VitE1.25-PEG(20k)-VitE1.25 (40 mg) at ambient temperature to form a hydrogel containing 4 wt. % VitE1.25-PEG(20k)-VitE1.25 and 1.0 wt. % herceptin based on total weight of the hydrogel.

Example 25

The antibody herceptin was dissolved in HPLC grade water at a concentration of 10 g/L. This solution (1 ml) was then added to VitE2.5-PEG(20k)-VitE2.5 (40 mg) at 25° C., to form a hydrogel containing 4 wt. % VitE2.5-PEG(20k)-VitE2.5 and 1.0 wt. % herceptin based on total weight of the hydrogel.

Preparation of Antimicrobial ABA Triblock/Doxycycline Organogels

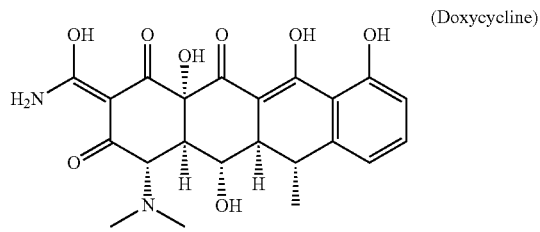 [SMILES: C[C@H]1c2cccc(O)c2C(O)=C2C(=O)[C@]3(O)C(=O)/C(=C(/N)O)C(=O)[C@@H](N(C)C)[C@@H]3[C@@H](O)[C@@H]21]
(Doxycycline)

To prepare the antimicrobial organogels, the triblock copolymer was first dissolved in KOLLIPHOR RH40 by heating at 85° C. Doxycycline was separately dissolved in filtered HPLC water in a cell culture hood. The two solutions were then mixed together at room temperature for the formation of organogels.

Example 26

VitE6.5-PEG(20k)-VitE6.5 (20 mg) was dissolved in KOLLIPHOR RH40 (200 microliters), heating at 85° C. and stirring at 1400 rpm for 1 hour. After that, a doxycycline solution (200 g/L in HPLC grade water) (10 microliters) was added and stirred to form an organogel containing 10 wt. % VitE6.5-PEG(20k)-VitE6.5 and 1 wt. % doxycycline based on total weight of the hydrogel.

Example 27

VitE8.5-PEG(20k)-VitE8.5 (20 mg) was dissolved in KOLLIPHOR RH40 (200 microliters), heating at 85° C. and stirring at 1400 rpm for 1 hour. After that, a doxycycline solution (200 g/L in HPLC grade water) (10 microliters) was added and stirred to form an organogel containing 10 wt. % VitE8.5-PEG(20k)-VitE8.5 and 1 wt. % doxycycline based on total weight of the hydrogel.

Preparation of ABA Triblock/Cationic Polymer Hydrogels.

To prepare the antimicrobial hydrogels, cationic polymer was first dissolved in filtered HPLC water at 25° C. in a bio-hood. The resultant solution was then added to triblock copolymer solid for dissolution and left to stand at room temperature

Example 28

Cationic polymer VE/BnCl (1:30) (1 mg) was dissolved with sterile HPLC grade water (1 ml) to form a solution of concentration (1 g/L). This solution (1 ml) was then added to VitE1.25-PEG(20k)-VitE1.25 (40 mg) and allowed to stand 4 hours at ambient temperature to form a cationic polymer loaded hydrogel containing 4 wt. % VitE1.25-PEG(20k)-VitE1.25 and 0.1 wt. % VE/BnCl (1:30) based on total weight of the hydrogel.

Example 29

Cationic polymer VE/PrBr(1:30) (1 mg) was dissolved with sterile HPLC grade water 1 ml to form a solution of concentration (1 g/L). This solution (1 ml) was then added to VitE1.25-PEG(20k)-VitE1.25 (40 mg) and allowed to stand 4 hours at ambient temperature to form a cationic polymer loaded hydrogel containing 4 wt. % VitE1.25-PEG(20k)-VitE1.25 and 0.1 wt. % VE/PrBr(1:30) based on total weight of the hydrogel.

Preparation of Two and Three Component Hydrogels Containing Fluconazole.

Example 30

Fluconazole (0.5 mg) was dissolved in sterile HPLC grade water (1 ml) at 25° C. at a concentration of 0.5 g/L. This solution (1 ml) was then added to VitE1.25-PEG(20k)-VitE1.25 (40 mg) to form a fluconazole loaded hydrogel containing 4 wt. % VitE1.25-PEG(20k)-VitE1.25 and 0.05 wt. % fluconazole (500 mg/L) based on total weight of the hydrogel.

Example 31

A solution was prepared containing cationic polymer VE/BnCl (1:30) (0.156 mg) (0.5 MBC=156 mg/L for *C. albicans*) and fluconazole (0.01 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25, 0.0156 wt. % VE/BnCl (1:30) and 0.001 wt. % fluconazole based on total weight of the hydrogel.

Example 32

A solution was prepared containing cationic polymer VE/BnCl (1:30) (0.078 mg) at 0.25 MBC (78 mg/L for *C. albicans*) and fluconazole (0.04 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25, 0.0078 wt. % VE/BnCl (1:30), and 0.004 wt. % fluconazole based on total weight of the hydrogel.

Preparation of Two and Three Component Hydrogels Containing Doxycycline.

Example 33 A solution was prepared containing cationic polymer VE/BnCl (1:30) (0.0156 mg) and doxycycline (0.0025 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25, 0.00156 wt. % VE/BnCl (1:30), and 0.00025 wt. % fluconazole based on total weight of the hydrogel.

Example 34

A solution was prepared containing cationic polymer VE/BnCl (1:30) (0.0156 mg) and doxycycline (0.005 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25, 0.00156 wt. % VE/BnCl (1:30), and 0.0005 wt. % fluconazole based on total weight of the hydrogel.

Example 35

A solution was prepared containing cationic polymer VE/BnCl (1:30) (0.0312 mg) and doxycycline (0.0025 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25, 0.00312 wt. % VE/BnCl (1:30), and 0.00025 wt. % fluconazole based on total weight of the hydrogel.

Example 36

A solution was prepared containing cationic polymer VE/BnCl (1:30) (0.0312 mg) and doxycycline (0.0025 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25, 0.00312 wt. % VE/BnCl (1:30), and 0.00025 wt. % fluconazole based on total weight of the hydrogel.

Hydrogels prepared at MBC concentration for *S. aureus*, *E. coli*, and *C. albicans*

Example 37

A solution was prepared containing cationic polymer VE/BnCl (1:30) at (0.156 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25 and 0.0156 wt. % VE/BnCl (1:30) based on total weight of the hydrogel.

Example 38

A solution was prepared containing cationic polymer VE/PrBr(1:30) at (0.625 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25 and 0.0625 wt. % VE/PrBr(1:30) based on total weight of the hydrogel.

Example 39

A solution was prepared containing cationic polymer VE/BnCl (1:30) at (0.3125 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25 and 0.03125 wt. % VE/BnCl (1:30) based on total weight of the hydrogel.

Example 40

A solution was prepared containing cationic polymer VE/PrBr(1:30) at (0.25 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25 and 0.025 wt. % VE/PrBr(1:30) based on total weight of the hydrogel.

Example 41

A solution was prepared containing cationic polymer VE/BnCl (1:30) at (0.313 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25 and 0.0313 wt. % VE/BnCl (1:30) based on total weight of the hydrogel.

Example 42

A solution was prepared containing cationic polymer VE/PrBr(1:30) at (0.625 mg) in sterile HPLC grade water (1 ml) at 25° C. This solution (1 ml) was then added to VitE1.25-PEG(20k)-VitE1.25 (40 mg) to form a loaded hydrogel containing 4 wt. % VitE1.25-PEG(20k)-VitE1.25 and 0.0625 wt. % VE/PrBr(1:30) based on total weight of the hydrogel.

Other Two and Three Component Hydrogels Containing Fluconazole

Example 43

Following the general procedure of Example 30 a fluconazole loaded hydrogel was prepared containing 4 wt. % VitE1.25-PEG(20k)-VitE1.25 and 0.3 wt. % fluconazole (500 mg/L) based on total weight of the hydrogel.

Example 44

Following the general procedure of Example 31 a loaded hydrogel was prepared containing 4 wt. % VitE1.25-PEG (20k)-VitE1.25, 0.3 wt. % VE/BnCl (1:30) and 0.3 wt. % fluconazole based on total weight of the hydrogel.

Table 10 lists the hydrogel and organogel compositions.

TABLE 10

| Example 1 | Component 1 | Component 2 | Component 3 | Component 1 Wt. % | Component 2 Wt. % | Component 3 Wt. % | Solvent |
|---|---|---|---|---|---|---|---|
| 15 | VitE1.25-PEG(20k)-VitE1.25 | | | 4 | | | Water |
| 16 | VitE1.25-PEG(20k)-VitE1.25 | | | 8 | | | Water |
| 17 | VitE2.5-PEG(10k)-VitE2.5 | | | 4 | | | Water |
| 18 | VitE2.5-PEG(20k)-VitE2.5 | | | 8 | | | Water |
| 19 | VitE6.5-PEG(20k)-VitE6.5 | | | 10 | | | KOLLIPHOR RH40 |
| 20 | VitE8.5-PEG(20k)-VitE8.5 | | | 10 | | | KOLLIPHOR RH40 |
| 21 | VitE1.25-PEG(20k)-VitE1.25 | Sodium Nicotinate | | 4 | 0.3 | | Water |
| 22 | VitE1.25-PEG(20k)-VitE1.25 | Sodium Nicotinate | | 8 | 0.3 | | Water |
| 23 | VitE2.5-PEG(20k)-VitE2.5 | Sodium Nicotinate | | 4 | 0.3 | | Water |
| 24 | VitE1.25-PEG(20k)-VitE1.25 | Herceptin | | 4 | 1 | | Water |
| 25 | VitE2.5-PEG(20k)-VitE2.5 | Herceptin | | 4 | 1 | | Water |
| 26 | VitE6.5-PEG(20k)-VitE6.5 | Doxycycline | | 10 | 1 | | KOLLIPHOR RH40 |
| 27 | VitE8.5-PEG(20k)-VitE8.5 | Doxycycline | | 10 | 1 | | KOLLIPHOR RH40 |
| 28 | VitE1.25-PEG(20k)-VitE1.25 | VE/BnCl(1:30) | | 4 | 0.1 | | Water |
| 29 | VitE1.25-PEG(20k)-VitE1.25 | VE/PrBr(1:30) | | 4 | 0.1 | | Water |
| 30 | VitE1.25-PEG(20k)-VitE1.25 | Fluconazole | | 4 | 0.05 | | Water |
| 31 | VitE1.25-PEG(20k)-VitE1.25 | VE/BnCl(1:30) | Fluconazole | 4 | 0.0156 | 0.001 | Water |
| 32 | VitE1.25-PEG(20k)-VitE1.25 | VE/BnCl(1:30) | Fluconazole | 4 | 0.0078 | 0.004 | Water |
| 33 | VitE1.25-PEG(20k)-VitE1.25 | VE/BnCl(1:30) | Doxycycline | 4 | 0.00156 | 0.00025 | Water |
| 34 | VitE1.25-PEG(20k)-VitE1.25 | VE/BnCl(1:30) | Doxycycline | 4 | 0.00156 | 0.0005 | Water |
| 35 | VitE1.25-PEG(20k)-VitE1.25 | VE/BnCl(1:30) | Doxycycline | 4 | 0.00313 | 0.00025 | Water |

TABLE 10-continued

| Example 1 | Component 2 | Component 3 | Component 1 Wt. % | Component 2 Wt. % | Component 3 Wt. % | Solvent |
|---|---|---|---|---|---|---|
| 36 | VitE1.25-PEG(20k)-VitE1.25 | VE/BnCl(1:30) | Doxycycline | 4 | 0.00313 | 0.00025 | Water |
| 37 | VitE1.25-PEG(20k)-VitE1.25 | VE/BnCl(1:30) | | 4 | 0.0156 | | Water |
| 38 | VitE1.25-PEG(20k)-VitE1.25 | VE/PrBr(1:30) | | 4 | 0.0625 | | Water |
| 39 | VitE1.25-PEG(20k)-VitE1.25 | VE/BnCl(1:30) | | 4 | 0.03125 | | Water |
| 40 | VitE1.25-PEG(20k)-VitE1.25 | VE/PrBr(1:30) | | 4 | 0.25 | | Water |
| 41 | VitE1.25-PEG(20k)-VitE1.25 | VE/BnCl(1:30) | | 4 | 0.0313 | | Water |
| 42 | VitE1.25-PEG(20k)-VitE1.25 | VE/PrBr(1:30) | | 4 | 0.0625 | | Water |
| 43 | VitE1.25-PEG(20k)-VitE1.25 | Fluconazole | | 4 | 0.3 | | Water |
| 44 | VitE1.25-PEG(20k)-VitE1.25 | VE/BnCl(1:30) | Fluconazole | 4 | 0.3 | 0.3 | Water |

VI. Preparation of Drug Solutions
Preparation of Herceptin Solutions

For cell culture studies, herceptin was dissolved using sterile HPLC grade water at the following concentrations, 0.005, 0.02, 0.1, 0.5, 1 and 5 g/L.

Preparation of Fluconazole Solutions

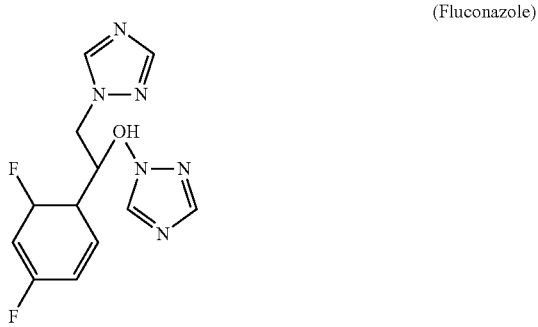 [SMILES: FC1=CC(F)C(C(Cn2cncn2)On2cncn2)C=C1]
(Fluconazole)

For antimicrobial studies, fluconazole was dissolved using sterile HPLC grade water at the appropriate concentrations. For example, a solution containing 5 mg/L fluconazole was formed by adding sterile HPLC grate water to a stock solution (1 g/L) of fluconazole.

VII. Properties

Rheological Characterization

Rheological analysis of the hydrogels was performed on an ARES-G2 rheometer (TA Instruments, USA) equipped with a plate-plate geometry of 8 mm diameter. Measurements were taken by equilibrating the hydrogels at 25° C. between the plates at a gap of 1.0 mm. The data were collected under controlled strain of 0.2% and a frequency scan of 1.0 to 100 rad/sec. The shear storage modulus (G') and loss modulus (G") of hydrogels were measured at each point. For shear-thinning studies, the viscosity of the hydrogels was monitored as a function of shear rate from 0.1 to 10 sec$^{-1}$. From the storage modulus G', the molar weight between the effective cross-links, Mc, was calculated using the following equation:

$$G' = \rho RT/Mc$$

where $\rho$ is the polymer concentration [g/m$^3$], R is the molar gas constant and T is the absolute temperature.

Restoration of elastic modulus of hydrogel after network disruption was studied by applying high strain of 100% for 200 seconds and monitoring the changes in G' and G" at a constant frequency of 1 rad/sec.

Scanning Electron Microscope (SEM) Imaging

To minimize morphological perturbations, the hydrogels were cryo-fixed by transferring the sample into a chamber filled with liquid nitrogen. A day of freeze-drying process was then followed. The morphology of the gel was observed using a scanning electron microscope (SEM) (Jeol JSM-7400F, Japan).

In Vitro Release of Sodium Nicotinate from Hydrogel

The release of sodium nicotinate from the hydrogels was studied using the dialysis method. Dialysis membrane tube with molecular weight cutoff (MWCO) of 500 Da (Spectrum Laboratories, U.S.A.) containing 0.5 mL gel was immersed in 25 ml of the release medium (i.e., PBS (pH 7.4)). This was shaken in a water bath at 100 rpm at 37° C. At designated time intervals, 0.5 mL of the release medium was removed and replaced with fresh medium. The medium that has been removed was mixed with HPLC mobile phase consisting of 50 mM KH$_2$PO$_4$ (adjusted to pH 7.0) and methanol in the volume ratio of 99:1. Drug content was analyzed using high performance liquid chromatography (HPLC, Waters 996 PDA detector, U.S.A.) at 220 nm UV wavelength.

In Vitro Release of Herceptin from Hydrogel

Herceptin-loaded hydrogels were transferred to Transwell inserts (Corning, U.S.A.). The inserts were then immersed in 25 ml of the release medium (i.e., PBS (pH 7.4)). This was kept shaking in a water bath at 100 rpm at 37° C. At designated time intervals, 0.1 mL of the release medium was removed and replaced with fresh medium. The released amount of herceptin was quantified using the protein quantification BCA assay (Pierce, U.S.A.).

In Vitro Release of Doxycycline from Organogel

Doxycycline-loaded organogels were transferred to Transwell inserts (Corning, U.S.A.). The inserts were then immersed in 25 ml of the release medium (either PBS pH 7.4 or $1\times10^4$ U/L lipase solution in PBS pH 7.4). This was kept shaking in a water bath at 100 rpm at 37° C. At designated time intervals, 10 mL of the release medium was removed and replaced with fresh medium. The release medium was completely exchanged with fresh medium after each overnight of incubation to maintain the activities of the lipase. The medium that was collected was mixed with HPLC mobile phase consisting of 25 mM $KH_2PO_4$:acetonitrile in the volume ratio of 30:70 (adjusted to pH 3.0). Drug content was analyzed using high performance liquid chromatography (HPLC, Waters 996 PDA detector, U.S.A.) at 260 nm UV wavelength.

Cytotoxicity Study of Hydrogel Using MTT Assay

Human dermal fibroblasts were seeded onto 96-well plates at a density of $2\times10^4$ cells per well, and cultivated in 100 microliters of growth medium. The plates were then returned to incubators for 24 hours to reach 70% to 80% confluency before treatment. When the desired cell confluency was reached, the spent growth medium was removed from each well and replaced with 50 microliters of fresh medium and 50 microliters of hydrogel, and incubated for 24 hours. Each condition was tested in four replicates. When the treatment was completed, the culture medium was removed and 10 microliters of MTT solution was added with 100 microliters of fresh medium. The plates were then returned to the incubator and maintained in 5% $CO_2$, at 37° C. for a further 3 hours. The growth medium and excess MTT in each well were then removed. 150 microliters of DMSO was then added to each well to dissolve the internalized purple formazan crystals. An aliquot of 100 microliters was taken from each well and transferred to a new 96-well plate. The plates were then assayed at 550 nm and reference wavelength of 690 nm using a microplate reader (Tecan, U.S.A.). The absorbance readings of the formazan crystals were taken to be those at 550 nm subtracted by those at 690 nm. The results were expressed as a percentage of the absorbance of the control cells without any treatment.

Cytotoxicity Study of Organogel Using MTT Assay

Human dermal fibroblasts were seeded onto 24-well plates at a density of $6\times10^4$ cells per well, and cultivated in 500 microliters of growth medium. The plates were then returned to incubators for 24 hours to reach 70%-80% confluency before treatment. When the desired cell confluency was reached, the spent growth medium was removed from each well and replaced with 500 microliters of fresh medium. 50 microliters of organogel was then added into Transwell inserts (Corning, U.S.A.) and immersed into the culture medium. The cells were then incubated for 24 hours with the organogels. Each condition was tested in 3 replicates. When the treatment was completed, the culture medium was removed and 10 μl of MTT solution was added with every 100 microliters of fresh medium. The plates were then returned to the incubator and maintained in 5% $CO_2$ at 37° C. for 3 hours. The growth medium and excess MTT in each well were then removed. 600 microliters of DMSO was then added to each well to dissolve the internalised purple formazan crystals. An aliquot of 100 microliters was taken from each well and transferred to a new 96-well plate. The plates were then assayed at 550 nm and reference wavelength of 690 nm using a microplate reader (Tecan, U.S.A.). The absorbance readings of the formazan crystals were taken to be those at 550 nm subtracted by those at 690 nm. The results were expressed as a percentage of the absorbance of the control cells without any treatment.

Mechanical Properties of Hydrogels and Organogels

Figure 1B:
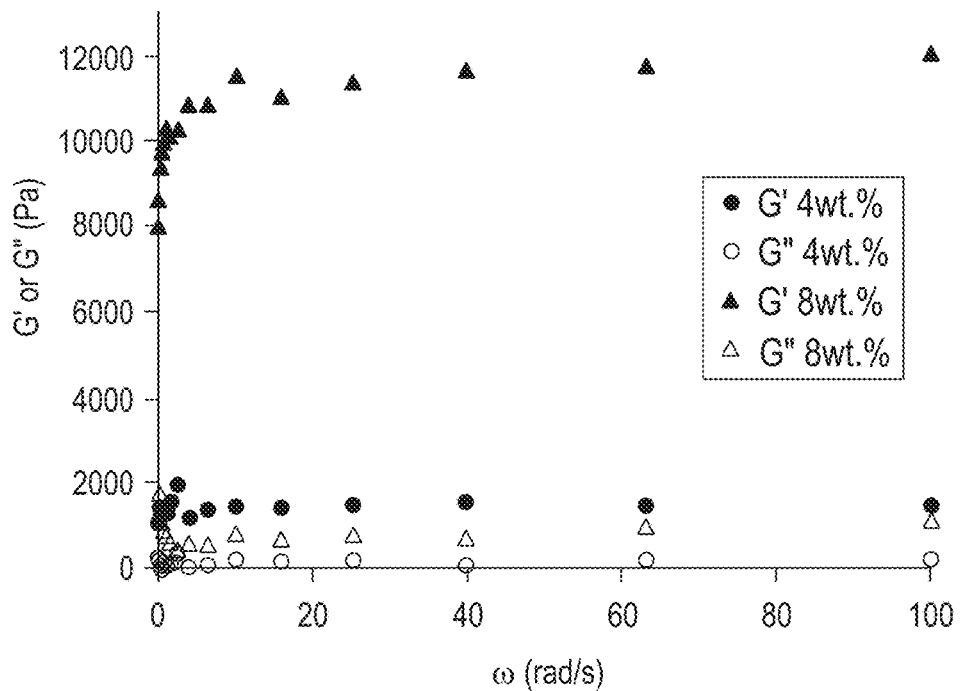
FIG. 1B is a graph showing the storage (G') and loss (G") moduli of blank hydrogels containing 4 wt. % and 8 wt. % VitE2.5-PEG(20k)-VitE2.5 in HPLC water (Example 17 and Example 18, respectively).
Figure 1C:
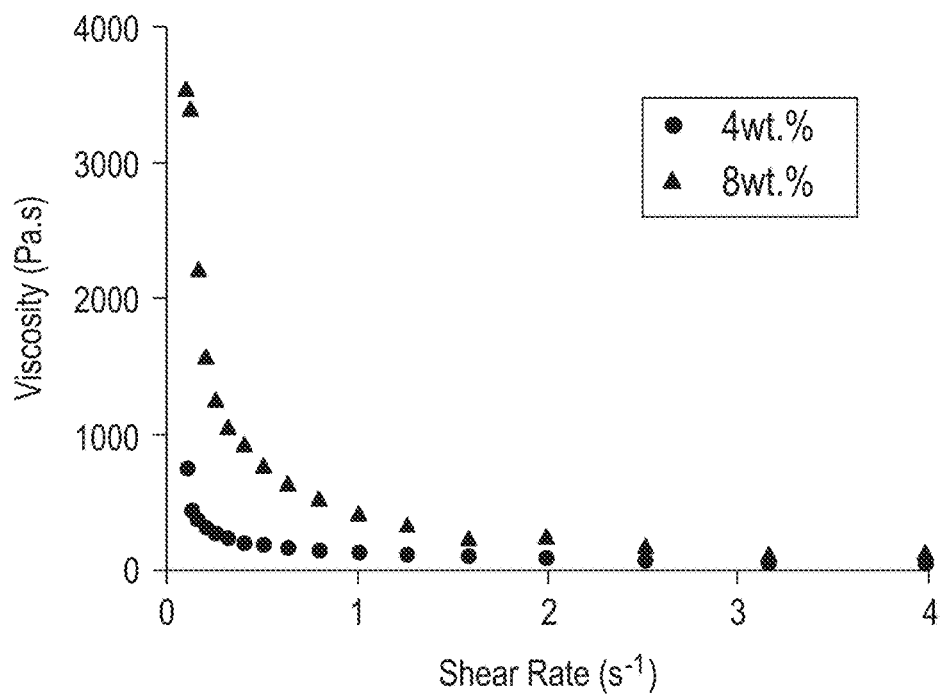
FIG. 1C is a graph showing the viscosity dependence on shear rate of blank hydrogels containing 4 wt. % and 8 wt. % VitE1.25-PEG(20k)-VitE1.25 in HPLC water (Example 15 and Example 16, respectively).
Figure 1D:
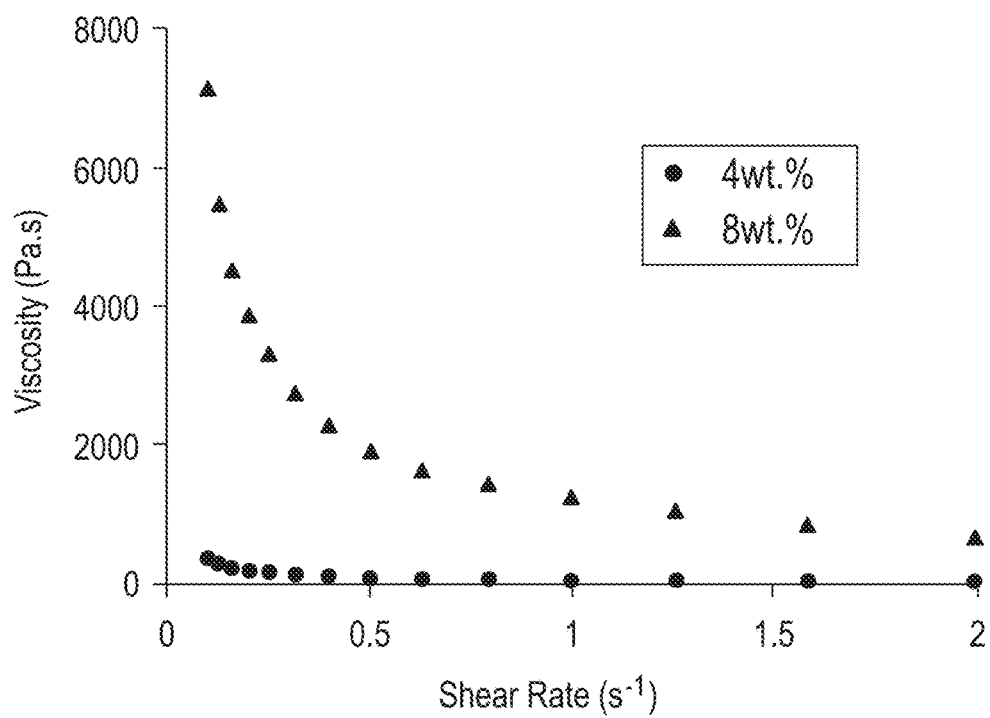
FIG. 1D is a graph showing the viscosity dependence on shear rate of blank hydrogels containing 4 wt. % and 8 wt. % VitE2.5-PEG(20k)-VitE2.5 in HPLC water (Example 17 and Example 18, respectively).

The influence of concentration, hydrophobic/hydrophilic balance and chemical composition of the amphiphilic copolymers was investigated using dynamic mechanical analysis. Polymer concentration strongly affects the storage modulus G' of the hydrogel. FIGS. 1A to 1D are graphs showing the mechanical properties of blank hydrogels. FIG. 1A is a graph showing the storage (G') and loss (G") moduli of blank hydrogels containing 4 wt. % and 8 wt. % VitE1.25-PEG(20k)-VitE1.25 in HPLC water (Example 15 and Example 16, respectively). FIG. 1B is a graph showing the storage (G') and loss (G") moduli of blank hydrogels containing 4 wt. % and 8 wt. % VitE2.5-PEG(20k)-VitE2.5 in HPLC water (Example 17 and Example 18, respectively). FIG. 1C is a graph showing the viscosity dependence on shear rate of blank hydrogels containing 4 wt. % and 8 wt. % VitE1.25-PEG(20k)-VitE1.25 in HPLC water (Example 15 and Example 16, respectively). FIG. 1D is a graph showing the viscosity dependence on shear rate of blank hydrogels containing 4 wt. % and 8 wt. % VitE2.5-PEG(20k)-VitE2.5 in HPLC water (Example 17 and Example 18, respectively).

As shown in FIG. 1A doubling the concentration (4 to 8 wt. %) results in 4 to 10 times higher G' values. In particular, the 8 wt. % VitE2.5-PEG(20k)-VitE2.5 gel has a storage modulus G' of about 12000 Pa, which is nearly 10-fold greater compared to the 4 wt. % gel (G' 1400 Pa). The influence of the balance between the hydrophobic and hydrophilic portions of the polymers on the gel stiffness can be seen at higher polymer concentration. An increase in the MTC-VitE subunits from 1.25 to 2.5 at a concentration of 8 wt. % in HPLC grade water results in an increase in the storage modulus G' from about 5000 Pa to about 12000 Pa. The molecular weight between physical crosslinks Mc was determined, summarized in Table 11. Hydrogels with increasing polymer concentration displayed lower Mc values, which corresponds to lower molecular weight between crosslinks and higher crosslink density.

TABLE 11

| Example | Name | Name 2 | Gel (wt. %) | Mc (kDa) |
|---|---|---|---|---|
| 15 | PEG(20k)-4 | VitE1.25-PEG(20k)-VitE1.25 | 4 | 78.6 |
| 16 | PEG(20k)-4 | VitE1.25-PEG(20k)-VitE1.25 | 8 | 39.6 |
| 17 | PEG(20k)-8 | VitE2.5-PEG(20k)-VitE2.5 | 4 | 71.5 |
| 18 | PEG(20k)-8 | VitE2.5-PEG(20k)-VitE2.5 | 8 | 18.2 |

The hydrogel viscosity dependence on shear rate at 25° C. of FIG. 1C (Examples 15 and 16) and FIG. 1D (Examples 17 and 18) clearly demonstrate the shear-thinning properties of the gels. Shear thinning results from disruption of physical crosslinks between the polymer chains with the application of shear stress. Shear-thinning is desirable for both topical and injectable applications.

Figure 1E:
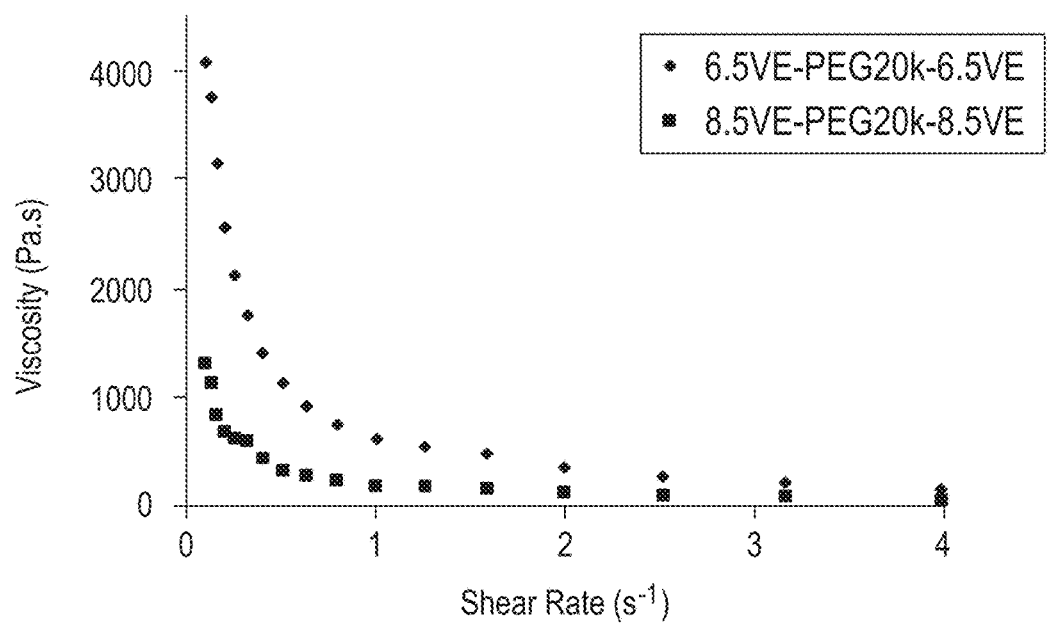
FIG. 1E is a graph showing viscosity dependence on shear rate of blank organogels containing 10 wt. % VitE6.5-PEG(20k)-VitE6.5 and 10 wt. % VitE8.5-PEG(20k)-VitE8.5 organogels in KOLLIPHOR RH40 (Example 19 and Example 20, respectively).

FIG. 1E shows the viscosity dependence on shear rate for 10 wt. % organogels prepared with VitE6.5-PEG(20k)-VitE6.5 (Example 19) and VitE8.5-PEG(20k)-VitE8.5 (Example 20) in KOLLIPHOR RH40. The organogels display high viscosity at low shear rates, indicating a firm, well-bodied structure. At the shear rate increases, the viscosity of the gels falls drastically to become a thin liquid. This indicates the organogel can be well-spread over the skin for topical delivery of therapeutic compounds.

Figure 2:
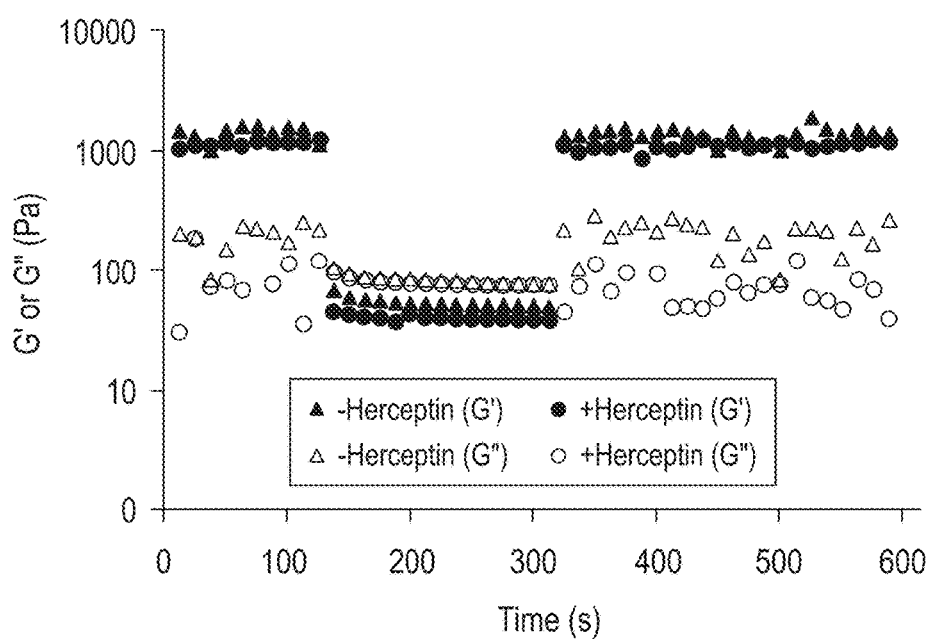
FIG. 2 is a graph showing the dynamic step strain amplitude test (y=0.2 or 100%) of blank hydrogel Example 15 containing 4 wt. % VitE1.25-PEG(20k)-VitE1.25, and a herceptin-loaded hydrogel Example 24 containing 4 wt. % VitE1.25-PEG(20k)-VitE1.25 and 1 wt. % herceptin.

In order for hydrogels to be used as an injectable drug depot, it is essential that the low viscosity solution phase rapidly form a gel when the shear force terminates To study this property, a dynamic step strain amplitude test (y=0.2 or 100%) was applied on the VitE1.25-PEG(20k)-VitE1.25 (4 wt. %) hydrogel in HPLC grade water (Example 15, labeled −Herceptin in FIG. 2) and the herceptin-loaded hydrogel (Example 24, labeled +Herceptin in FIG. 2. The graph of FIG. 2 shows that the initial G' was about 1400 Pa at a small strain (y=0.2%). When subjected to a high strain (y=100%), the G' value immediately decreased by more than 20 times to −67 Pa at 25° C. After 200 seconds of the continuous stress, the strain was returned to y=0.2% and the G' was immediately recovered to about 1400 Pa without any loss at 25° C. This dynamic step strain test mimics the pushing action during clinical administration into the subcutaneous tissue at 25° C. The reversibility of rheological behavior of the hydrogel is advantageous for use as an injectable matrix for delivery of therapeutics.

SEM Imaging of Hydrogel

Figure 3A:
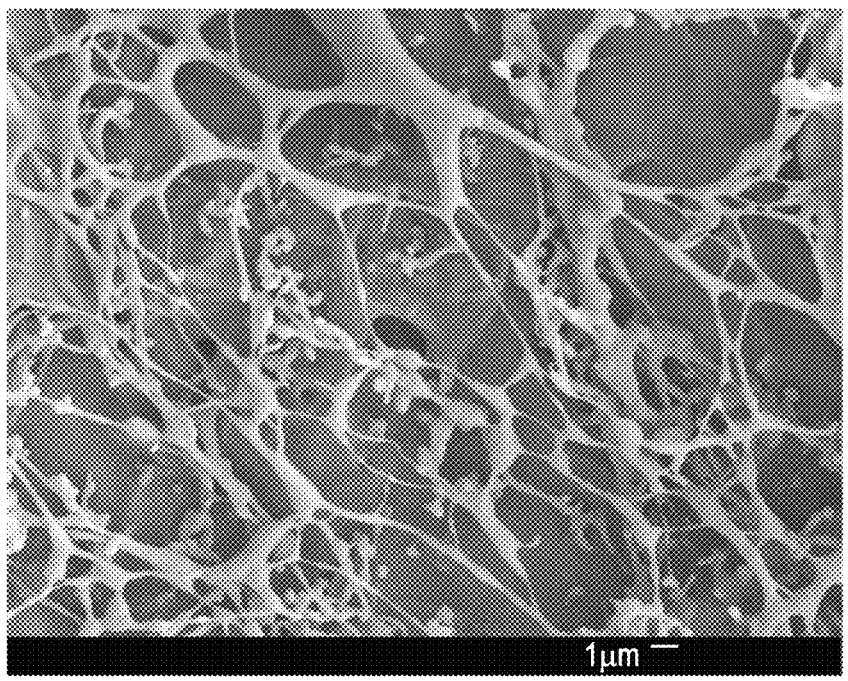
FIGS. 3A and 3B are scanning electron micrographs (SEM) images of cryo-fixed blank hydrogels containing 4 wt. % (Example 15) and 8 wt. % (Example 16) VitE1.25-(PEG20k)-VitE1.25.
Figure 3B:
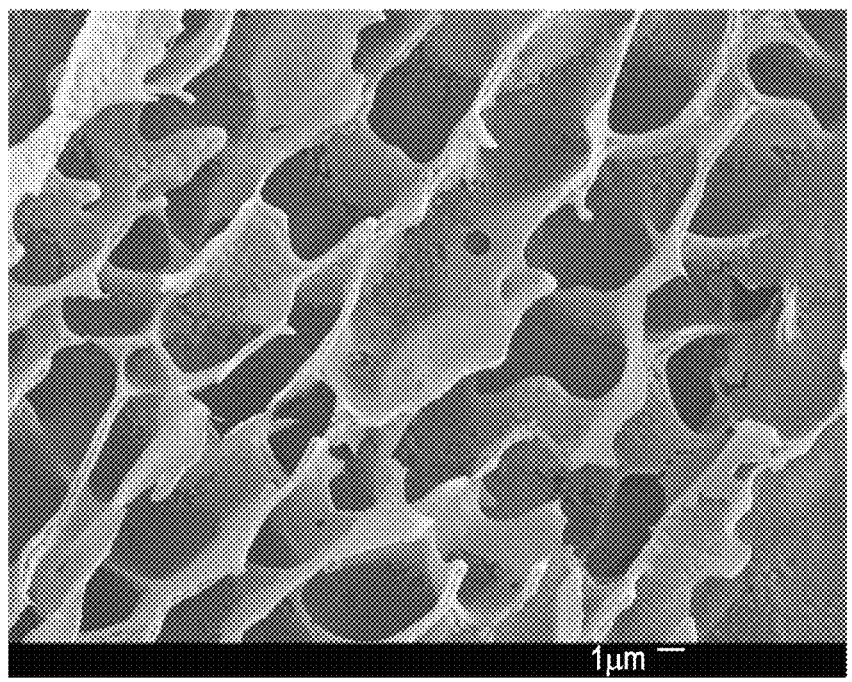
Figure 3C:
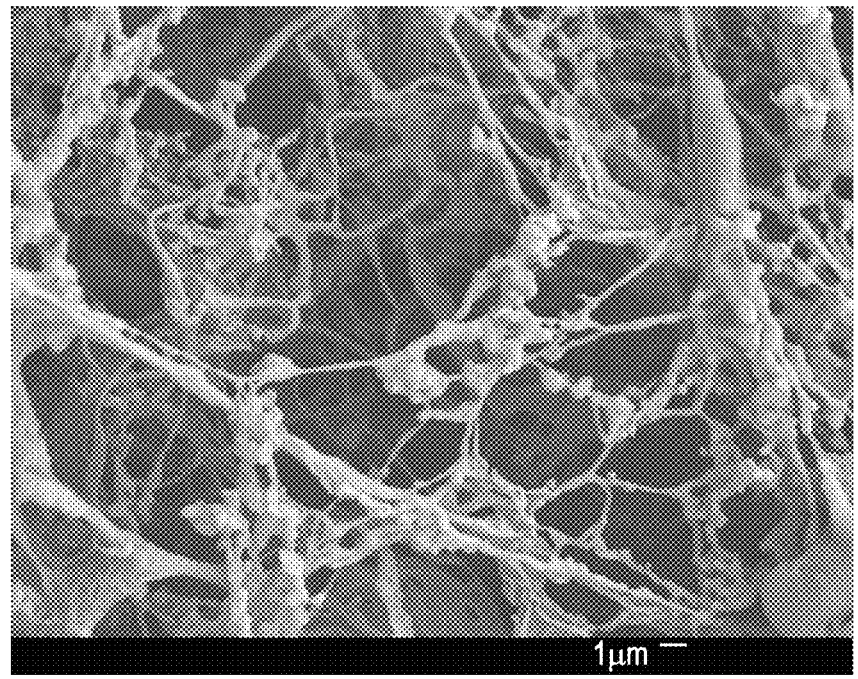
FIGS. 3C and 3D are scanning electron micrographs (SEM) images of cryo-fixed blank hydrogels containing 4 wt. % (Example 17) and 8 wt. % (Example 18) VitE2.5-(PEG20k)-VitE2.5.
Figure 3D:
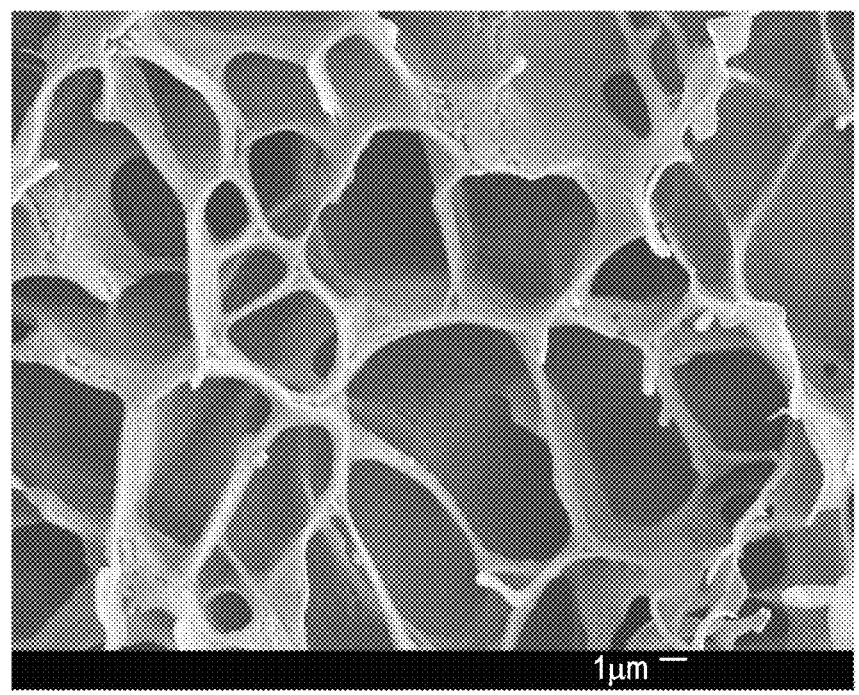

Hydrogels were formed in deionized (DI) water and rapidly transferred into a chamber filled with liquid nitrogen. The frozen hydrogels were freeze-dried for a day and then imaged. Scanning electron micrograph (SEM) images of the hydrogel (FIGS. 3A to 3D) shows that the cross-section morphology and porosity of the hydrogel network is strongly influenced by the polymer concentration, hydrophobic/hydrophilic balance and chemical composition. (FIGS. 3A and 3B are SEMS of blank hydrogels of VitE1.25-PEG(20k)-VitE1.25 at 4 wt. % (Example 15) and 8 wt. % (Example 16) concentration in HPLC grade water, respectively. (FIGS. 3C and 3D are SEMS of blank hydrogels of VitE2.5-PEG(20k)-VitE2.5 at 4 wt. % (Example 17) and 8 wt. % (Example 18) concentration in HPLC grade water, respectively. Long flexible fibers are present in large proportion in 4 wt. % hydrogels of both VitE1.25-PEG (20k)-Long flexible fibers are present in large proportion in 4 wt. % hydrogels of both VitE1.25-PEG(20k)-VitE1.25 (FIG. 3A) and VitE2.5-PEG(20k)-VitE2.5 (FIG. 3C), and this is most likely due to the entanglement of the PEG chains. These long flexible fibers vary in diameter from about 0.1 to about 1 micrometer). Nanosized (<1 micrometer) spherical structures that occur along the lengths of the fibers, which might be micelles that are formed during the self-assembly process of the polymers. At 8 wt. % concentration the hydrogels appear as nanophase-separated sponge structures (FIGS. 3B and 3D). The porosity of the sponge structures appear to be different at different polymer concentrations. At 4 wt. %, the hydrogels appear to be more porous compared to the 8 wt. % hydrogel.

Drug Release from Hydrogel and Organogels

Figure 4A:
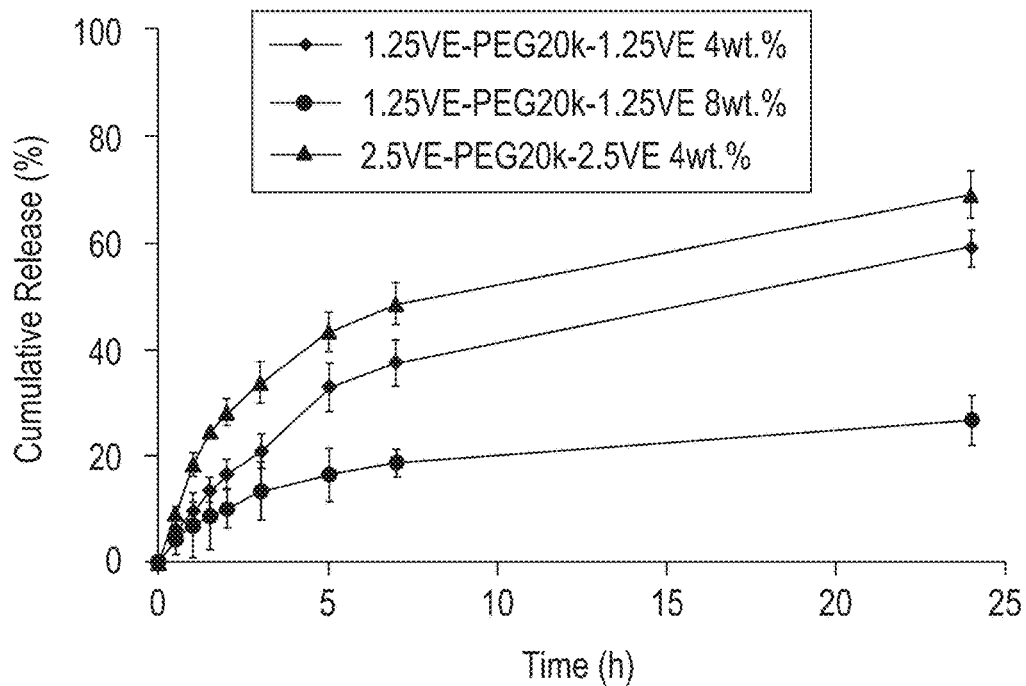
FIG. 4A is a graph showing the release rate of sodium nicotinate from loaded hydrogels:
 a) Example 21 containing 4 wt. % VitE1.25-PEG(20k)-VitE1.25 and 0.3 wt. % sodium nicotinate (diamonds), and
 b) Example 22 containing 8 wt. % VitE1.25-PEG(20k)-VitE1.25 and 0.3 wt. % sodium nicotinate (circles), and
 c) Example 23 containing 4 wt. % VitE2.5-PEG(20k)-VitE2.5 and 0.3 wt. % sodium nicotinate (triangles).

FIG. 4A is a graph plotting the release rate of sodium nicotinate from loaded hydrogels Example 21 (containing 4 wt. % VitE1.25-PEG(20k)-VitE1.25 and 0.3 wt. % sodium nicotinate), Example 22 (containing 8 wt. % VitE1.25-PEG (20k)-VitE1.25 and 0.3 wt. % sodium nicotinate), and Example 23 (containing 4 wt. % VitE2.5-PEG(20k)-VitE2.5 and 0.3 wt. % sodium nicotinate). The loaded hydrogels were studied by immersing the hydrogels in phosphate buffered saline (PBS) (pH 7.4) at 37° C. and measuring the concentration of nicotinate in the PBS solution over time. A higher triblock copolymer concentration results in significantly slower release of sodium nicotinate (FIG. 4A) from the hydrogel, possibly due to the lower porosity of the gel matrix, which results in slower diffusion of the drug molecules through the gel. The hydrophobic/hydrophilic balance of the copolymers also affects the release profiles. From FIG. 4A, 4 wt. % of VitE2.5-PEG(20k)-VitE2.5 (Example 23) shows faster release of sodium nicotinate compared to 4 wt. % VitE1.25-PEG(20k)-VitE1.25 (Example 21). Without being bound by theory, this is possibly due to the lower hydrophilicity of VitE2.5-PEG(20k)-VitE2.5, which might result in a lower extent of intermolecular hydrogen bonding between the polymer and sodium nicotinate molecules.

Figure 4B:
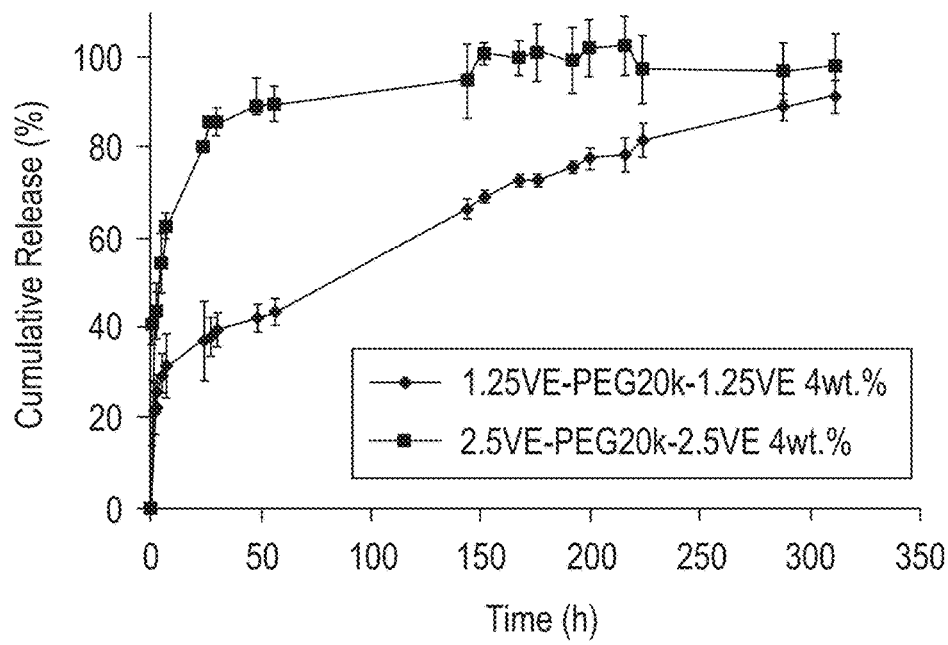
FIG. 4B is a graph showing the release rate of herceptin from loaded hydrogels:
 a) Example 24 containing 4 wt. % VitE1.25-PEG(20k)-VitE1.25 and 1.0 wt. % herceptin and
 b) Example 25 containing 4 wt. % VitE2.5-PEG(20k)-VitE2.5 and 1.0 wt. % herceptin.

Large biomolecules exhibit a similar trend in release profile. FIG. 4B is a graph plotting the release rate of herceptin from loaded hydrogels Example 24 (containing 4 wt. % VitE1.25-PEG(20k)-VitE1.25 and 1.0 wt. % herceptin) and Example 25 (containing 4 wt. % VitE2.5-PEG(20k)-VitE2.5 and 1.0 wt. % herceptin). A large difference in herceptin release rates is observed. Ninety percent of the protein is released in 48 hours from 4 wt. % VitE2.5-PEG (20k)-VitE2.5 (Example 25) hydrogel while the same amount of release from VitE1.25-PEG(20k)-VitE1.25 (Example 24) gel is completed in 312 hours.

Figure 4C:
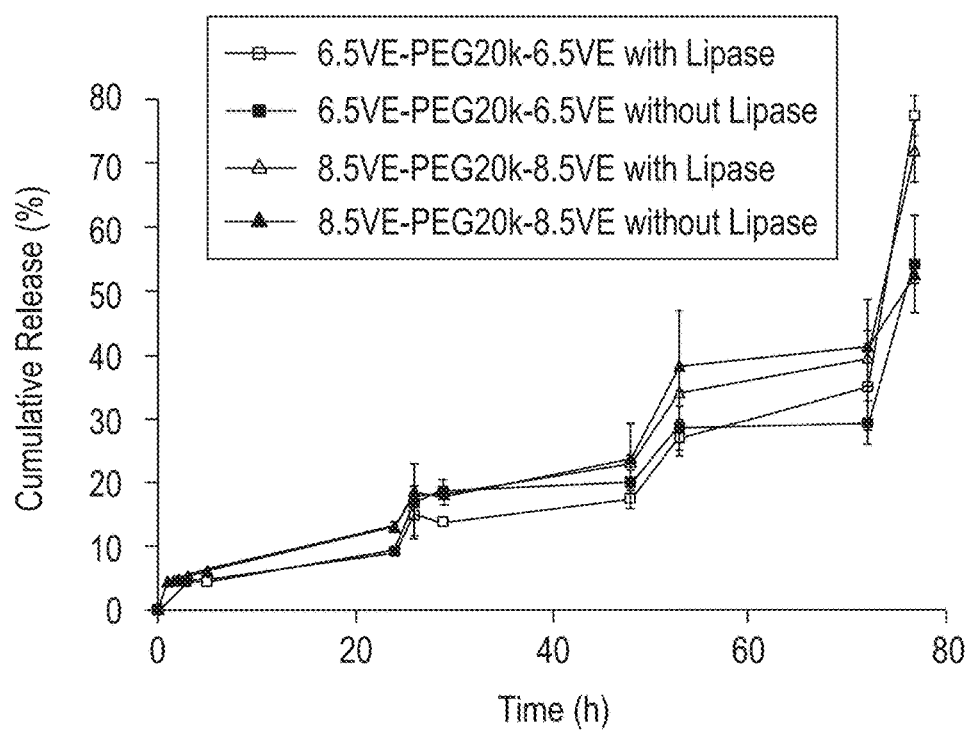
FIG. 4C is a graph showing the release rate of doxycycline (DXY) from organogels:
 a) Example 26 containing 10 wt. % VitE6.5-PEG(20k)-VitE6.5 and 1.0 wt. % doxycycline, with and without added lipase, and
 b) Example 27 containing 10 wt. % VitE8.5-PEG(20k)-VitE8.5 and 1.0 wt. % doxycycline, with and without added lipase.

The release of doxycycline (DXY) was investigated by immersing the organogels in PBS and measuring the concentration of doxycycline in the PBS solution over time. Lipase was added to the release medium in attempt to accelerate the degradation of the organogels. FIG. 4C is a graph plotting the release rate of doxycycline from organogels Example 26 (containing 10 wt. % VitE6.5-PEG(20k)-VitE6.5 and 1.0 wt. % doxycycline) and Example 27 (containing 10 wt. % VitE8.5-PEG(20k)-VitE8.5 and 1.0 wt. % doxycycline), with and without lipase. The presence of lipase did not lead to an increase in the release of doxycycline until hour 77 when close to 20% more antibiotic was released in the enzyme-containing medium with VitE6.5-PEG(20k)-VitE6.5 (Example 26) and VitE8.5-PEG(20k)-VitE8.5 (Example 27). In the presence of lipase, degradation of the organogels could have occurred, resulting in similar amount of antibiotic (~75%) being released from the two polymers. After 77 hours, multiple peaks of the drug showed up on the HPLC chromatogram indicating drug degradation. No further measurements were made.

In Vitro Biocompatibility Study

Figure 5:
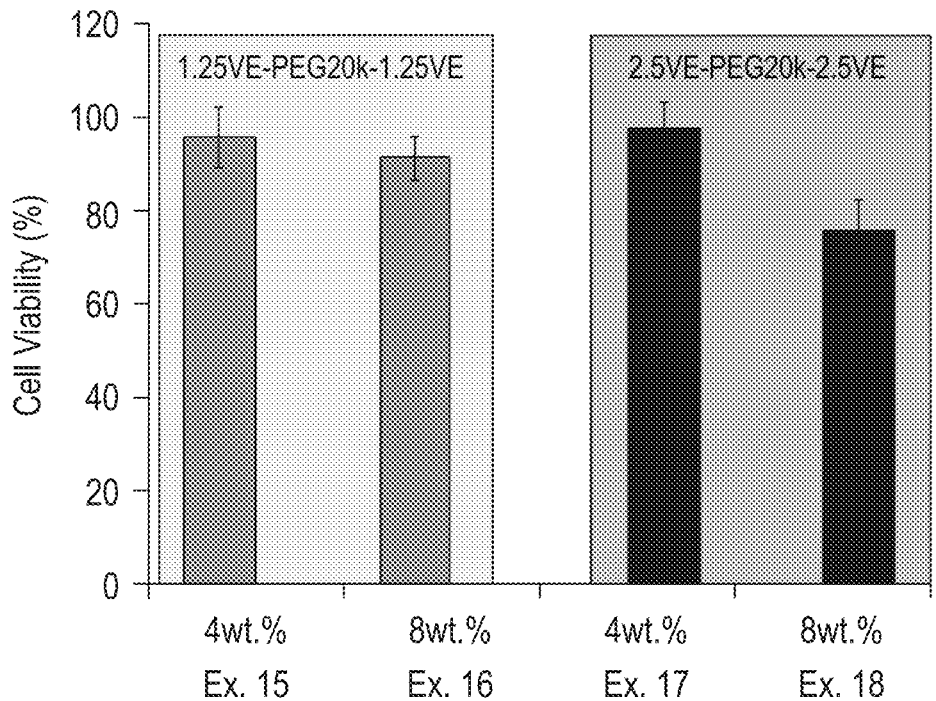
FIG. 5 is a bar graph showing the percentage of viable human dermal fibroblast (HDF) cells after treating the cells with blank hydrogel Examples 15 and 16 (containing 4 wt. % and 8 wt. % VitE1.25-PEG(20k)-VitE1.25, respectively, grey bars) and blank hydrogel Examples 17 and 18 (containing 4 wt. % and 8 wt. % VitE2.5-PEG(20k)-VitE2.5, black bars).

The hydrogels were assessed for their in vitro biocompatibility by culturing human dermal fibroblast (HDF) cells in the presence of hydrogels and organogels for 24 hours. FIG. 5 is a bar graph showing the percentage of viable HDF cells after treatment with blank hydrogel Examples 15 and 16 (containing 4 wt. % and 8 wt. % VitE1.25-PEG(20k)-VitE1.25, respectively) and blank hydrogel Examples 17 and 18 (containing 4 wt. % and 8 wt. % VitE2.5-PEG(20k)-VitE2.5). The hydrogels of lower concentration (4 wt. %) did not exert any toxicity on the cells. However, cell viability with 8 wt. % of VitE2.5-PEG(20k)-VitE2.5 hydrogel (Example 18) was about 75%. Without being bound by theory, this might be due to the high stiffness (G' 12000) and lower porosity of the hydrogel (see FIG. 3D), which leads to slower diffusion of nutrients to the cells and exclusion of metabolites from the cellular environment.

Figure 6:
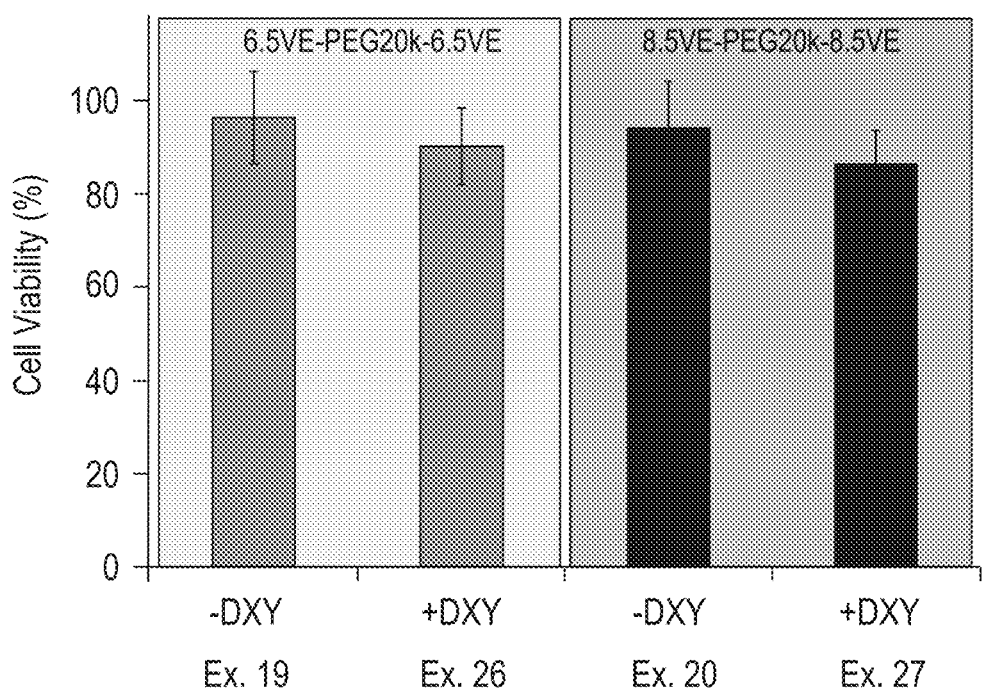
FIG. 6 is a bar graph showing the percentage of viable human dermal fibroblast (HDF) cells after treating the cells with blank organogel Example 19 (containing 10 wt. % VitE6.5-PEG(20k)-VitE6.5), doxycycline loaded hydrogel Example 26 (containing 10 wt. % VitE6.5-PEG(20k)-VitE6.5 and 1 wt. % doxycycline), blank organogel Example 20 (containing 10 wt. % VitE8.5-PEG(20k)-VitE8.5), and doxycycline loaded hydrogel Example 27 (containing 10 wt. % VitE8.5-PEG(20k)-VitE8.5 and 1 wt. % doxycycline).

FIG. 6 is a bar graph showing the percentage of viable human dermal fibroblast (HDF) cells after treating the cells with blank organogel Example 19 (containing 10 wt. % VitE6.5-PEG(20k)-VitE6.5), doxycycline loaded hydrogel Example 26 (containing 10 wt. % VitE6.5-PEG(20k)-VitE6.5 and 1 wt. % doxycycline), blank organogel Example 20 (containing 10 wt. % VitE8.5-PEG(20k)-VitE8.5), and doxycycline loaded hydrogel Example 27 (containing 10 wt. % VitE8.5-PEG(20k)-VitE8.5 and 1 wt. % doxycycline).

Cytotoxicity of Herceptin Delivered by Hydrogels Against Various Cell Lines

Herceptin loaded hydrogel Example 24 (4 wt. % in VitE1.25-PEG(20k)-VitE1.25) was tested against HER2/neu-overexpressing human breast cancer BT474 cells, low HER2/neu-expressing human breast cancer MCF7 cells and human dermal fibroblasts (HDF) to investigate the treatment specificity as well as in vitro biocompatibility of the hydrogel. HER2/neu is also known as c-erbB-2.

Human dermal fibroblasts, MCF7 and BT474 cells were seeded onto 24-well plates at a density of $6 \times 10^4$ cells per well, and cultivated in 500 microliters of growth medium. The plates were then returned to incubators for 24 hours to reach~70% confluency before treatment. When the desired cell confluency was reached, the spent growth medium was removed from each well and replaced with 500 microliters of fresh medium together with 50 microliters of the hydrogel in a Transwell insert and incubated for either 48 or 120 hours. Each condition was tested in four replicates. When the treatment was completed, the culture medium was removed and 50 microliters of MTT solution was added with 500 microliters of fresh medium. The plates were then returned to the incubator and maintained in 5% $CO_2$, at 37° C., for a further 3 hours. The growth medium and excess MTT in each well were then removed. 600 microliters of DMSO was added to each well to dissolve the internalised purple formazan crystals. An aliquot of 100 microliters was taken from each well and transferred to a new 96-well plate. The plates were then assayed at 550 nm and reference wavelength of 690 nm using a microplate reader (Tecan, U.S.A.). The absorbance readings of the formazan crystals were taken to be those at 550 nm subtracted by those at 690 nm. The results were expressed as a percentage of the absorbance of the control cells without any treatment.

Figure 7:
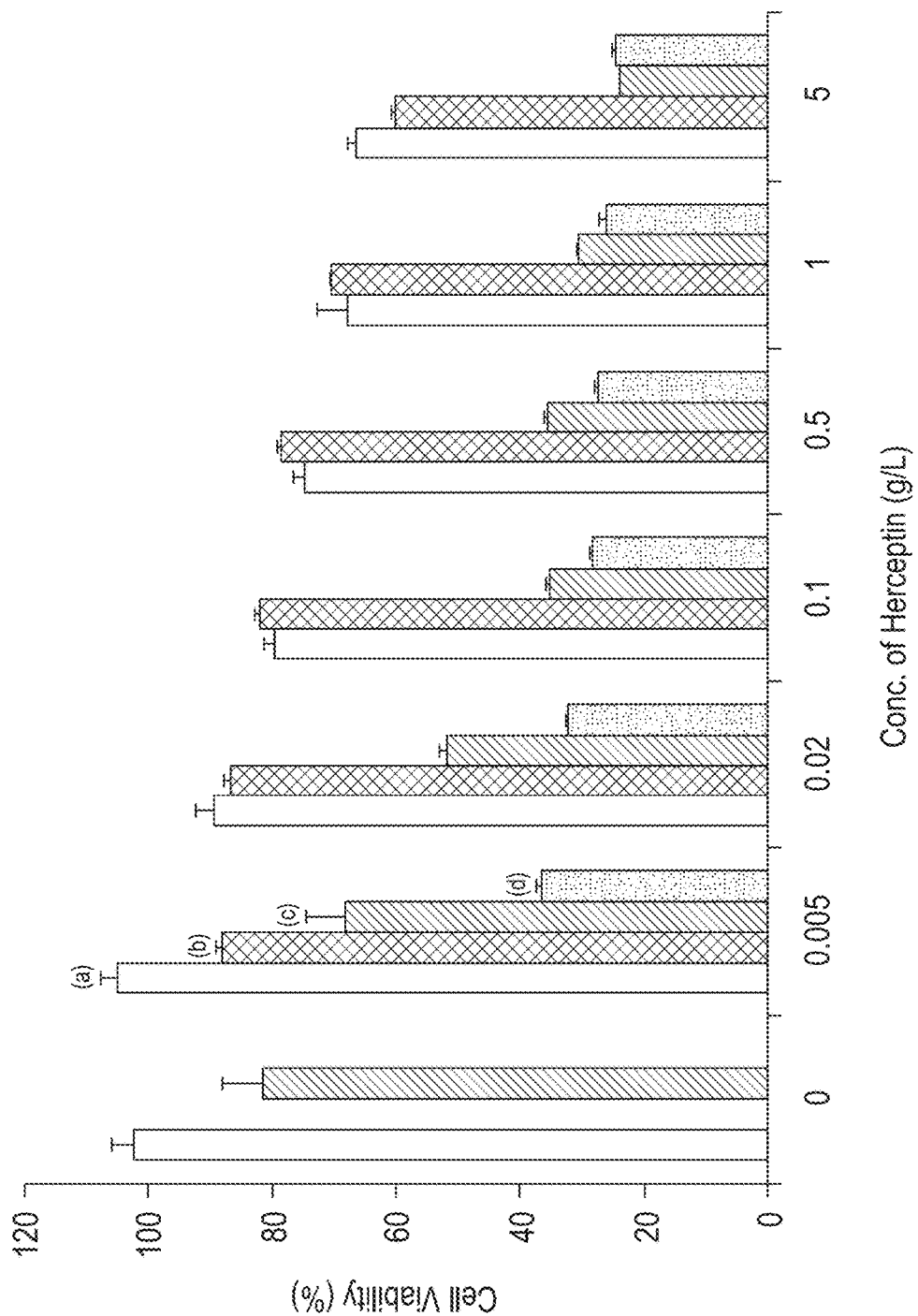
FIG. 7 is a bar graph showing the percentage of viable HER2/neu-overexpressing human breast cancer BT474 cells as a function of herceptin concentration after treating the cells with:
 (a) herceptin loaded hydrogel containing 4 wt. % VitE1.25-PEG(20k)-VitE1.25 for 48 hours,
 (b) herceptin solution for 48 hours,
 (c) herceptin loaded hydrogel containing 4 wt. % VitE1.25-PEG(20k)-VitE1.25 for 120 hours, and
 (d) herceptin solution for 120 hours, each performed using a herceptin concentration of 0.0005 wt. %, 0.002 wt. %, 0.01 wt. %, 0.05 wt. %, 0.1 wt. %, and 0.5 wt. %. The herceptin loaded hydrogels were prepared using the procedure of Example 24.

FIG. 7 is a bar graph showing the percent of viable HER2/neu-overexpressing human breast cancer BT474 cells as a function of herceptin concentration after treating the cells with (a) herceptin loaded hydrogel (4 wt. % in VitE1.25-PEG(20k)-VitE1.25) for 48 hours, (b) herceptin solution for 48 hours, (c) herceptin loaded hydrogel (4 wt. % in VitE1.25-PEG(20k)-VitE1.25) for 120 hours, (d) and herceptin solution for 120 hours, each performed using a herceptin concentration of 0.0005 wt. %, 0.002 wt. %, 0.01 wt. %, 0.05 wt. %, 0.1 wt. %, and 0.5 wt. %. The herceptin loaded hydrogels were prepared using the procedure of Example 24. FIG. 7 shows that 48 hour treatment was insufficient for herceptin to exert sufficient killing effect on BT474 cells. About 65% of the BT474 cells still remained viable at even at the highest herceptin concentration tested (i.e., 5 g/L). Interestingly, when the treatment was extended to 120 hours, the IC50 of herceptin delivered using the hydrogel was drastically reduced to 0.02 g/L, whereas the blank hydrogel has minimal cytotoxicity. IC50 is the half maximal inhibitory concentration, and is a quantitative measure of how much of a particular drug or other substance (inhibitor) is needed to inhibit a given biological process (or component of a process, i.e., an enzyme, cell, cell receptor or microorganism) by half. The IC50 of the solution formulation of herceptin was lower, <0.005 g/L. Without being bound by theory, the higher IC50 value of the hydrogel formulation might be due to the release kinetics of herceptin from the hydrogel. About 50% of the initial amount of herceptin was released by 5 days (i.e., 120 hours), and furthermore, the cumulative cytotoxic effect would also be reduced over the 5-day period as compared to the bolus delivery of herceptin solution. The herceptin-loaded hydrogel was highly effective in killing BT474 cells at high herceptin concentrations ($\geq 1$ g/L), where more than 70% of the cells were killed in 120 hours. Pharmacokinetic studies have shown that herceptin has a half-life of 6.2 to 8.3 days, and with the sustained release profile of herceptin from the hydrogel for more than 2 weeks, it is anticipated that the hydrogel would be able to deliver a continuous supply of antibody in vivo and eradicate HER2+tumors.

Figure 8:
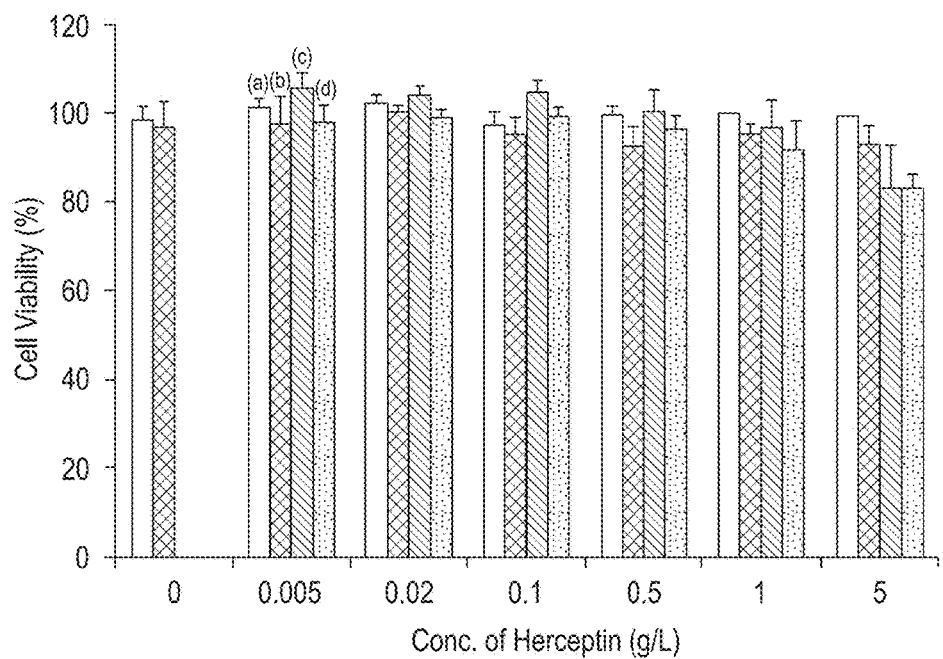
FIG. 8 is a bar graph showing the viability of MCF7 cells as a function of herceptin concentration when treated with:
 (a) herceptin loaded hydrogel containing 4 wt. % VitE1.25-PEG(20k)-VitE1.25 for 48 hours,
 (b) herceptin solution for 48 hours,
 (c) herceptin loaded hydrogel containing 4 wt. % VitE1.25-PEG(20k)-VitE1.25 for 120 hours, and
 (d) herceptin solution for 120 hours, each performed using a herceptin concentration of 0.0005 wt. %, 0.002 wt. %, 0.01 wt. %, 0.05 wt. %, 0.1 wt. %, and 0.5 wt. %. The herceptin loaded hydrogels were prepared using the procedure of Example 24.

FIG. 8 is a bar graph showing the viability of MCF7 cells as a function of herceptin concentration when treated with (a) herceptin loaded hydrogel (4 wt. % in VitE1.25-PEG(20k)-VitE1.25) for 48 hours, (b) herceptin solution for 48 hours, (c) herceptin loaded hydrogel (4 wt. % in VitE1.25-PEG(20k)-VitE1.25) for 120 hours, (d) and herceptin solution for 120 hours, each performed using a herceptin concentration of 0.0005 wt. %, 0.002 wt. %, 0.01 wt. %, 0.05 wt. %, 0.1 wt. %, and 0.5 wt. %. Herceptin loaded hydrogels were prepared using the procedure of Example 24. With MCF7 cells, herceptin delivered either in the hydrogel or solution formulation shows negligible cytotoxic effect with more than 80% cell viability even after 120 hours treatment at up to herceptin concentration of 5 g/L. This demonstrates that the herceptin treatment was specific towards HER2/neu-overexpressing cancer cells.

Figure 9:
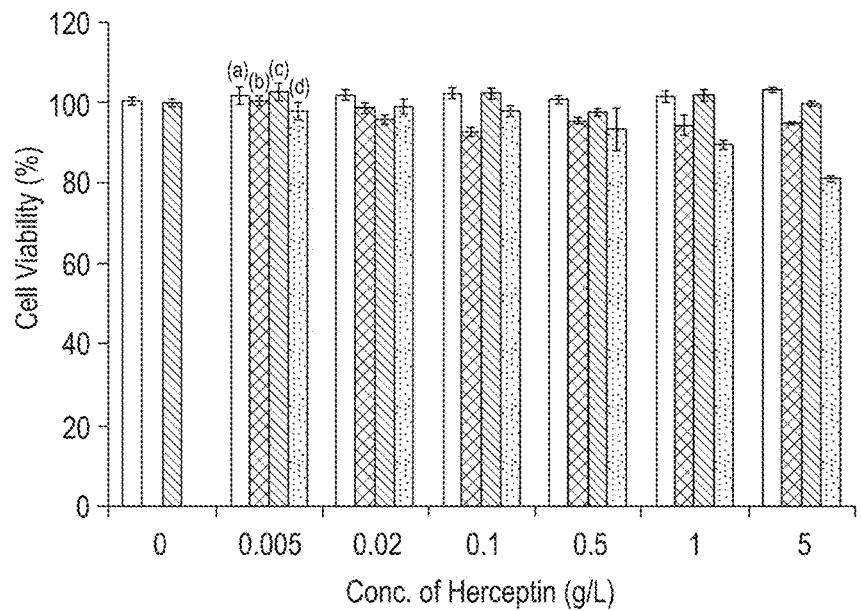
FIG. 9 is a bar graph showing the viability of human dermal fibroblast (HDF) cells as a function of herceptin concentration when treated with:
 (a) herceptin loaded hydrogel containing 4 wt. % VitE1.25-PEG(20k)-VitE1.25 for 48 hours,
 (b) herceptin solution for 48 hours,
 (c) herceptin loaded hydrogel containing 4 wt. % VitE1.25-PEG(20k)-VitE1.25 for 120 hours, and
 (d) herceptin solution for 120 hours, each performed using a herceptin concentration of 0.0005 wt. %, 0.002 wt. %, 0.01 wt. %, 0.05 wt. %, 0.1 wt. %, and 0.5 wt. %. The herceptin loaded hydrogels were prepared using the procedure of Example 24.

FIG. 9 is a bar graph showing the viability of human dermal fibroblast (HDF) cells as a function of herceptin concentration when treated with (a) herceptin loaded hydrogel (4 wt. % in VitE1.25-PEG(20k)-VitE1.25) for 48 hours, (b) herceptin solution for 48 hours, (c) herceptin loaded hydrogel (4 wt. % in VitE1.25-PEG(20k)-VitE1.25) for 120 hours, (d) and herceptin solution for 120 hours, each performed using a herceptin concentration of 0.0005 wt. %, 0.002 wt. %, 0.01 wt. %, 0.05 wt. %, 0.1 wt. %, and 0.5 wt. %. The herceptin loaded hydrogels were prepared using the procedure of Example 24. The antibody solution showed slight cytotoxicity against HDF at 5 g/L after 120 hours of treatment. It is possible that the interaction of herceptin with the epidermal growth factor receptors (EGFR/ErbB) on the HDR cells causes slight hinderence to HDF cell proliferation. Herceptin-loaded hydrogel did not show significant cytotoxicity at 5 g/L due to the sustained release of herceptin (only ~60% herceptin released from the gel after 120 hours). Furthermore, the blank hydrogels showed no cytotoxicity toward HDF even after 120 hours of treatment, indicating in vitro biocompatibility.

In Vivo Biocompatibility and Gel Degradation Studies

In order for the vitamin E-functionalized polymeric hydrogel to serve as drug delivery depot, it is crucial that the hydrogel be biocompatible in vivo. To evaluate this property, subcutaneous injection of the blank hydrogel Example 15 (4 wt. % VitE1.25-PEG(20k)-VitE1.25) was carried out in mice.

All animal experiments were conducted in accordance with the approved protocol from the Institutional Animal Care and Use Committee (IACUC) at the Biological Resource Centre of Singapore. Female BALB/c mice, weighing 20 g to 25 g were injected subcutaneously with 150 microliters of blank hydrogel Example 15 (4 wt. % VitE1.25-PEG(20k)-VitE1.25). At predetermined periods, mice were sacrificed and the hydrogel and its surrounding tissue were isolated. For histological examination, samples were fixed in 4% neutral buffered formalin and then stained with hematoxylin/eosin (H&E) using standard techniques. To identify the inflammatory cells populated in the subcutaneous tissue and hydrogel, immunohistochemical staining was carried out using a monoclonal rat anti-mouse antibody CD45R (BD Biosciences, U.S.A.) that recognizes the leukocyte common antigen (CD45). The slides were counterstained with hematoxylin/eosin (H&E) to visualize cell nuclei and examined using a stereomicroscope (Nikon, U.S.A.).

Figure 10:
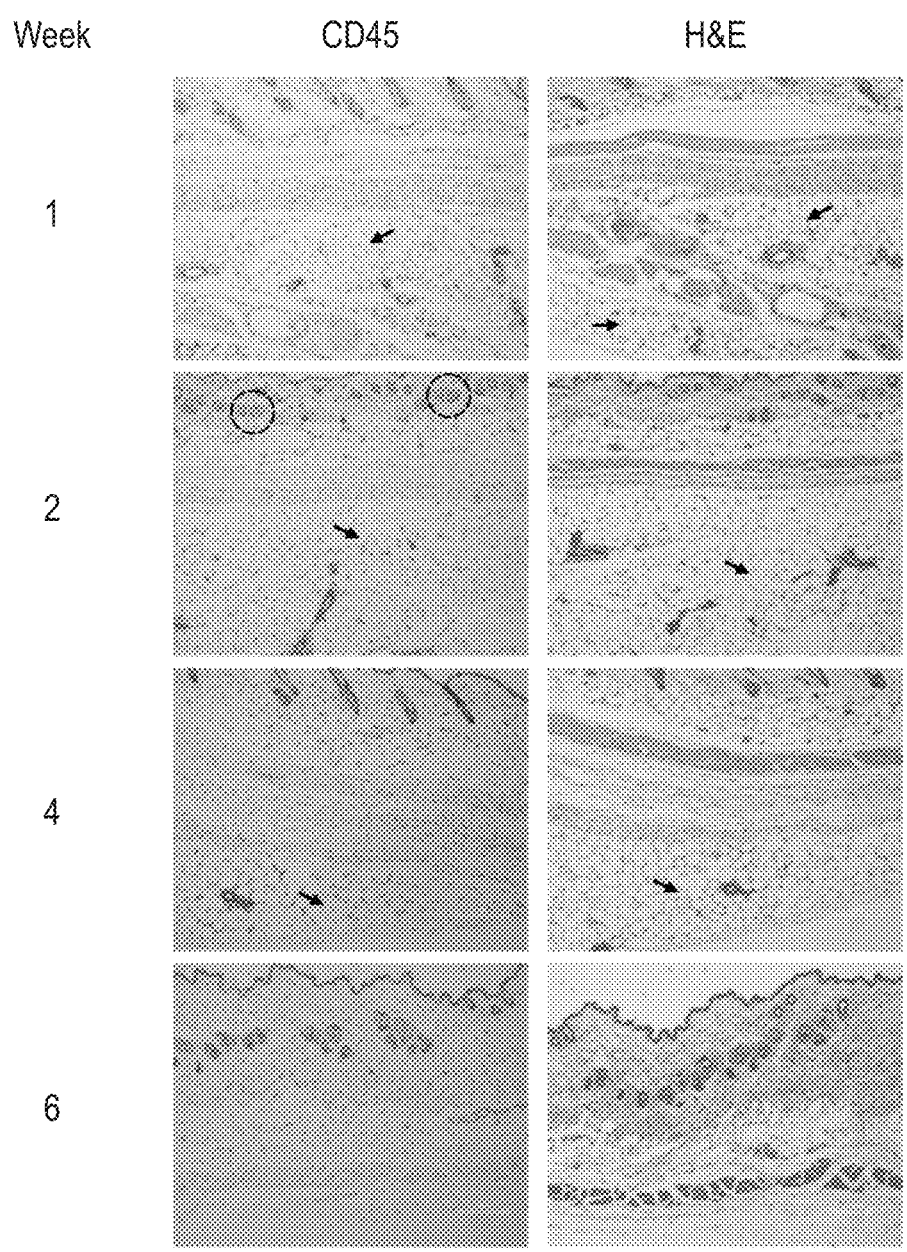
FIG. 10 is a series of optical photomicrographs of CD45 and haematoxylin/eosin (H&E) stained mice tissue after treatment with blank hydrogel Example 15 (4 wt. % VitE1.25-PEG(20k)-VitE1.25), retrieved at 1, 2, 4 and 6 weeks post injection. Arrows indicate the region where hydrogel is present. At week 6, the hydrogel has mostly degraded and could not be distinctly identified. The scale bar represents 200 micrometers.

Histological sections of the hydrogel treated and surrounding mice tissue were examined at 1, 2, 4 and 6 weeks post injection (FIG. 10, optical photomicrographs of stained tissue). Within 2 weeks post injection, the hydrogel remained mostly intact (arrows in FIG. 10) and some inflammatory cells (indicated by darker DAB stains shown in the dashed circles) had infiltrated into the hydrogel. At 4 weeks, the thickness of the hydrogel had reduced, indicating degradation of the hydrogel. By 6 weeks, the hydrogel had mostly degraded and there was a noticeable reduction in the number of CD45-positive cells in the hydrogel and surrounding tissue. This significant reduction in the number of leukocytes (inflammation-mediating cells) indicates that only mild in vivo tissue response occurred with the administration of hydrogel and the inflammatory response was only temporary and did not progress to a chronic phase.

Biodistribution of Herceptin Delivered Using Different Formulations

To evaluate its biodistribution, herceptin was first labeled using ALEXA FLUOR 790 (Invitrogen, U.S.A.). The ALEXA FLUOR dye, with a tetrafluorophenyl (TFP) ester moiety, was added to the antibody in a molar ratio of 15:1. The reaction was carried out at room temperature for 30 minutes. Purification of the fluorescent conjugate was carried out via ultracentrifugation. The conjugate was then analyzed using the NANODROP ND-1000 spectrophotometer (NanoDrop Technologies, U.S.A.) and the degree of labeling was determined to be 1.45 moles ALEXA FLUOR dye per mole of herceptin.

BT474 tumor-bearing female BALB/c nude mice were used for this study. The mice were divided into 3 groups and administrated with herceptin in different formulations: (1) a herceptin loaded hydrogel Example 24 (containing 4 wt. % VitE1.25-PEG(20k)-VitE1.25 hydrogel and 0.5 wt. % herceptin) ("Herceptin-loaded hydrogel, S.C."), (2) a herceptin solution injected subcutaneously at approximately 1 cm away from the tumor site ("Herceptin solution, S.C."), and (3) a herceptin solution injected intravenously ("Herceptin solution, I.V."). For preparation of (2) and (3) herceptin was dissolved in HPLC grade water at a concentration of 5 g/L.

Anesthetic animals were placed on an animal plate heated to 37° C. The near-infrared fluorescence was imaged using the ICG filter pairs and exposure time was set to 1 sec. Scans were performed at 1, 2, 3, 6, 8, 10 and 13 days post administration. The mice were sacrificed on Day 13 and organs involved in drug clearance and metabolism as well as tumor tissue were excised and imaged using IVIS (Caliper Life Science, U.S.A.).

Figure 11:
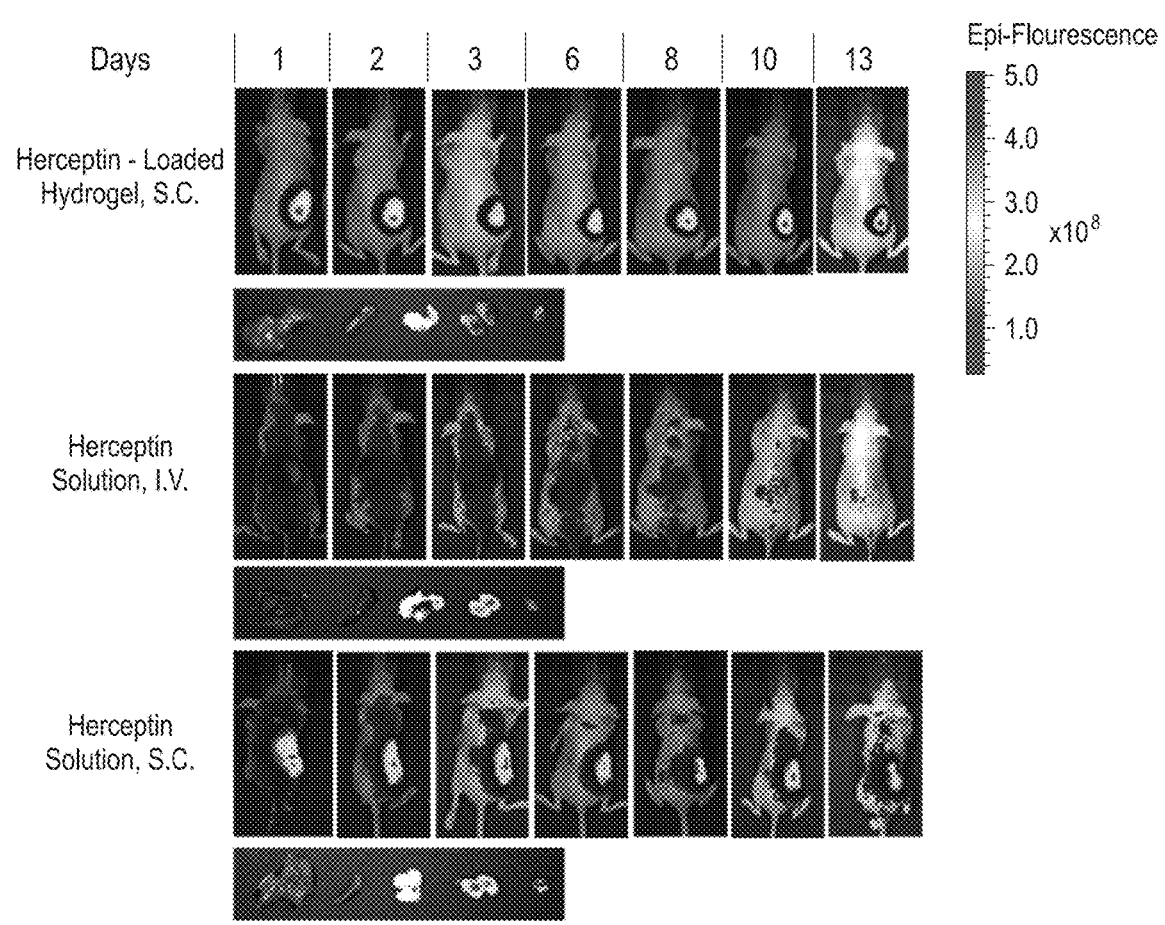
FIG. 11 is a series of mouse drawings showing the biodistribution of ALEXA FLUOR 790-labeled herceptin within BT474-tumor bearing mice over a 13 day period. The herceptin was delivered once to the mice in three ways: i) using herceptin loaded hydrogel (Example 24) delivered subcutaneously ("Herceptin-loaded hydrogel, S.C."), ii) herceptin solution delivered intravenously ("Herceptin solution, I.V."), and iii) herceptin solution delivered subcutaneously ("Herceptin solution, S.C."). On Day 13, the mice were sacrificed and organs involved in drug clearance and metabolism as well as tumor tissue were excised and imaged. From left: liver, spleen, lungs, kidneys, tumor.

FIG. 11 is a series of mouse drawings showing the biodistribution of ALEXA FLUOR 790-labeled herceptin within the mice over a 13 day period. Comparison between the subcutaneous delivery using the hydrogel and the intravenous injection in solution shows that the subcutaneous injection was more favorable. The intravenous injection method resulted in herceptin accumulation mainly within organs such as kidneys, liver and lungs, but only a very little amount in the tumor tissue. When herceptin solution was injected subcutaneously at about 1 cm away from the tumor site, the antibody accumulated to a greater extent in the tumor compared to that in the intravenous injection case. This is most likely due to the proximity to the tumor tissue which allowed accessibility for herceptin to diffuse to the tumor. However, herceptin was still able to enter the circulation system and experience similar biodistribution as the intravenous administration. On the other hand, the hydrogel formulation provided localized delivery of herceptin, leading to a high amount of herceptin accumulation within the tumor and very little amount in the other organs. The biodistribution patterns of various formulations will likely influence their anti-tumor efficacy.

VIII. In Vivo Anti-Tumor Efficacy

To understand the therapeutic efficacy of herceptin delivery via different routes of administration, herceptin-loaded hydrogel Example 24 (4 wt. % in VitE1.25-PEG(20k)-VitE1.25 and 1 wt. % herceptin) injected subcutaneously (S.C.) was compared to both intravenous (I.V.) and subcutaneous administration of herceptin solution in the BT474-tumor bearing mouse model. The mice were divided into 5 groups consisting of: control injected on the first day of treatment (Day 0) with HPLC grade water (S.C.); herceptin in solution delivered intravenously (I.V.); herceptin in solution delivered subcutaneously (S.C.); blank hydrogel (Example 15) delivered subcutaneously (S.C.) and herceptin-loaded hydrogel (Example 24) delivered subcutaneously (S.C.). Herceptin solution was prepared by using HPLC grade water to dissolve herceptin at 5 g/L. Subcutaneous injections were performed once per mouse at about 1 cm away from tumor sites. The administrated dosage of herceptin was 30 mg/kg in 150 microliters for all formulations.

Female BALB/c nude mice, weighing 18 g to 22 g were injected subcutaneously with 200 microliters of a cell suspension (1:1 with Matrigel) (BD Biosciences, U.S.A.) containing $5 \times 10^6$ BT474 cells. Three weeks after inoculation (when the tumor volume was 100 mm$^3$ to 120 mm$^3$), the tumor-bearing mice were randomly divided into several groups (7 to 10 mice per group).

In a first experiment, Group 1 mice were used as non-treated control, group 2 and 3 mice were given intravenous (30 mg/kg) and subcutaneous (150 microliters) injections of herceptin solution of concentration of 1.25 g/L in HPLC grade water, respectively, group 4 and group 5 mice were subcutaneous injections (150 microliters, 30 mg/kg) of blank hydrogel Example 15 (4 wt. % in VitE1.25-PEG(20k)-VitE1.25) and herceptin loaded hydrogel Example 24 (4 wt. % VitE1.25-PEG(20k)-VitE1.25 and 1.0 wt. % herceptin), respectively, at ~1 cm away from the tumor site. All mice were injected only once on the first day of treatment (Day 0).

In a second experiment, Group 1b mice were used as nontreated control, Group 2b and 3b mice were given 4 doses of weekly intravenous and subcutaneous injections of herceptin (4×10 mg/kg), respectively while the Group 4b mice were injected once subcutaneously with herceptin-loaded hydrogel Example 24 (4 wt. % VitE1.25-PEG(20k)-VitE1.25 and 1.0 wt. % herceptin) at a dosage of 40 mg/kg on the first day of treatment (Day 0), respectively. For improved clinical relevance, the subcutaneous injections of herceptin solution and herceptin-loaded hydrogel were carried out at a remote site, ~4 cm away from the tumor. The tumor size was measured by calipers in two orthogonal diameters and the volume was calculated as L×W2/2, where L and W are the major and minor diameters respectively. At the end of the treatment, a two-tailed Student's t test was used to statistically evaluate the difference in tumor volume and P≤0.05 was considered to indicate a statistically significant difference. In addition, the toxicities of the different formulations were evaluated by monitoring the change in mouse body weight over the course of treatment.

Figure 12A:
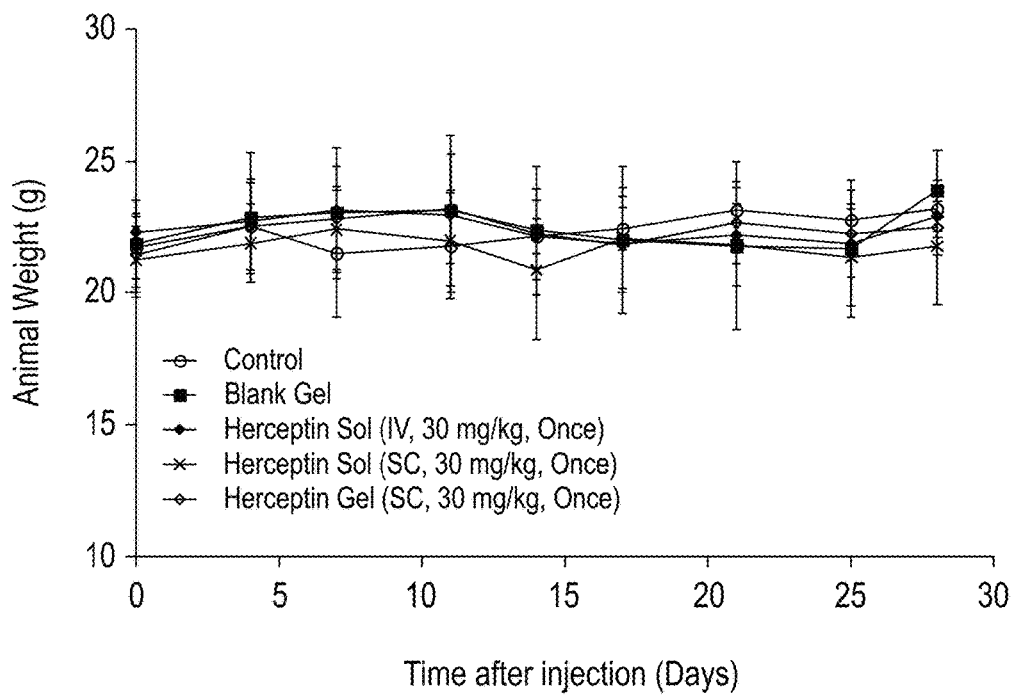
FIG. 12A is a graph showing the change in body weight of BT474-tumor bearing mice after one injection using various herceptin formulations, including blank hydrogel Example 15 (4 wt. % VitE1.25-PEG(20k)-VitE1.25) delivered subcutaneously ("Blank Gel") herceptin solution delivered intravenously ("Herceptin Sol (IV, 30 mg/kg, Once)"), herceptin solution delivered subcutaneously ("Herceptin Sol (SC, 30 mg/kg, Once)"), and herceptin loaded hydrogel Example 24 (4 wt. % VitE1.25-PEG(20k)-VitE1.25 and 1.0 wt. % herceptin) delivered subcutaneously ("Herceptin Gel (SC, 30 mg/kg, Once")). The herceptin dosage was 30 mg/kg.

FIG. 12A is a graph showing the change in body weight of BT474-tumor bearing mice after one injection using various herceptin formulations, including blank hydrogel Example 15 (4 wt. % VitE1.25-PEG(20k)-VitE1.25) delivered subcutaneously ("Blank Gel") herceptin solution delivered intravenously ("Herceptin Sol (IV, 30 mg/kg, Once")), herceptin solution delivered subcutaneously ("Herceptin Sol (SC, 30 mg/kg, Once")), and herceptin loaded hydrogel Example 24 (4 wt. % VitE1.25-PEG(20k)-VitE1.25 and 1.0 wt. % herceptin) delivered subcutaneously ("Herceptin Gel (SC, 30 mg/kg, Once")). The herceptin dosage was 30 mg/kg. No weight loss was observed for all mice during the course of treatment, indicating good tolerance to all treatment conditions.

Figure 12B:
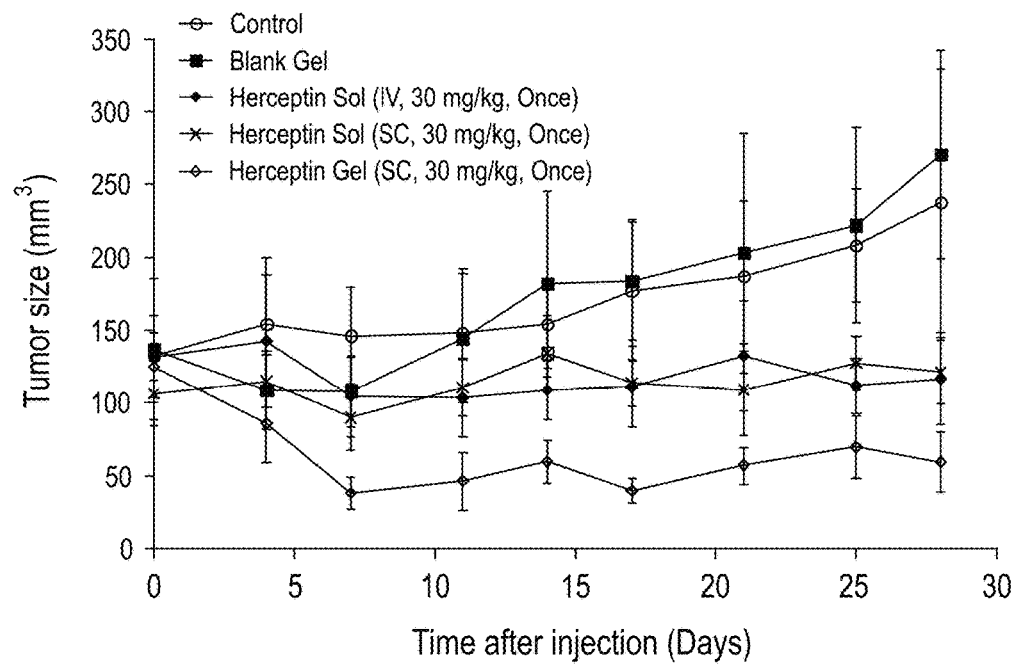
FIG. 12B is a graph showing change in tumor size of BT474-tumor bearing mice after one injection using various herceptin formulations, including blank hydrogel Example 15 (4 wt. % VitE1.25-PEG(20k)-VitE1.25) delivered subcutaneously ("Blank Gel") herceptin solution delivered intravenously ("Herceptin Sol (IV, 30 mg/kg, Once")), herceptin solution delivered subcutaneously ("Herceptin Sol (SC, 30 mg/kg, Once")), and herceptin loaded hydrogel Example 24 (4 wt. % VitE1.25-PEG(20k)-VitE1.25 and 1.0 wt. % herceptin) delivered subcutaneously ("Herceptin Gel (SC, 30 mg/kg, Once")). The herceptin dosage was 30 mg/kg.

FIG. 12B is a graph showing change in tumor size of BT474-tumor bearing mice after one injection using various herceptin formulations, including blank hydrogel Example 15 (4 wt. % VitE1.25-PEG(20k)-VitE1.25) delivered subcutaneously ("Blank Gel") herceptin solution delivered intravenously ("Herceptin Sol (IV, 30 mg/kg, Once")), herceptin solution delivered subcutaneously ("Herceptin Sol (SC, 30 mg/kg, Once")), and herceptin loaded hydrogel Example 24 (4 wt. % VitE1.25-PEG(20k)-VitE1.25 and 1.0 wt. % herceptin) delivered subcutaneously ("Herceptin Gel (SC, 30 mg/kg, Once")). The herceptin dosage was 30 mg/kg. Measurement of tumor size with time reveals that the tumor growth inhibition by the solution and hydrogel formulations were different. Mice treated with blank hydrogel Example 15 (4 wt. % VitE1.25-PEG(20k)-VitE1.25, "Blank Gel") had similar average tumor volume compared to the control group (P=0.56). This indicates that the blank hydrogel Example 15 did not exert any cytotoxic effect on the tumors. In sharp contrast, the herceptin-loaded hydrogel Example 24 (4 wt. % VitE1.25-PEG(20k)-VitE1.25 and 1.0 wt. % herceptin, "Herceptin Gel (SC, 30 mg/kg, Once") reduced the tumor by about 77% (P=0.01) compared to the control group. It is noteworthy that mice treated with the herceptin loaded hydrogel were the only group that showed tumor shrinkage. This can be seen by comparing the tumor size on the initial and final day of treatment course (P<0.001). Furthermore, the anti-tumor efficacy was much more pronounced with the hydrogel treatment compared to treatment using herceptin solutions delivered intravenously ("Herceptin Sol (IV, 30 mg/kg, Once")) or subcutaneously ("Herceptin Sol (SC, 30 mg/kg, Once")), with P values <0.005. Without being bound by theory, this is attributed to the herceptin-containing hydrogel having higher localized herceptin concentration at the tumor site over a longer period of time (as shown in FIG. 11), which enables herceptin to exert a more cytotoxic effect against the cancer cells.

Histological Analysis

At 28 days post injection of the herceptin formulations, the mice were sacrificed and the tumors as well as normal tissues (heart, lung, liver and kidney) were individually excised and dissected. For histological examination, the samples were fixed in 4% neutral buffered formalin and then stained with hematoxylin/eosin (H&E) using standard techniques. Apoptotic cells of tumor samples were identified using Terminal Transferase dUTP Nick-End Labeling (TUNEL) assay. The slides were counterstained with hematoxylin to visualize nuclei and examined using a stereomicroscope (Nikon, U.S.A.).

Figure 13:
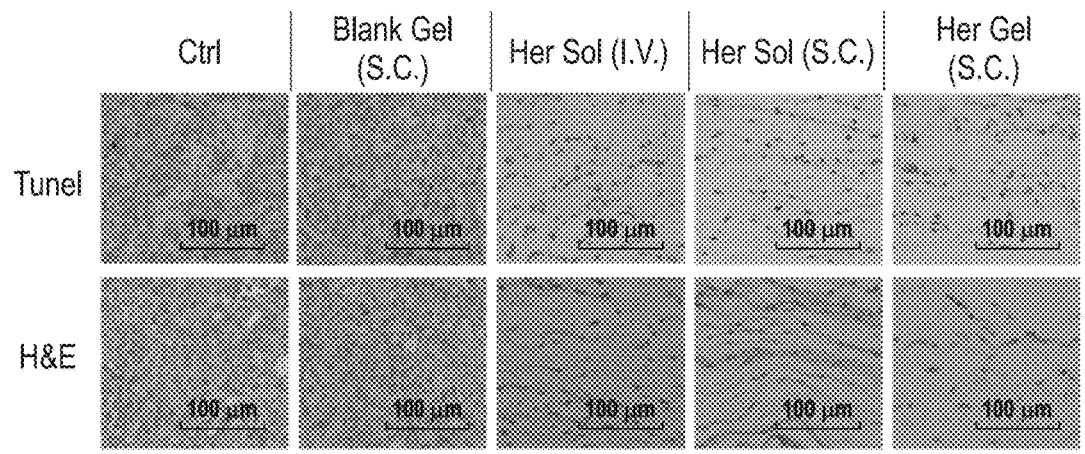
FIG. 13 is a series of photomicrographs showing tumor cells of BT474-tumor bearing mice after terminal deoxynucleotidyl transferase dUTP nick end labeling (TUNEL) staining at 28 days after one injection using various herceptin formulations, including blank hydrogel Example 15 (4 wt. % VitE1.25-PEG(20k)-VitE1.25) delivered subcutaneously ("Blank Gel (S.C.)"), herceptin solution delivered intravenously ("Her Sol (I.V.)"), herceptin solution delivered subcutaneously ("Her Sol (S.C.)"), and herceptin loaded hydrogel Example 24 (4 wt. % VitE1.25-PEG(20k)-VitE1.25 and 1.0 wt. % herceptin) delivered subcutaneously ("Her Gel (S.C.)"). The herceptin dosage was 30 mg/kg. The scale bar represents 100 micrometers. The tumor cells treated with herceptin, regardless of the formulation used, were mostly apoptotic, indicating that anti-tumor mechanism was based on herceptin-induced apoptosis.

The TUNEL assay reveals apoptotic cells (as a brown 3,3'-diaminobenzidine (DAB) stain) by detecting DNA fragmentation resulting from apoptosis. FIG. 13 is a series of photomicrographs showing tumor cells of BT474-tumor bearing mice after terminal deoxynucleotidyl transferase dUTP nick end labeling (TUNEL) staining at 28 days after one injection using various herceptin formulations, including blank hydrogel Example 15 (4 wt. % VitE1.25-PEG(20k)-VitE1.25) delivered subcutaneously ("Blank Gel (S.C.)"), herceptin solution delivered intravenously ("Her Sol (I.V.)"), herceptin solution delivered subcutaneously ("Her Sol (S.C.)"), and herceptin loaded hydrogel Example 24 (4 wt. % VitE1.25-PEG(20k)-VitE1.25 and 1.0 wt. % herceptin) delivered subcutaneously ("Her Gel (S.C.)"). The herceptin dosage was 30 mg/kg. The scale bar represents 100 micrometers. The color version of the photomicrographs of FIG. 13 shows that tumor cells treated with herceptin, regardless of the formulation used, were mostly apoptotic, indicating that anti-tumor mechanism was based on herceptin-induced apoptosis. H&E staining shows that treatment using herceptin-loaded hydrogel resulted in fewer cells remaining. This further illustrates the higher anti-tumor efficacy of the subcutaneous delivered herceptin-loaded hydrogel.

In addition, the anti-tumor efficacy of one-time subcutaneous injection of herceptin-loaded hydrogel was compared to weekly intravenous and subcutaneous injections of herceptin solution. Importantly, the subcutaneous injections were done at a remote site (about 4 cm away from the tumor) to increase clinical relevance of the study. The total herceptin dosage was 40 mg/kg in each group. At the end of the treatment, a two-tailed Student's t test was used to statistically evaluate the differences in tumor volume and P<0.05 was considered to indicate a statistically significant difference.

Figure 14A:
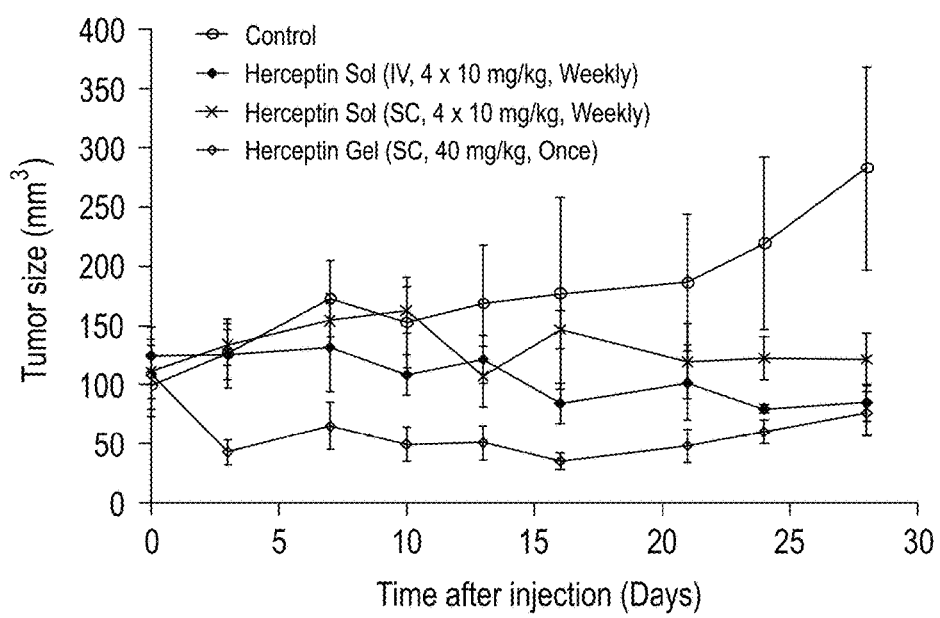
FIGS. 14A and 14B are graphs showing the changes in tumor size (FIG. 14A) and body weight (FIG. 14B) of BT474-tumor bearing mice after four weekly administrations of herceptin solution delivered intravenously ("Herceptin Sol (IV, 4×10 mg/kg, Weekly") and subcutaneously ("Herceptin Sol (IV, 4×10 mg/kg, Weekly") compared to herceptin loaded hydrogel (Example 24) delivered once subcutaneously ("Herceptin Gel (SC, 40 mg/kg, Once"). The total herceptin dosage was 40 mg/kg in each group.
Figure 14B:
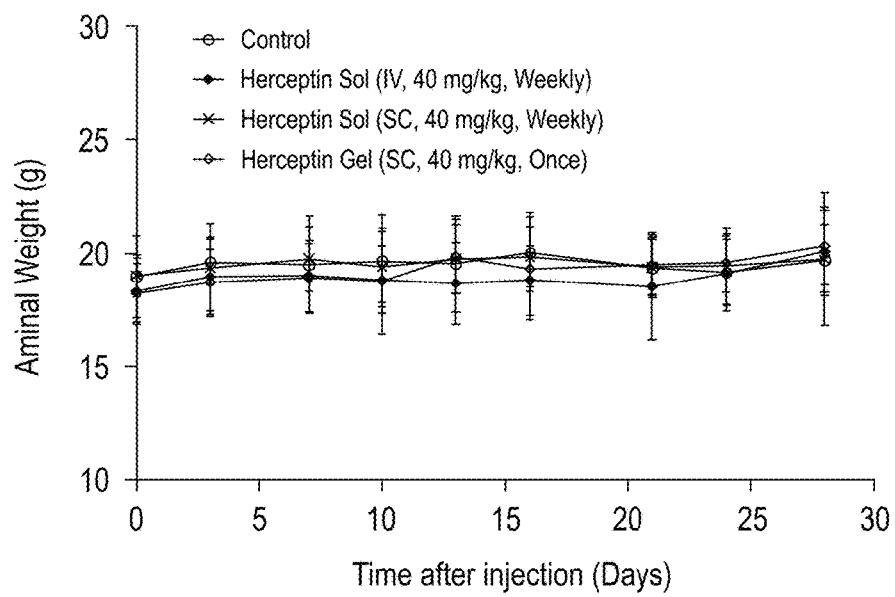

FIGS. 14A and 14B are graphs showing the changes in tumor size (FIG. 14A) and mouse body weight (FIG. 14B) of BT474-tumor bearing mice after four weekly administrations of herceptin solution delivered intravenously ("Herceptin Sol (IV, 4×10 mg/kg, Weekly") and subcutaneously ("Herceptin Sol (IV, 4×10 mg/kg, Weekly"), compared to herceptin loaded hydrogel (Example 24) delivered once subcutaneously ("Herceptin Gel (SC, 40 mg/kg, Once"). For the group treated with herceptin solution, the tumor remained similar in size over the 28 day period.

The tumor reduction provided by the subcutaneously delivered herceptin-loaded hydrogel Example 24 (4 wt. % VitE1.25-PEG(20k)-VitE1.25 and 1.0 wt. % herceptin) is significantly greater compared to the subcutaneously delivered herceptin solution (FIG. 14A). For the herceptin solution group, tumors remained similar in size throughout the entire course of treatment, whereas for the hydrogel treated group, the tumor decreased by 30% (P=0.03) by the end of the treatment. Mouse body weight also remained relatively constant for each sample tested (FIG. 14B). Without being bound by theory, the superior anti-tumor efficacy of the hydrogel formulation is probably due to the protective environment provided by the hydrogel network, which greatly reduced the penetration into the subcutaneous region of proteolytic enzymes that can degrade herceptin.

Figure 15:
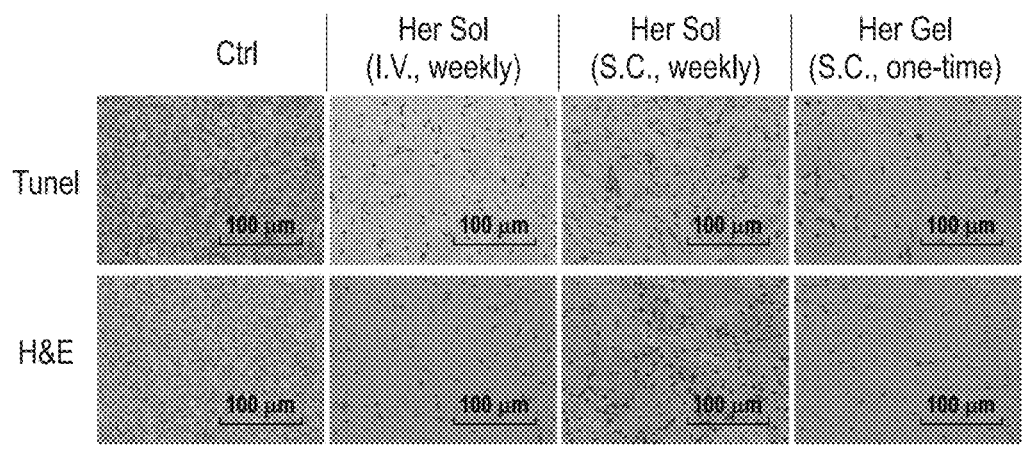
FIG. 15 is a series of photomicrographs showing tumor cells of BT474-tumor bearing mice after TUNEL staining at 28 days following injection of herceptin solution and herceptin loaded hydrogel as described above for FIGS. 14A and 14B. Herceptin solution delivered intravenously is labeled "Her Sol (I.V., weekly"). Herceptin solution delivered subcutaneously is labeled "Her Sol (S.C., weekly"). Herceptin loaded hydrogel (Example 24) delivered subcutaneously is labeled "Her Gel (S.C., one-time"). Herceptin solution injections were performed on a weekly basis while herceptin loaded hydrogel (SC) was injected once on the first day of treatment. The total dosage was 40 mg/kg. The scale bar represents 100 micrometers.

During the early phase of treatment, the anti-tumor efficacy of the subcutaneously injected herceptin-loaded hydrogel Example 24 (4 wt. % VitE1.25-PEG(20k)-VitE1.25 and 1.0 wt. % herceptin) was much more pronounced than the intravenous injected herceptin solution. The hydrogel-treated group had 61% tumor shrinkage (P<0.001) by Day 3, whereas the solution treated group showed reduction in tumor size only after 2 weeks from commencement of treatment. Interestingly, similar to the hydrogel-treated group, the mice injected with herceptin solution (intravenous) showed 32% tumor shrinkage (P=0.001) by the end of the treatment. FIG. 15 is a series of photomicrographs showing tumor cells of BT474-tumor bearing mice after TUNEL staining at 28 days post injection of herceptin in solution (intravenous and subcutaneous) and hydrogel (subcutaneous) formulations. The scale bar represents 100 micrometers. Herceptin solution delivered intravenously is labeled "Her Sol (I.V., weekly"). Herceptin solution delivered subcutaneously is labeled "Her Sol (S.C., weekly"). Herceptin loaded hydrogel (Example 24) delivered subcutaneously is labeled "Her Gel (S.C., one-time"). The weekly administration of herceptin might allow fresh supply of the antibody to enter the circulation, thereby compensating for the loss of bioactivity due to proteolysis and degradation in the body system. Therapeutic efficacy of the one-time injection of herceptin-loaded hydrogel was similar to weekly administration of herceptin in solution (intravenous) as the polymer matrix was able to entrap the antibody and release it in a sustained manner. Apoptosis and significant reduction in the number of cancer cells was observed for both treatment conditions. With regards to clinical relevance, the frequency of injections can be drastically reduced via the use of hydrogel, providing greater convenience in administration over the other formulations.

FIG. 16 is a series of photomicrographs of mice heart, lung, liver and kidney cells after H&E staining at 28 days post injection of herceptin solution formulations (intravenous and subcutaneous) performed on a weekly basis and herceptin loaded hydrogel (subcutaneous) injected once on the first day of treatment. The scale bar represents 100 micrometers. Pathological analysis of normal tissues (heart, lungs, liver and kidneys) resected from the mice revealed no toxicity.

IX. Antimicrobial Properties

Killing Efficiency

Procedure for hydrogels: *E. coli*, *P. aeruginosa*, *S. aureus* and *C. albicans* were obtained from ATCC and reconstituted from its lyophilized form according to the manufacturer's protocol. Bacterial samples were cultured in Tryptic Soy Broth (TSB) solution at 37° C. under constant shaking of 300 rpm. *C. albicans* was culture in yeast medium at room temperature under constant shaking of 70 rpm. Prior to treatment, the bacterial sample was first inoculated and cultured to enter into log growth phase. To prepare the antimicrobial hydrogels, cationic polymer was first dissolved in filtered HPLC water in a bio-hood. The resultant solution was then added to solid triblock copolymer for dissolution and left to stand 4 hours at room temperature for the formation of the hydrogels (Example 28 and Example 29). For instance, cationic polymer VE/BnCl (1:30) or cationic polymer VE/PrBr(1:30) was dissolved by using sterile HPLC grade water to form a polymer solution at various concentrations. This solution was then used to dissolve VitE1.25-PEG(20k)-VitE1.25 to form a 4 wt. % hydrogel containing various concentrations of the cationic polymers.

For antimicrobial treatment, 50 microliter aliquots of the hydrogels incorporated with various amounts of cationic polymers were placed into the wells of a 96-well microplate. The concentration of bacterial solution was adjusted to give an initial optical density (O.D.) reading of approximately 0.07 at 600 nm wavelength on a microplate reader (TECAN, Switzerland), which corresponds to the concentration of McFarland 1 solution ($3 \times 10^8$ CFU/mL) The bacterial solution was then diluted and an equal volume of bacterial suspension ($3 \times 10^5$) was added into each well. The 96-well plate was kept in an incubator at 37° C. under constant shaking of 300 rpm for 18 hours for *E. coli*, *P. aeruginosa*, *S. aureus* and *C. albicans*. After treatment, the samples were taken for a series of tenfold dilution, and plated onto agar plates. The plates were incubated for 24 hours at 37° C. and the number of colony-forming units (CFU) was counted. Bacteria treated in hydrogel without cationic polycarbonates were used as negative control, and each test was carried out in 3 replicates. Minimum bactericidal concentration (MBC) is defined herein as the lowest concentration of the antimicrobial composition that eliminates >99.9% of the microbes.

Procedure for organogels: *E. coli* was obtained from ATCC and reconstituted from its lyophilized form according to the manufacturer's protocol. Bacterial samples were cultured in Tryptic Soy Broth (TSB) solution at 37° C. under constant shaking of 300 rpm. Prior to treatment, the bacterial sample was first inoculated and cultured to enter into log growth phase. For antimicrobial treatment, 20 microliters of the organogels (Example 26 and Example 27) containing 1 wt. % doxycycline was added to sterile vials. The concentration of bacterial solution was adjusted to give an initial optical density (O.D.) reading of approximately 0.07 at 600 nm wavelength on a microplate reader (TECAN, Switzerland), which corresponds to the concentration of McFarland 1 solution ($3 \times 10^8$ CFU/mL) The bacterial solution was then diluted and an equal volume of bacterial suspension ($3 \times 10^5$) was added into each vial and incubated at 37° C. under constant shaking of 300 rpm for 18 hours. After treatment, the samples were taken for a series of tenfold dilution, and plated onto agar plates. The plates were incubated for 24 hours at 37° C. and the number of colony forming units (CFU) was counted. Bacteria treated with KOLLIPHOR RH40 were used as negative control, and each test was carried out in 3 replicates.

Analysis of Drug Interactions

To assess the antimicrobial effects of the drug combinations (e.g., cationic polymer/doxycylcine and/or cationic polymer/fluconazole) the checkerboard and isobologram method of analyzing drug interactions were used. For the checkerboard method, the fractional inhibitory concentration (FBC) was calculated for each component in each combination dose. The types and extent of interaction was determined by calculating the FBC index, which is the ratio of the MBC of a drug in combination and MBC of the drug alone. For two interacting drugs, A and B, the sum of the FBCs indicates the extent of the interaction. Synergy is defined as ΣFIC index <0.5. Indifference was defined as ΣFIC index of >0.5 but <4 and antagonism as a ΣFIC index of >4.0. As for the isobologram method, evaluation of drug interaction is performed at the MBC level. Using graphical analysis, the concentrations required to produce the effect of >99.9% killing efficiency are determined for each component and plotted on the x and y axes of a two-coordinate plot. A line is drawn to connect these two points and this is defined as the line of additivity. Thereafter, treatment is performed with the drugs in combination at varying concentrations. The concentrations of fluconazole and cationic polymer in the combination that provide the same effect are placed in the same plot. Effect of the drug interaction is determined according to the position of the points with respect to the line of additivity. Synergy, additivity, or antagonism is represented when the point is located below, on, or above the line, respectively.

Biofilm Formation and Treatment

*S. aureus* and *E. coli* were grown overnight in tryptic soy broth (TSB) at 37° C. and diluted in TSB to $3 \times 10^6$ and $3 \times 10^8$ CFU/ml before use. *C. albicans* was grown overnight in yeast medium at room temperature and diluted to $3 \times 10^5$ CFU/ml before use. 100 microliters of the diluted cell suspension were then inoculated into each well of 96-well plate and cultured for 7 to 10 days depending on their growth rates. Due to differences in the rate of biofilm formation, *S. aureus* and *C. albicans* were kept shaking at 100 rpm, 37°

C. and 50 rpm, 25° C., respectively. *E. Coli* was incubated at non-shaking conditions at 37° C. The culture medium was changed every day with PBS being added to wash off the planktonic and loosely adhered cells before replacing with fresh medium. Treatment was carried out by first removing the spent medium. The biofilm was washed gently with PBS to remove the planktonic and loosely adhered cells. The biofilm was then incubated with 50 microliters of hydrogel composition for 24 hours.

Biomass Assay

The biomass left after treatment was analyzed using crystal violet (CV) staining assay. The spent medium and hydrogel was gently removed and the biofilm was gently washed with PBS to remove the planktonic cells. Fixation was carried out by adding 100 microliters of methanol to the biofilm and removed after 15 min. Following this, 100 microliters of crystal violet staining (0.1 w/v %) was added to the fixed biofilm and incubated for 10 minutes. Excess crystal violet was washed off thoroughly using HPLC water. The remaining crystal violet bound to the biofilm was extracted using 200 microliters of 33% glacial acetic acid. An aliquot of 150 microliters was then taken from each well and transferred to a fresh 96-well plate. The absorbance was then measured at 570 nm using a microplate reader (Tecan, Switzerland).

XTT Reduction Assay

XTT assay was used for quantifying viable cells in the biofilms after hydrogel treatment by measuring the mitochondrial enzyme activity of the cells. It is based on the reduction of 2,3-bis(2-methoxy-4-nitro-5-sulfophenyl)-5-[(phenylamino)carbonyl]-2H-tetrazolium hydroxide (XTT) in the metabolically active microbial cells to a water soluble formazan. XTT solution (1 mg/mL) and menadione solution (0.4 mM) were individually prepared by dissolution in deionized water. Right before the assay, the two components were mixed together at a volume ratio of XTT:menadione 5:1. During the assay, medium was first removed and biofilm were carefully washed with PBS to remove the planktonic cells. 120 microliters of PBS and 14.4 microliters of the XTT-menadione mixture was then added to each well and incubated for 3 hours. An aliquot of 100 microliters was then taken from each well and transferred to a fresh 96-well plate. The absorbance was then measured at 490 nm using a microplate reader (Tecan, Switzerland).

Field Emission-Scanning Electron Microscopy (FE-SEM)

After treatment, the biofilm was gently washed with PBS and fixed with 4% formaldehyde for 30 minutes. Next, the biofilm was washed with DI water to remove the formaldehyde and a series of ethanol washes (35, 50, 75, 90, 95 and 100%) was carried for dehydration of the samples. After two days of air-drying the samples were mounted on carbon tape and coated with platinum for SEM analysis under a field emission scanning electron microscope (JEOL JSM-7400F, Japan).

Mechanical Properties of Triblock Copolymer/Cationic Polymer Hydrogels

Figure 17A:
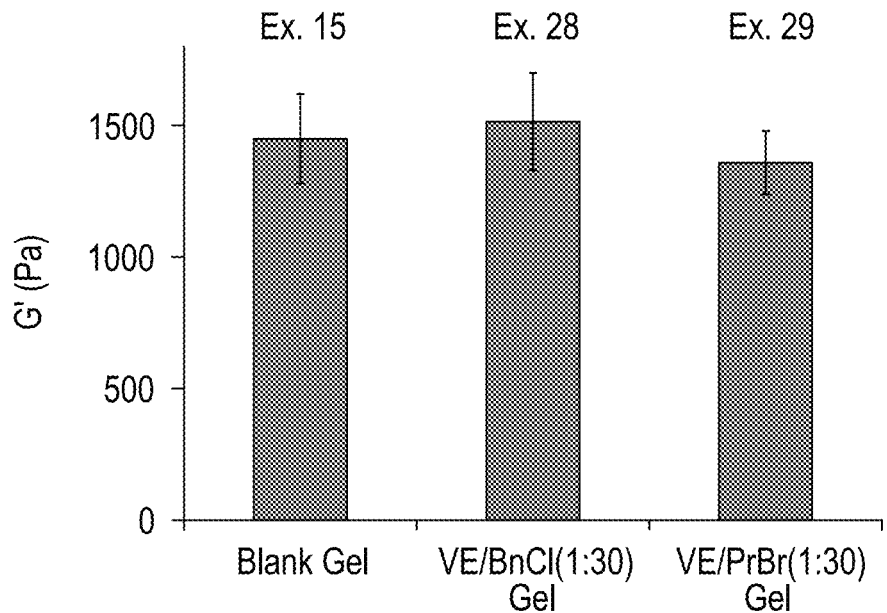
FIG. 17A is a bar graph of G' values of cationic polymer loaded hydrogels Example 28 (containing 4 wt. % VitE1.25-PEG(20k)-VitE1.25 and 0.1 wt. % cationic polymer VE/BnCl (1:30) in HPLC water) and Example 29 (containing 4 wt. % VitE1.25-PEG(20k)-VitE1.25 and 0.1 wt. % cationic polymer VE/PrBr(1:30) in HPLC water). Also shown is blank hydrogel Example 15 (containing 4 wt. % VitE1.25-PEG(20k)-VitE1.25).

The effects of cationic polymers on the mechanical properties of hydrogel matrix were investigated. Cationic polymer (0.1 wt. %; equivalent to 1000 mg/L) was added during the formation of 4 wt. % VitE1.25-PEG(20k)-VitE1.25 hydrogel in HPLC water. FIG. 17A is a bar graph of G' values of cationic polymer loaded hydrogels Example 28 (containing 4 wt. % VitE1.25-PEG(20k)-VitE1.25 and 0.1 wt. % cationic polymer VE/BnCl (1:30) in HPLC water) and Example 29 (containing 4 wt. % VitE1.25-PEG(20k)-VitE1.25 and 0.1 wt. % cationic polymer VE/PrBr(1:30) in HPLC water). Also shown is blank hydrogel Example 15 (containing 4 wt. % VitE1.25-PEG(20k)-VitE1.25). As shown in FIG. 17A, the G' values are in a range of 1400 Pa to 1600 Pa. There is little difference in stiffness between the blank hydrogel and the cationic polymer loaded hydrogels.

Figure 17B:
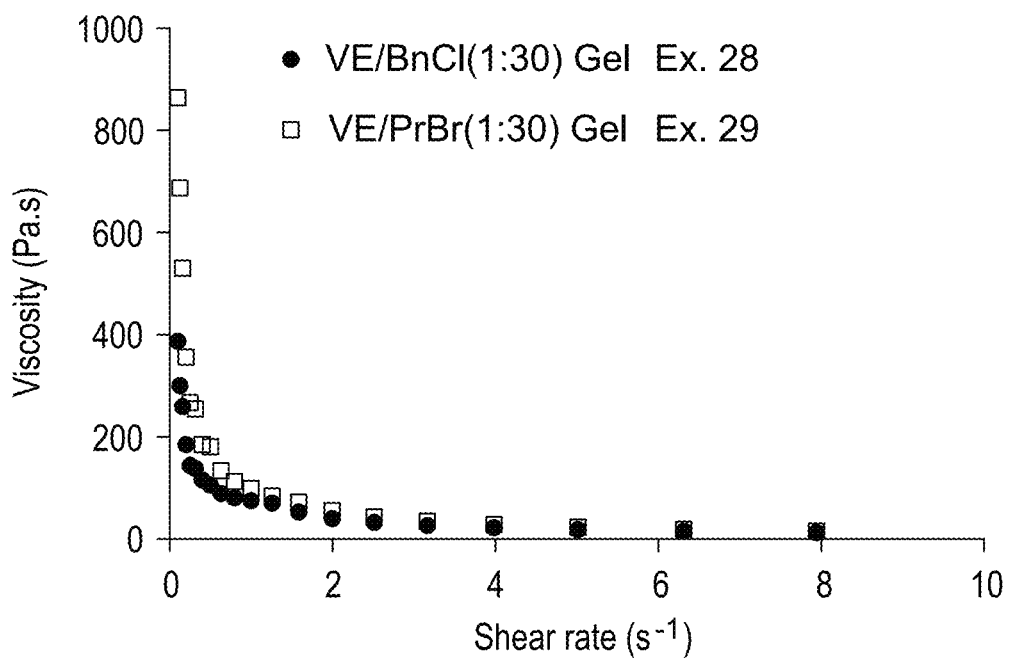
FIG. 17B is a graph of viscosity versus shear rate profile of the cationic loaded hydrogels of FIG. 17A.

FIG. 17B is a graph of viscosity versus shear rate profile of the cationic loaded hydrogels of FIG. 17A. The cationic polymer loaded hydrogels (Example 28 and Example 29) display high viscosity at low shear rates, indicating a firm, well-bodied structure. At the shear rate increases, the viscosity of the gels falls drastically to become a thin liquid. This shear-thinning profile of the hydrogels results from the disruption of physical cross-links between the polymer chains with the application of shear stress. Consequently, this indicates that they can be well-spread over the skin for topical treatment of dermal infection.

Antimicrobial Activity Studies of ABA Triblock/Cationic Polymers Delivered Using Hydrogel Antimicrobial activities of two cationic polymer loaded hydrogels were evaluated against *S. aureus, E. coli* and *C. albicans* as representative models of Gram-positive, Gram-negative bacteria and fungus respectively. These microbes are common pathogens that often manifest on dermal wounds, and can be treated via topical delivery of antibiotics to infected areas.

VE/BnCl (1:30) and VE/PrBr(1:30) were loaded into 4 wt. % VitE1.25-PEG(20k)-VitE1.25 hydrogels (Example 28 and Example 29, respectively). Due to the disparity in antimicrobial efficacies of the two cationic polymers, different concentration ranges were used for the preparation of the hydrogels. The hydrogels were challenged with an inoculum of $3\times10^5$ CFU/ml and proliferation capacity of the survived cells was then assessed 24 hours later via the spread plate technique. This method of examining the antimicrobial activity is akin to measuring the minimum inhibitory concentration (MIC) of the cationic polymers in solution.

Figure 18A:
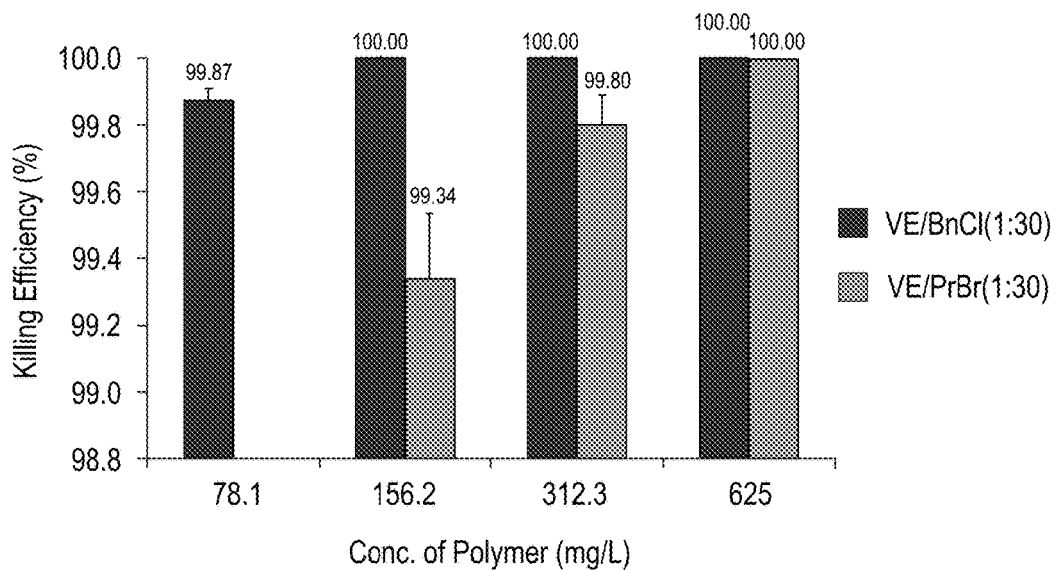
FIG. 18A to 18C are bar graphs showing the killing efficiency against *Staphylococcus aureus* (*S. aureus*), *Escherichia coli* (*E. coli*), and *Candida albicans* (*C. albicans*), respectively, of cationic polymer loaded hydrogels containing 4 wt. % VitE1.25-PEG(20k)-VitE1.25 and various concentrations of VE/BnCl (1:30) or VE/PrBr(1:30). The concentration of polymer on the horizontal axis refers to cationic polymer.
Figure 18B:
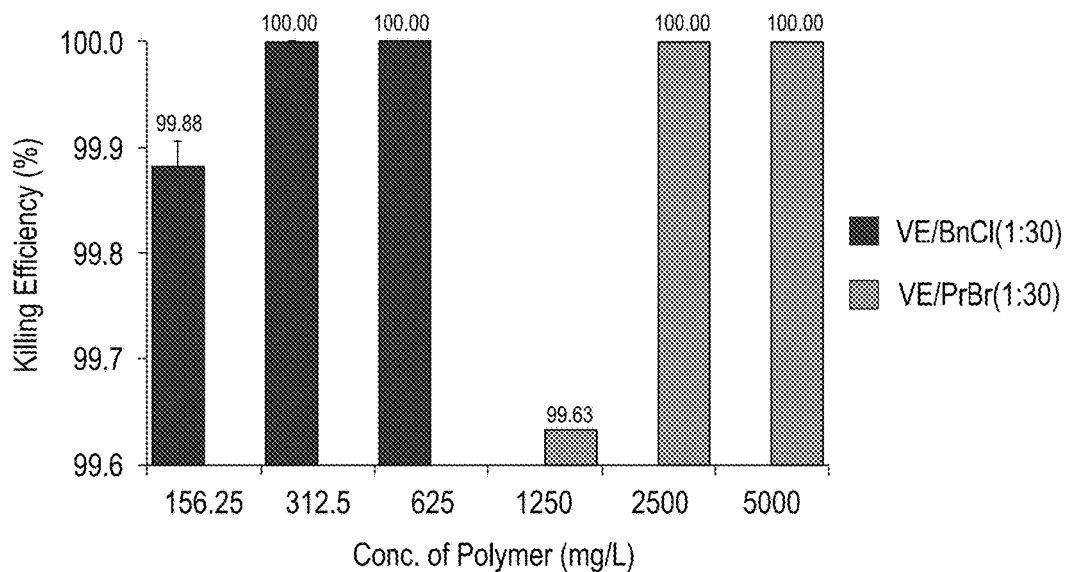
Figure 18C:
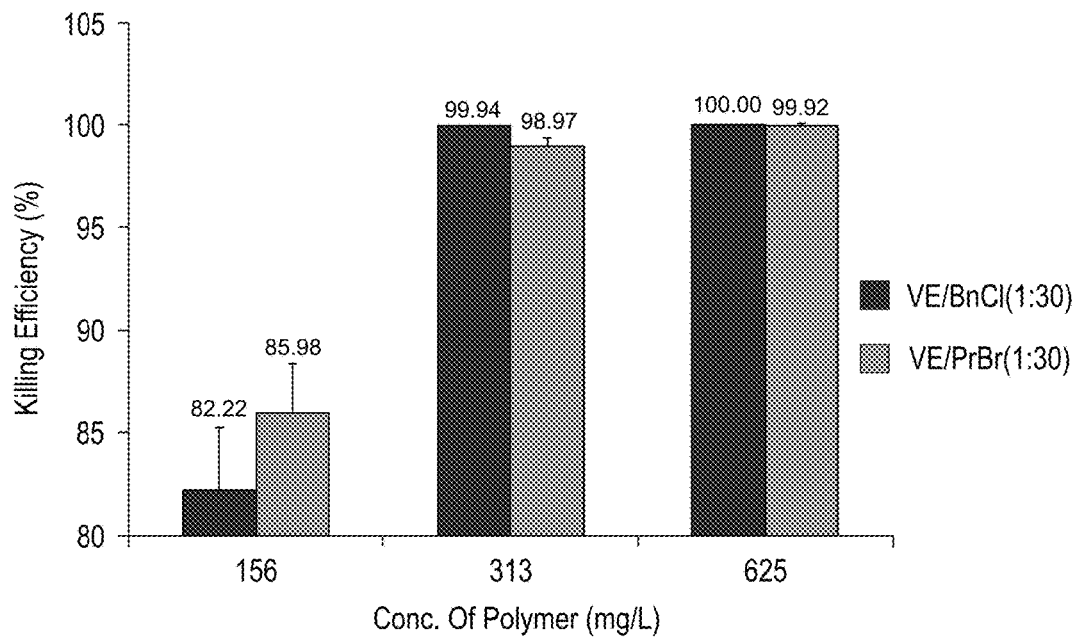

FIGS. 18A to 18C are bar graphs showing the killing efficiency against *Staphylococcus aureus* (*S. aureus*), *Escherichia coli* (*E. coli*), and *Candida albicans* (*C. albicans*), respectively, of cationic polymer loaded hydrogels containing 4 wt. % VitE1.25-PEG(20k)-VitE1.25 and various concentrations of cationic polymers VE/BnCl (1:30) or VE/PrBr(1:30). The concentration indicated on the horizontal axis refers to cationic polymer. The results show that the cationic polymers delivered by hydrogel are broadly antimicrobial against bacteria and fungi.

Table 12 lists the minimum bactericidal concentrations (MBC) of the cationic polymer with and without triblock copolymer against *S. aureus, E. coli*, and *C. albicans*. The MBC value refers to the amount of cationic polymer in mg/L. For the cationic polymer alone (Examples 2 and 8), the solution MBC value is equal to the solution minimum inhibitory concentration (MIC) against each microbe.

TABLE 12

| Example | Triblock Copolymer | Cationic Polymer | Wt. % Triblock copolymer | Wt. % Cationic Polymer | MBC[a] (mg/L) S. aureus | E. coli | C. albicans |
|---|---|---|---|---|---|---|---|
| 2 |  | VE/PrBr(1:30) |  |  | 63[b] | 250[b] | 250[b] |
| 8 |  | VE/BnCl(1:30) |  |  | 31[b] | 31[b] | 250[b] |
| 28 | VitE1.25-PEG(20k)-VitE1.25 | VE/BnCl(1:30) | 4 | 0.1 | 156.2 | 312.5 | 312.5 |
| 29 | VitE1.25-PEG(20k)-VitE1.25 | VE/PrBr(1:30) | 4 | 0.1 | 312.5 | 2500.0 | 625.0 |

[a]MBC values refer to the amount of cationic polymer in mg/L
[b]MBC = MIC

Table 12 shows the presence of the triblock copolymer lowers the antimicrobial efficacy of the cationic polymer (i.e., increases the MBC relative to the cationic polymer alone). The loaded hydrogels are most effective in inhibiting Gram-positive *S. aureus* proliferation. *S. aureus* requires the lowest amount of each cationic polymer (MBC=156.2 mg/L for VE/BnCl (1:30) and 312.5 mg/L for VE/PrBr(1:30)). The cationic polymer loaded hydrogels were less able to inhibit the proliferation of Gram-negative *E. coli* (MBC=312.5 mg/L for VE/BnCl (1:30) and 2500 mg/L and VE/PrBr (1:30)). The antimicrobial effect on *C. albicans* (fungus) was intermediate to that of the two bacteria species (MBC=312.5 mg/L for VE-BnCl (1:30) and 625 mg/L for VE/PrBr(1:30)). The MBC value of the cationic polymer (Table 12) is lower than the concentrations at which the cationic polymers become hemolytic towards mammalian cells.

The loaded hydrogels are consistent with the solution properties of the cationic polymers alone. That is, the cationic polymer VE/BnCl (1:30) exhibits greater antimicrobial/antifungal properties compared to VE/PrBr(1:30) whether delivered in solution or as a hydrogel complex.

Antimicrobial Activity of Doxycycline-Loaded Organogels

Figure 19:
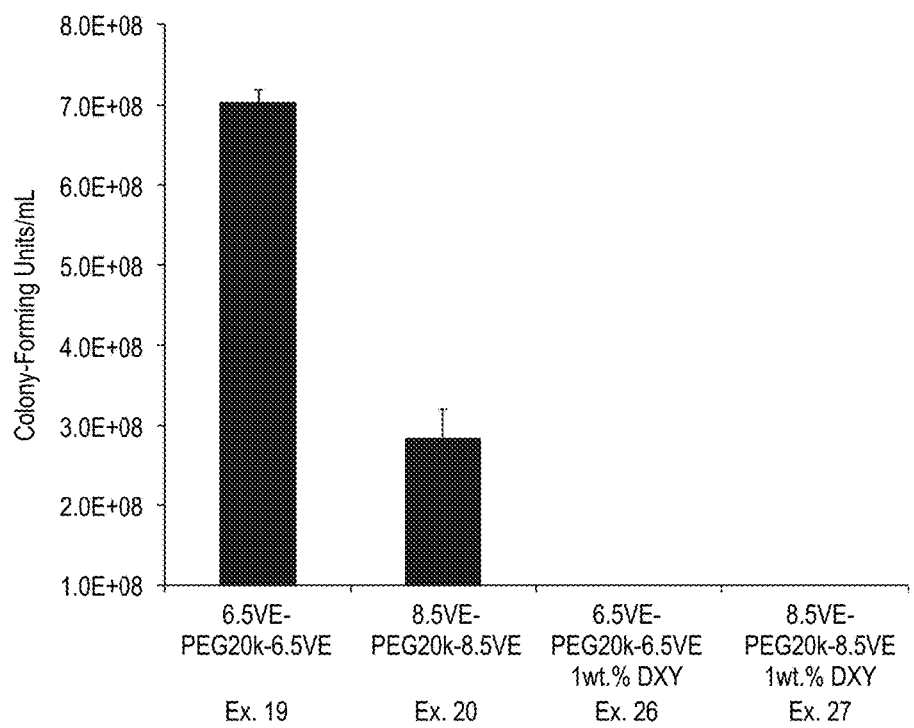
FIG. 19 is a bar graph showing the number of viable bacterial colony-forming units (CFU) after 18 hour treatment of *E. coli*, with:
a) blank organogel Examples 19 ("6.5VE-PEG20k-6.5VE"),
b) blank organogel Example 20 ("8.5VE-PEG20k-8.5VE")
c) doxycycline loaded organogel Example 26 ("6.5VE-PEG20k-6.5VE 1 wt. % DXY"), and
d) doxycycline loaded organogel Example 27 "8.5VE-PEG20k-8.5VE 1 wt. % DXY").

The antimicrobial effectiveness of drug-loaded organogels (Examples 26 and 27) was tested on *E. coli*. *E. coli* strains from skin and soft tissue infections can exhibit strong virulence potential. FIG. 19 is a bar graph showing the number of viable bacterial colony-forming units (CFU) after 18 hour treatment of *E. coli*, with blank organogels (Examples 19 and 20, labeled "6.5VE-PEG20k-6.5VE" and "8.5VE-PEG20k-8.5VE", respectively) and doxycycline loaded organogels (Examples 26 and 27, labeled "6.5VE-PEG20k-6.5VE 1 wt. % DXY" and "8.5VE-PEG20k-8.5VE 1 wt. % DXY", respectively). The doxycycline loaded organogels demonstrated 100% bactericidal activity (0 CFU). Although the doxycycline concentration used is higher than the reported minimum bactericidal concentration (MBC) range in several *E. coli* strains, 1 wt. % was selected because this is a typical loading content in clinically-approved doxycycline formulations such as NanoDOX® and ATRIDOX®.

Synergism of Fluconazole and Cationic Polymer VE/PrBr (1:15) Delivered by Solution The following demonstrate synergistic enhancement of antimicrobial activity using cationic polymer VE/PrBr(1:15) in combination with fluconazole delivered via solution. Fluconazole (Flue) is a member of the azole family of antifungal agents that possess good activity against *C. albicans* and exhibits low toxicity. While being considerably safe for clinical applications, the downside of using azoles is that they are only fungistatic, not fungicidal.

A stock solution of cationic polymer VE/PrBr(1:15) (5 mg) in sterile HPLC grade water (10 ml) was prepared having a final concentration of 500 mg/L (500 ppm). A second stock solution of fluconazole (1 mg) in sterile HPLC grade water (100 ml) was prepared having a final concentration of 10 mg/L (10 ppm). Three solutions were prepared: (1) cationic polymer alone at 1.0MIC=250 mg/L (250 ppm) against *C. albicans*, (2) A cationic polymer/fluconazole solution containing VE/PrBr(1:15) at 0.5MIC=125 mg/L (125 ppm) against *C. albicans* and fluconazole at 2.5 mg/L (2.5 ppm), and (3) fluconazole alone at 5.0 mg/L (5 ppm). Formulation (2) was obtained by combining 125 microliters each of the stock solutions of cationic polymer and fluconazole and diluting the resulting solution with 750 microliters of sterile HPLC grade water.

Figure 20:
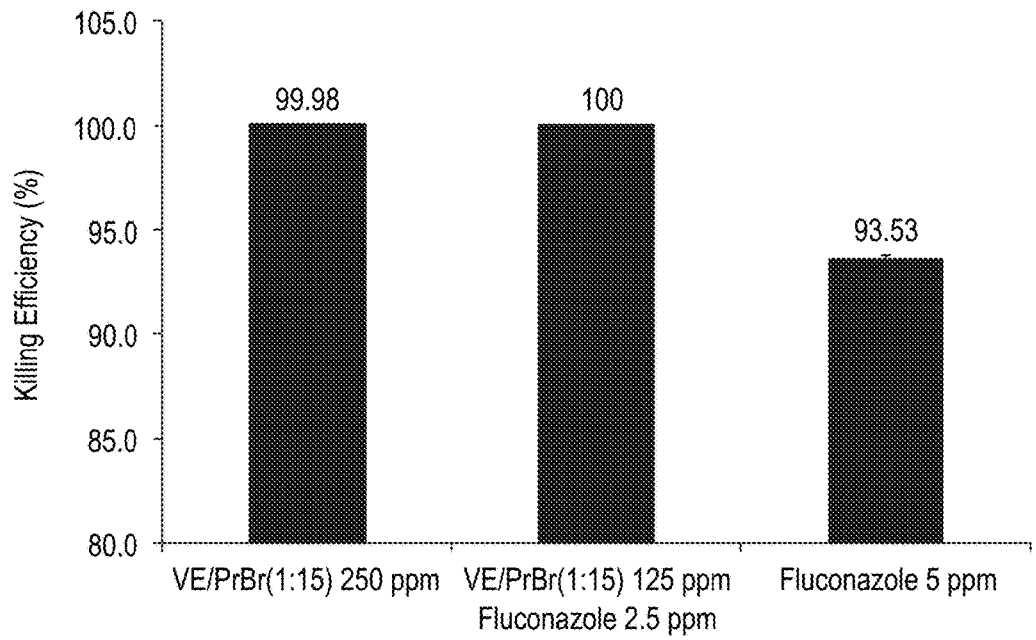
FIG. 20 is a bar graph showing the killing efficiencies of three solutions against *C. albicans*:
a) VE/PrBr(1:15) alone at 1.0MIC (250 ppm) against *C. Albicans*,
b) VE/PrBr(1:15)/fluconazole solution prepared with VE/PrBr(1:15) at 0.5MIC (125 ppm) and fluconazole (2.5 ppm), and
c) fluconazole alone (5.0 ppm). MIC refers to minimum inhibitory concentration of the cationic polymer.

FIG. 20 is a bar graph showing the killing efficiencies of the three solutions against *C. albicans*. The cationic polymer solution (1) achieved 99.98% killing efficiency at 1.0MIC=250 mg/L (250 ppm). The fluconazole solution (3) achieved 93.53% killing efficiency at 5.0 mg/L (5 ppm). However, solution (2) containing VE/PrBr(1:15) and fluconazole achieved 100% killing efficiency using VE/PrBr (1:15) at 0.5MIC=125 mg/L (125 ppm) and fluconazole at 2.5 mg/L (2.5 ppm).

Figure 21:
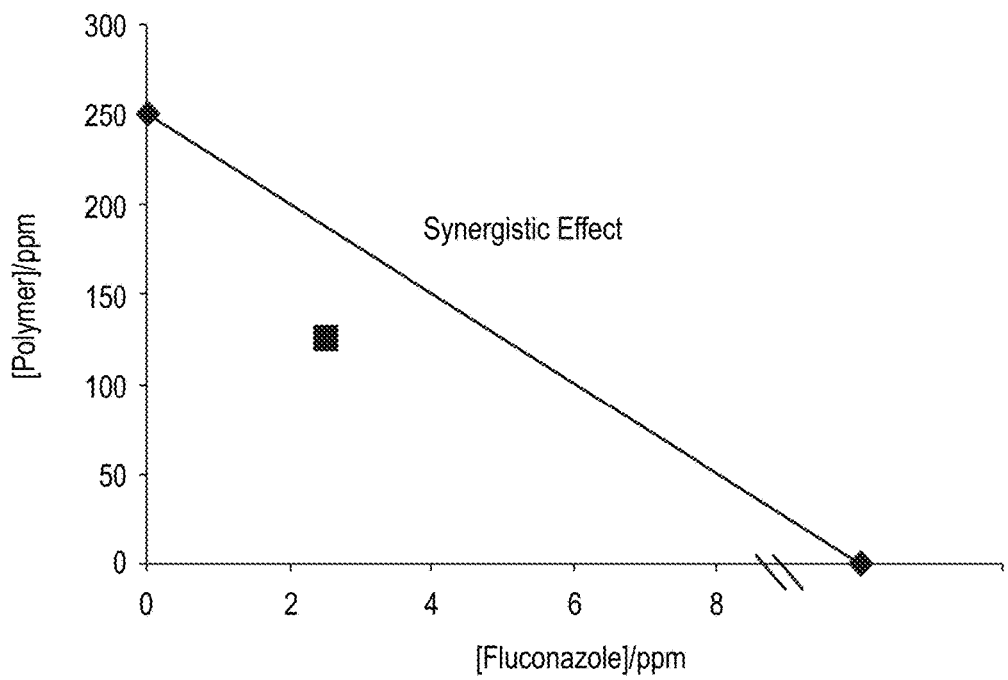
FIG. 21 is an isobologram demonstrating the synergy of the VE/PrBr(1:15)/fluconazole combination compared to VE/PrBr(1:15) alone and fluconazole alone delivered by solution against *C. albicans*. The synergy is indicated by the drug combination dose that lies to the left of the line of additivity, shown as a square inside the triangle.

FIG. 21 is a graph (isobologram) demonstrating the synergy of the VE/PrBr(1:15)/fluconazole combination compared to VE/PrBr(1:15) alone and fluconazole alone delivered by solution against *C. albicans*. The synergy is indicated by the drug combination dose that lies to the left of the line of additivity, shown as a square inside the triangle.

Figure 22:
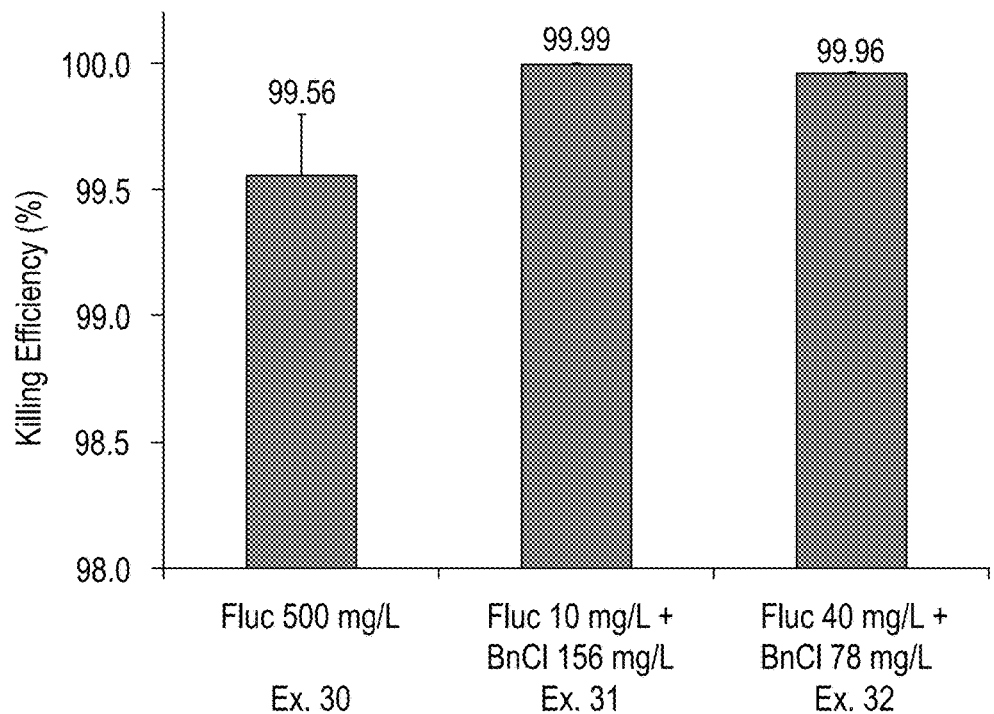
FIG. 22 is a bar graph comparing the killing efficiency against *C. albicans* of
(a) fluconazole loaded hydrogel Example 30 (containing 4 wt. % VitE1.25-PEG(20k)-VitE1.25 and 0.05 wt. % fluconazole) used at a loaded hydrogel concentration of 500 mg/L,
(b) cationic polymer/fluconazole loaded hydrogel Example 31 (containing 4 wt. % VitE1.25-PEG(20k)-VitE1.25), 0.0156 wt. % cationic polymer VE/BnCl (1:30), and 0.001 wt. % fluconazole) used at a concentration of fluconazole=10 mg/L and VE/BnCl (1:30)=156 mg/L (0.5MBC), and
(c) cationic polymer/fluconazole loaded hydrogel Example 32 (containing 4 wt. % VitE1.25-PEG(20k)-VitE1.25), 0.0078 wt. % cationic polymer VE/BnCl (1:30), and 0.004 wt. % fluconazole) used at a concentration of fluconazole=40 mg/L and VE/BnCl (1:30)=78 mg/L (0.25MBC). MBC refers to the minimum bactericidal concentration.

Synergism of Fluconazole and Cationic Polymer VE/BnCl (1:30) Delivered by a Hydrogel The following results demonstrate synergistic enhancement of antimicrobial activity against *C. albicans* using three component hydrogel containing VitE1.25-PEG(20k)-VitE1.25, cationic polymer VE/BnCl (1:30) and fluconazole. Three hydrogels were compared: (1) fluconazole loaded hydrogel Example 30 (containing 4 wt. % VitE1.25-PEG (20k)-VitE1.25 and 0.05 wt. % fluconazole) used at a loaded hydrogel concentration of 500 mg/L, (2) cationic polymer/fluconazole loaded hydrogel Example 31 (containing 4 wt. % VitE1.25-PEG(20k)-VitE1.25, 0.0156 wt. % cationic polymer VE/BnCl (1:30), and 0.001 wt. % fluconazole) used at a concentration of fluconazole=10 mg/L and VE/BnCl (1:30)=156 mg/L (0.5MBC), and (3) cationic polymer/fluconazole loaded hydrogel Example 32 (containing 4 wt. % VitE1.25-PEG(20k)-VitE1.25, 0.0078 wt. % cationic polymer VE/BnCl (1:30), and 0.004 wt. % fluconazole) used at a concentration of fluconazole=40 mg/L and VE/BnCl (1:30)=78 mg/L (0.25MBC). FIG. 22 is a bar graph comparing the killing efficiency against C. albicans of the three hydrogels. Even at a high concentration of 500 mg/L, fluconazole alone was able to kill only 99.56% of C. albicans, whereas the drug combination of Example 31 used at a concentration of fluconazole=10 mg/L and VE/BnCl (1:30)=156 mg/L (0.5MBC) killed 99.99% of C. albicans (FIG. 22, middle bar).

Figure 23:
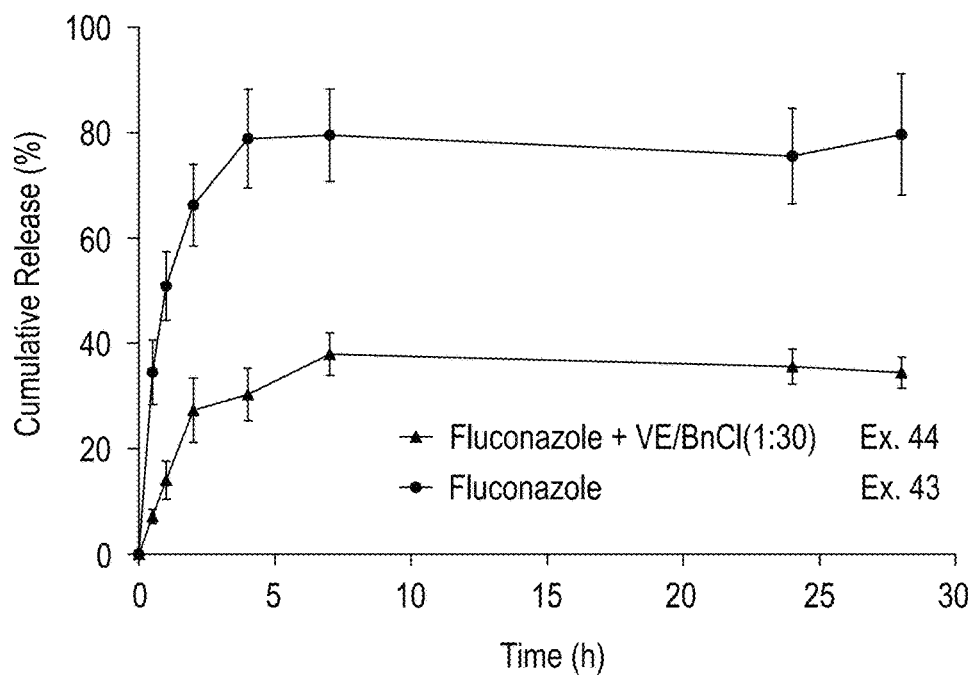
FIG. 23 is a graph showing the release rate of fluconazole from fluconazole loaded hydrogel Example 43 containing 4 wt. % VitE1.25-PEG(20k)-VitE1.25 and 0.05 wt. % fluconazole (upper curve), and cationic polymer/fluconazole loaded hydrogel Example 44 containing 4 wt. % VitE1.25-PEG(20k)-VitE1.25), 0.3 wt. % cationic polymer VE/BnCl (1:30), and 0.3 wt. % fluconazole (lower curve).

FIG. 23 is a graph showing the release rate of fluconazole from fluconazole loaded hydrogel Example 43 (containing 4 wt. % VitE1.25-PEG(20k)-VitE1.25 and 0.3 wt. % fluconazole, upper curve), and cationic polymer/fluconazole loaded hydrogel Example 44 (containing 4 wt. % VitE1.25-PEG(20k)-VitE1.25), 0.3 wt. % cationic polymer VE/BnCl (1:30), and 0.3 wt. % fluconazole, lower curve). The results show that about 80% of the fluconazole was released within 4 hours from the two component hydrogel Example 43 (FIG. 23, upper curve), and about 40% of the fluconazole was released within about 7 hours from the three component hydrogel Example 44 (FIG. 23, upper curve).

Figure 24:
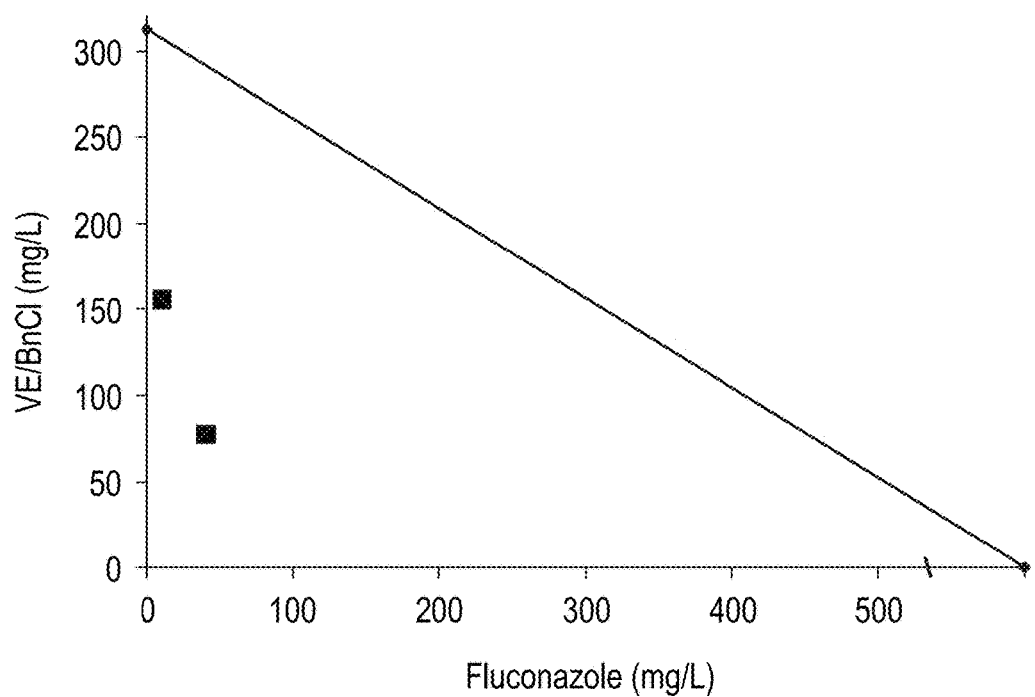
FIG. 24 is an isobologram demonstrating the synergy of the combination of VE/BnCl (1:30) and fluconazole for minimum bactericidal activity when delivered by hydrogel. Synergy between the cationic polymer and fluconazole is shown by the drug combination dosage lying to the left of the line of additivity for each loaded hydrogel, represented by a square inside the triangle. The upper square corresponds to Example 31 containing 4 wt. % VitE1.25-PEG (20k)-VitE1.25), 0.0156 wt. % cationic polymer VE/BnCl (1:30), and 0.001 wt. % fluconazole. The bottom square corresponds to Example 32 containing 4 wt. % VitE1.25-PEG(20k)-VitE1.25), 0.0078 wt. % cationic polymer VE/BnCl (1:30), and 0.004 wt. % fluconazole.

By combining this fungistatic drug and cationic polymer in a hydrogel matrix, significant improvement in the therapeutic efficacy at two combination doses was observed. The FBC index of the combination doses was ~0.5 and ~0.25 respectively, indicating synergistic interaction from the codelivery of the two compounds. Furthermore, the isobologram method of analyzing drug interactions further illustrates the strong synergism between fluconazole and VE/BnCl (1:30) when delivered by the hydrogel. FIG. 24 is an isobologram demonstrating the synergy of the combination dosages (VE/BnCl (1:30)/fluconazole) for minimum bactericidal activity when delivered by loaded hydrogel Example 31 (4 wt. % VitE1.25-PEG(20k)-VitE1.25), 0.0156 wt. % cationic polymer VE/BnCl (1:30), and 0.001 wt. % fluconazole) and loaded hydrogel Example 32 (4 wt. % VitE1.25-PEG(20k)-VitE1.25), 0.0078 wt. % cationic polymer VE/BnCl (1:30), and 0.004 wt. % fluconazole). Synergy between the cationic polymer and fluconazole is shown by the drug combination dosage lying to the left of the line of additivity for each loaded hydrogel, shown as a square inside the triangle. The upper square corresponds to Example 31, the bottom square corresponds to Example 32.

Synergism of Doxycycline (DXY)/Cationic Polymer Delivered by a Hydrogel

Figure 25:
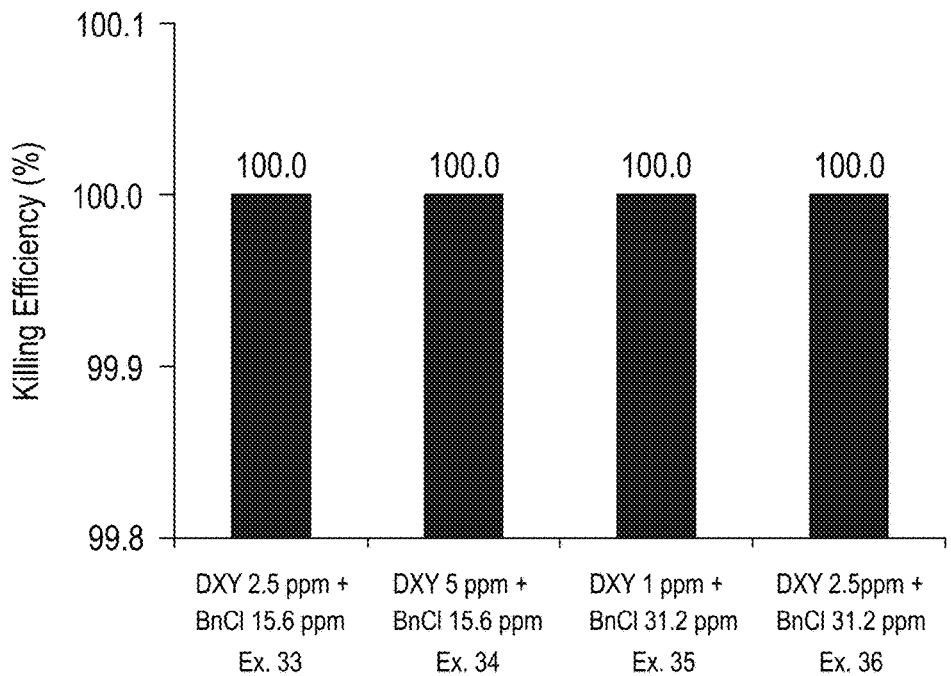
FIG. 25 is a bar graph show the killing efficiency of a cationic polymer/doxycycline (DXY) loaded hydrogel against *Pseudomonas aeruginosa* (*P. aeruginosa*). Four loaded hydrogels were prepared with VitE1.25-PEG(20k)-VitE1.25, DXY, and cationic polymer VE/BnCl (1:30) having DXY/VE/BnCl (1:30) ratios of 2.5 ppm/15.6 ppm (Example 33), 5 ppm/15.6 ppm (Example 34), 1 ppm/31.2 ppm (Example 35), and 2.5 ppm/31.2 ppm (Example 36), respectively. The killing efficiency was 100% at using DXY loadings of 1 ppm to 5 ppm DXY and VE/BnCl (1:30) loadings of 15 ppm to 31 ppm.
Figure 26:
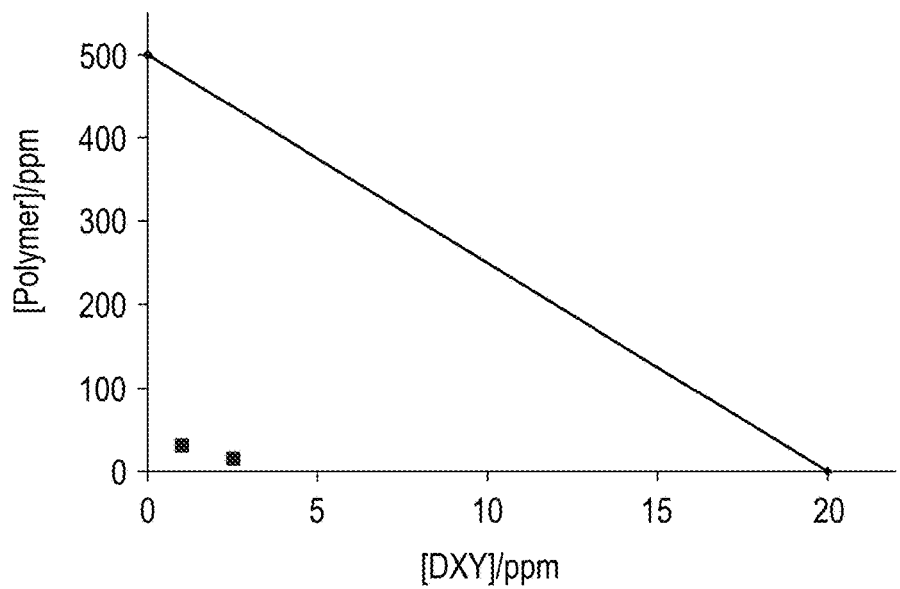
FIG. 26 is an isobologram demonstrating the synergy of cationic polymer VE/BnCl (1:30) and doxycycline (DXY) against *P. aeruginosa* when delivered by loaded hydrogels Example 33 and Example 35, indicated by a combination dosage to the left of the line of additivity, represented by a square inside the triangle. The left square corresponds to Example 35, the right square to Example 33.

DXY is a tetracycline antibiotic. Loaded hydrogels were prepared with VitE1.25-PEG(20k)-VitE1.25, DXY, and cationic polymer VE/BnCl (1:30). The hydrogels were tested against Pseudomonas aeruginosa (P. aeruginosa), a common pathogen in hospital patients with greater than 1 week stays. The MBC of DXY against P. aeruginosa is about 20-30 mg/L (30 ppm). The MBC of VE/BnCl (1:30) against P. aeruginosa is about 500 mg/L (500 ppm). Four hydrogels were prepared having DXY/VE/BnCl (1:30) ratios of 2.5 ppm/15.6 ppm (Example 33), 5 ppm/15.6 ppm (Example 34), 1 ppm/31.2 ppm (Example 35), and 2.5 ppm/31.2 ppm (Example 36), respectively. FIG. 25 is a bar graph showing that each hydrogel achieved 100% killing efficiency. FIG. 26 is an isobologram demonstrating the synergy of a doxycycline/cationic polymer against P. aeruginosa when delivered by loaded hydrogels Example 33 and Example 35, indicated by a drug combination dose to the left of the line of additivity, represented by a square inside the triangle. The left square corresponds to Example 35, the right square to Example 33. The drug combination is effective at extremely low doxycycline concentration (about 1 ppm, or 1 mg/L).

Biofilm Eradication by ABA Triblock/Cationic Polymer Hydrogels

The cationic polymer loaded hydrogels were investigated for their ability to eradicate biofilms. The formation of biofilms occurs as microbes adheres to a surface (inanimate material or tissue) and as they proliferate, they can secrete insoluble gelatinous exopolymers that results in a three-dimensional cell:polymer matrix known as a biofilm. Manifestation of medical biofilm can be extremely challenging as microbes growing in biofilms are recalcitrant and drastically less responsive to antimicrobial agents and host defense systems compared to the planktonic cells. Biofilm persistence can led to clinical conditions such as impaired wound healing, chronic inflammation and the spread of infectious emboli.

To establish relevance to antimicrobial agents used in biofilm elimination, various microbes (S. aureus, E. coli and C. albicans) were cultured for several days for the development of biofilm prior to the treatment. Cationic polymer VE/BnCl (1:30) or cationic polymer VE/PrBr(1:30) was loaded at MBC concentration for S. aureus, E. coli or C. albicans into VitE1.25-PEG(20k)-VitE1.25 (4 wt. %) hydrogels and placed onto the biofilm. Cationic polymer loaded hydrogels Example 37 and Example 38 were prepared for S. aureus, cationic polymer loaded hydrogels Example 39 and Example 40 were prepared for E. coli, and cationic polymer loaded hydrogels Example 41 and Example 42 were prepared for C. albicans. The corresponding blank hydrogel Example 15 was used as a control. The culture was then incubated with the hydrogels for 24 hours for antimicrobial actions to occur. XTT assay was then performed to evaluate the viability of the remaining microbe. In this assay, a lower optical density (O.D.) reading corresponds to lower cell viability and better biofilm elimination capacities of the hydrogels.

Figure 27A:
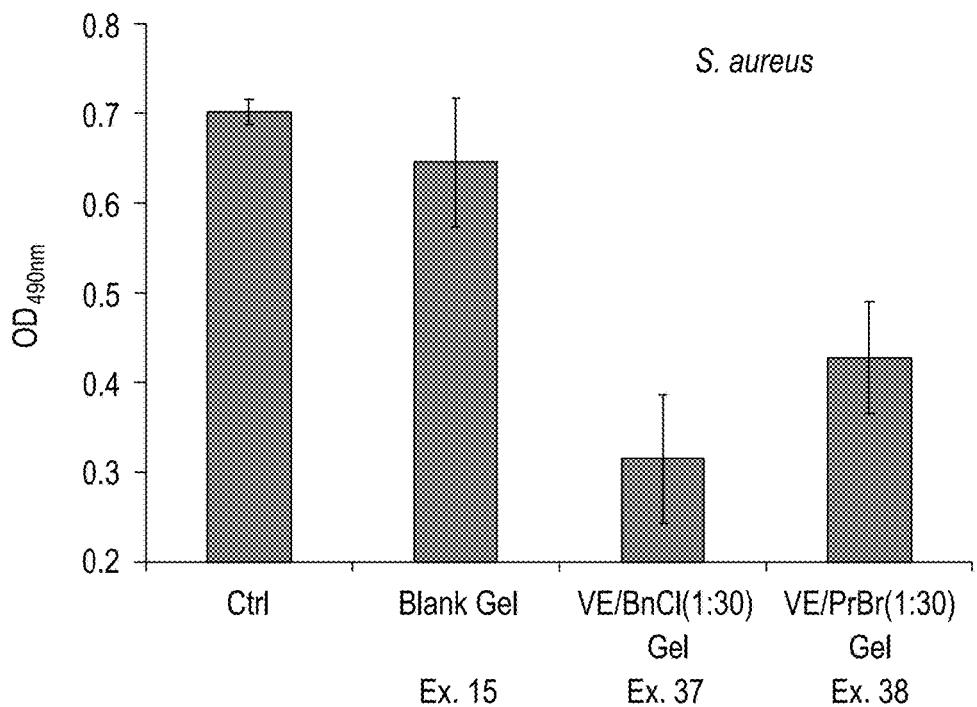
FIGS. 27A and 27B are bar graphs showing the reduction in metabolic activity and biomass, respectively, of *S. aureus* biofilms by:
  a) blank hydrogel Example 15 containing 4 wt. % VitE1.25-PEG(20k)-VitE1.25,
  b) cationic polymer loaded hydrogel Example 37 containing 4 wt. % VitE1.25-PEG(20k)-VitE1.25 and 0.0156 wt. % VE/BnCl (1:30), and
  c) cationic polymer loaded hydrogel Example 38 containing 4 wt. % VitE1.25-PEG(20k)-VitE1.25 and 0.0625 wt. % VE/PrBr(1:30). Cationic polymer VE/BnCl (1:30) and cationic polymer VE/PrBr(1:30) were loaded at minimum bactericidal concentrations (MBC) against *S. aureus* into VitE1.25-PEG(20k)-VitE1.25 (4 wt. %) hydrogels.
Figure 27B:
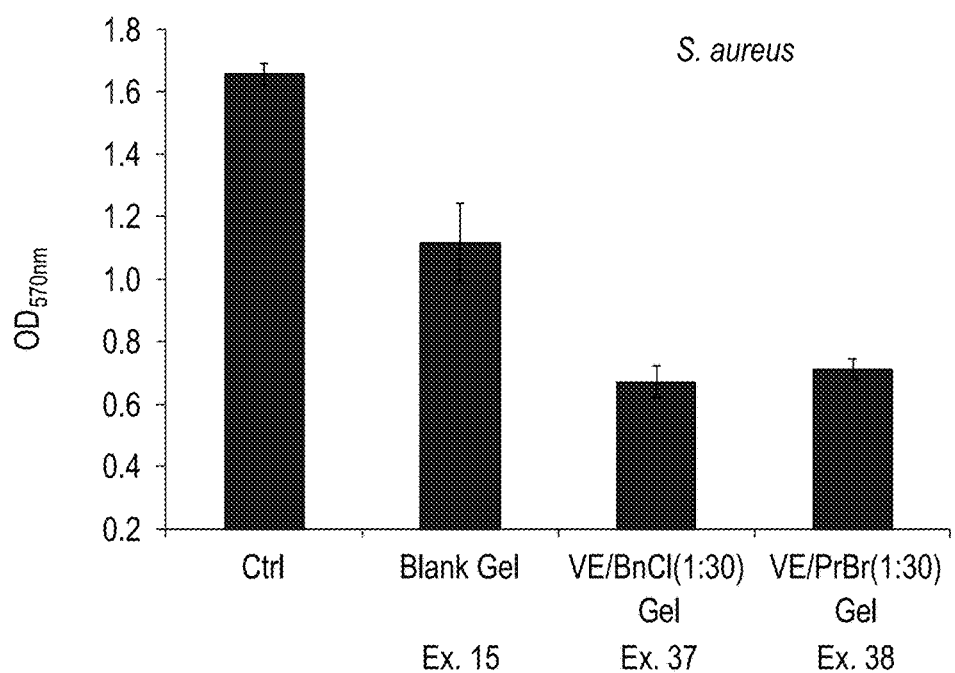

FIGS. 27A and 27B are bar graphs showing the reduction in metabolic activity and biomass, respectively, of S. aureus biofilms by blank hydrogel Example 15 (containing 4 wt. % VitE1.25-PEG(20k)-VitE1.25), cationic polymer loaded hydrogel Example 37 (containing 4 wt. % VitE1.25-PEG (20k)-VitE1.25 and 0.0156 wt. % VE/BnCl (1:30)), and cationic polymer loaded hydrogel Example 38 (containing 4 wt. % VitE1.25-PEG(20k)-VitE1.25 and 0.0625 wt. % VE/PrBr(1:30)). A reduction in metabolic activity (FIG. 27A) and biomass (FIG. 27B) was obtained with the cationic polymer loaded hydrogels against S. aureus.

Figure 28A:
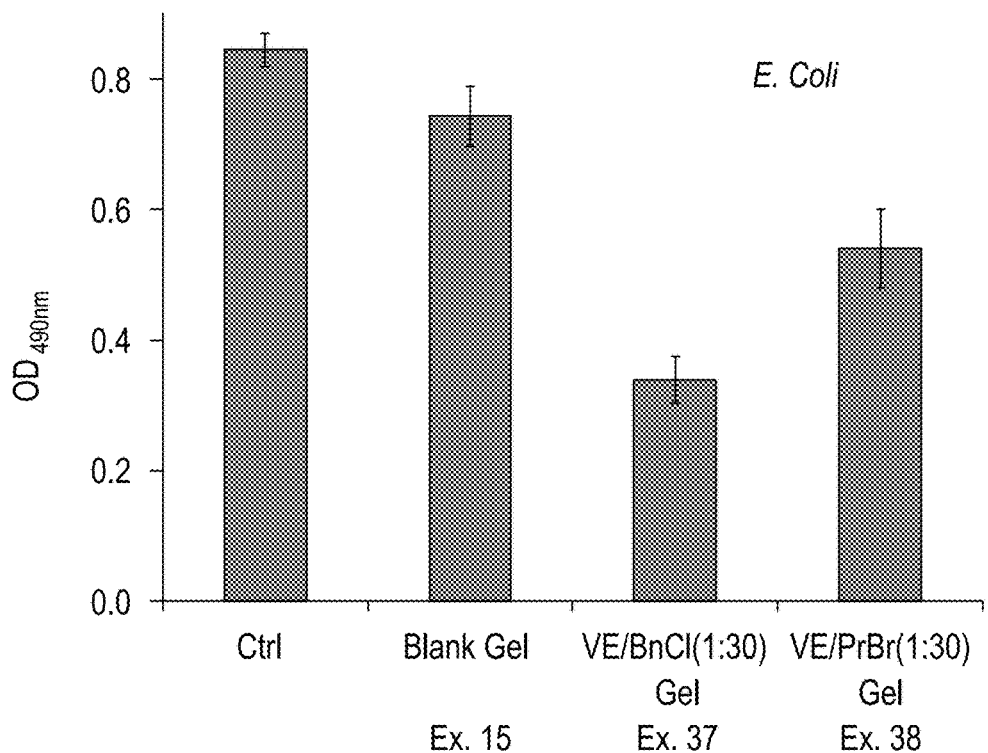
FIGS. 28A and 28B are bar graphs showing the reduction in metabolic activity and biomass, respectively, of *E. coli* biofilms by:
  a) blank hydrogel Example 15 containing 4 wt. % VitE1.25-PEG(20k)-VitE1.25,
  b) cationic polymer loaded hydrogel Example 37 containing 4 wt. % VitE1.25-PEG(20k)-VitE1.25 and 0.0156 wt. % VE/BnCl (1:30), and
    c) cationic polymer loaded hydrogel Example 38 containing 4 wt. % VitE1.25-PEG(20k)-VitE1.25 and 0.0625 wt. % VE/PrBr(1:30). Cationic polymer VE/BnCl (1:30) and cationic polymer VE/PrBr(1:30) were loaded at minimum bactericidal concentrations (MBC) against *E. coli* into VitE1.25-PEG(20k)-VitE1.25 (4 wt. %) hydrogels.
Figure 28B:
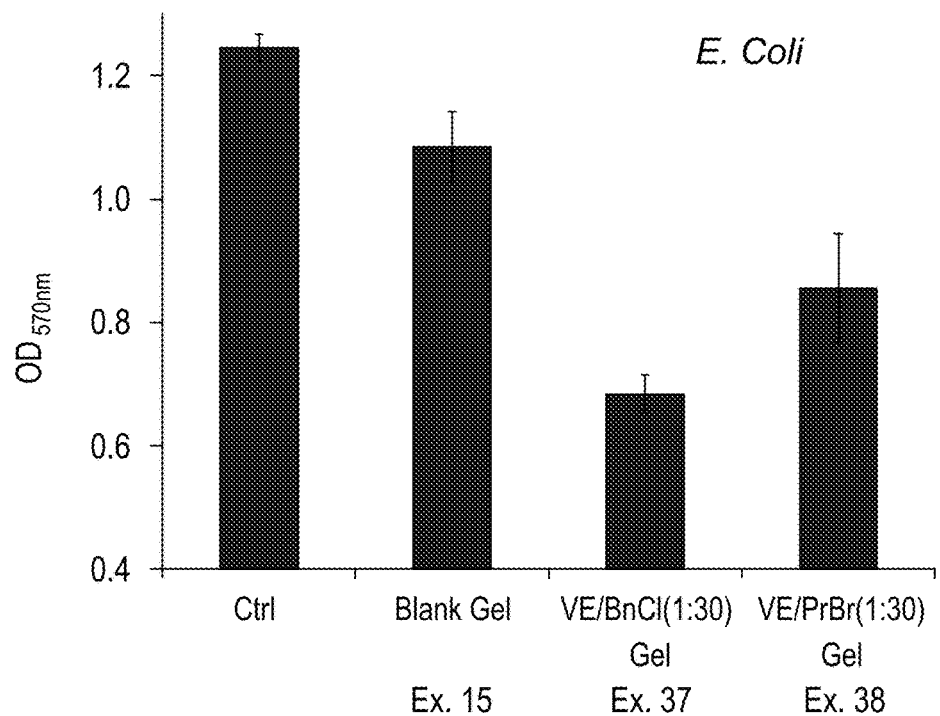

FIGS. 28A and 28B are bar graphs showing the reduction in metabolic activity and biomass, respectively, of E. coli biofilms by blank hydrogel Example 15 (containing 4 wt. % VitE1.25-PEG(20k)-VitE1.25), cationic polymer loaded hydrogel Example 37 (containing 4 wt. % VitE1.25-PEG (20k)-VitE1.25 and 0.0156 wt. % VE/BnCl (1:30)), and cationic polymer loaded hydrogel Example 38 (containing 4 wt. % VitE1.25-PEG(20k)-VitE1.25 and 0.0625 wt. % VE/PrBr(1:30)). A reduction in metabolic activity (FIG. 28A) and biomass (FIG. 28B) was obtained with the cationic polymer loaded hydrogels against E. coli.

Figure 29A:
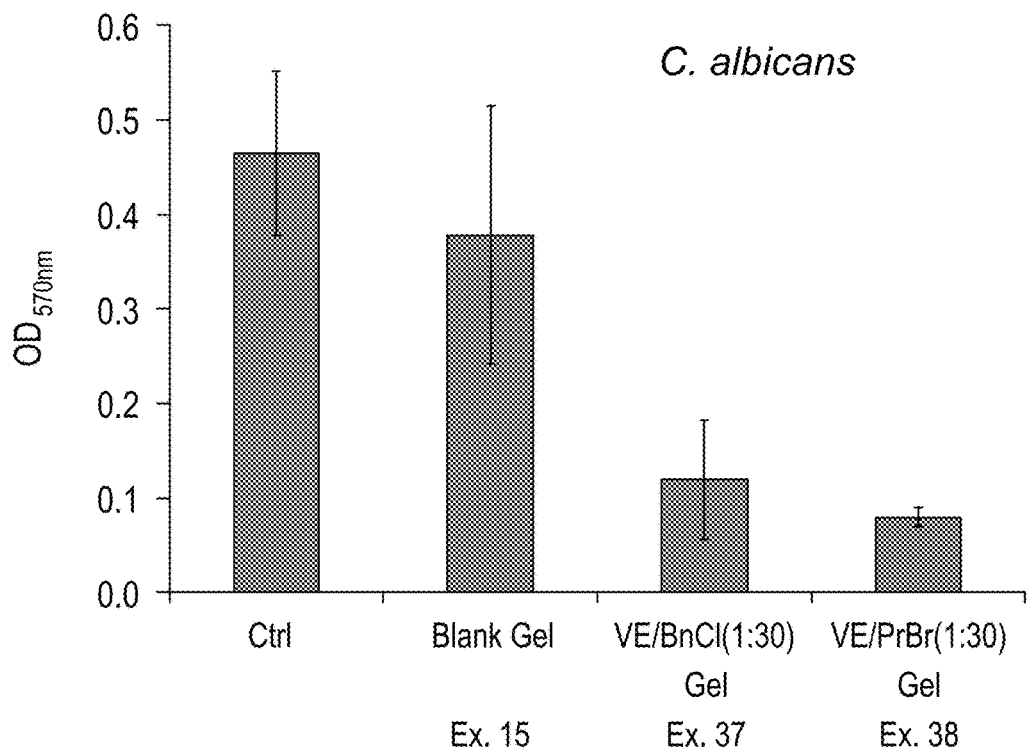
FIGS. 29A and 29B are bar graphs showing the reduction in metabolic activity and biomass, respectively, of *C. albicans* biofilms by:
  a) blank hydrogel Example 15 containing 4 wt. % VitE1.25-PEG(20k)-VitE1.25, b) cationic polymer loaded hydrogel Example 37 containing 4 wt. % VitE1.25-PEG(20k)-VitE1.25 and 0.0156 wt. % VE/BnCl (1:30), and
  c) cationic polymer loaded hydrogel Example 38 containing 4 wt. % VitE1.25-PEG(20k)-VitE1.25 and 0.0625 wt. % VE/PrBr(1:30). Cationic polymer VE/BnCl (1:30) and cationic polymer VE/PrBr(1:30) were loaded at minimum bactericidal concentrations (MBC) against *C. albicans* into VitE1.25-PEG(20k)-VitE1.25 (4 wt. %) hydrogels.
Figure 29B:
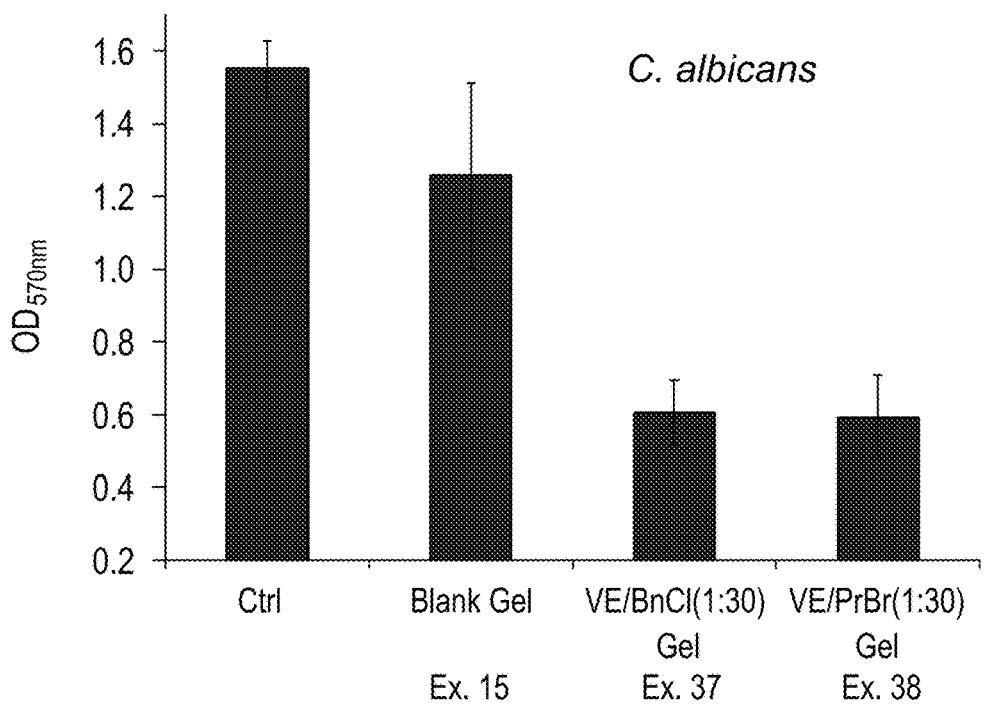

FIGS. 29A and 29B are bar graphs showing the reduction in metabolic activity and biomass, respectively, of C. albicans biofilms by blank hydrogel Example 15 (containing 4 wt. % VitE1.25-PEG(20k)-VitE1.25), cationic polymer loaded hydrogel Example 37 (containing 4 wt. % VitE1.25-PEG(20k)-VitE1.25 and 0.0156 wt. % VE/BnCl (1:30)), and cationic polymer loaded hydrogel Example 38 (containing 4 wt. % VitE1.25-PEG(20k)-VitE1.25 and 0.0625 wt. % VE/PrBr(1:30)). A reduction in metabolic activity (FIG. 29A and biomass (FIG. 29B) was obtained with cationic polymer loaded hydrogels against C. albicans.

It can seen that hydrogels loaded with VE/BnCl (1:30) were as efficient as those loaded with VE/PrBr(1:30) in reducing the proliferation and viability of *S. aureus* (Gram-positive) and *C. albicans* (fungus). The major difference was observed in *E. coli* (Gram-negative) where cell treated with hydrogels loaded with the more hydrophobic VE/BnCl (1:30) had significantly lower viability compared to those treated with VE/PrBr(1:30)-loaded hydrogels.

Figure 30:
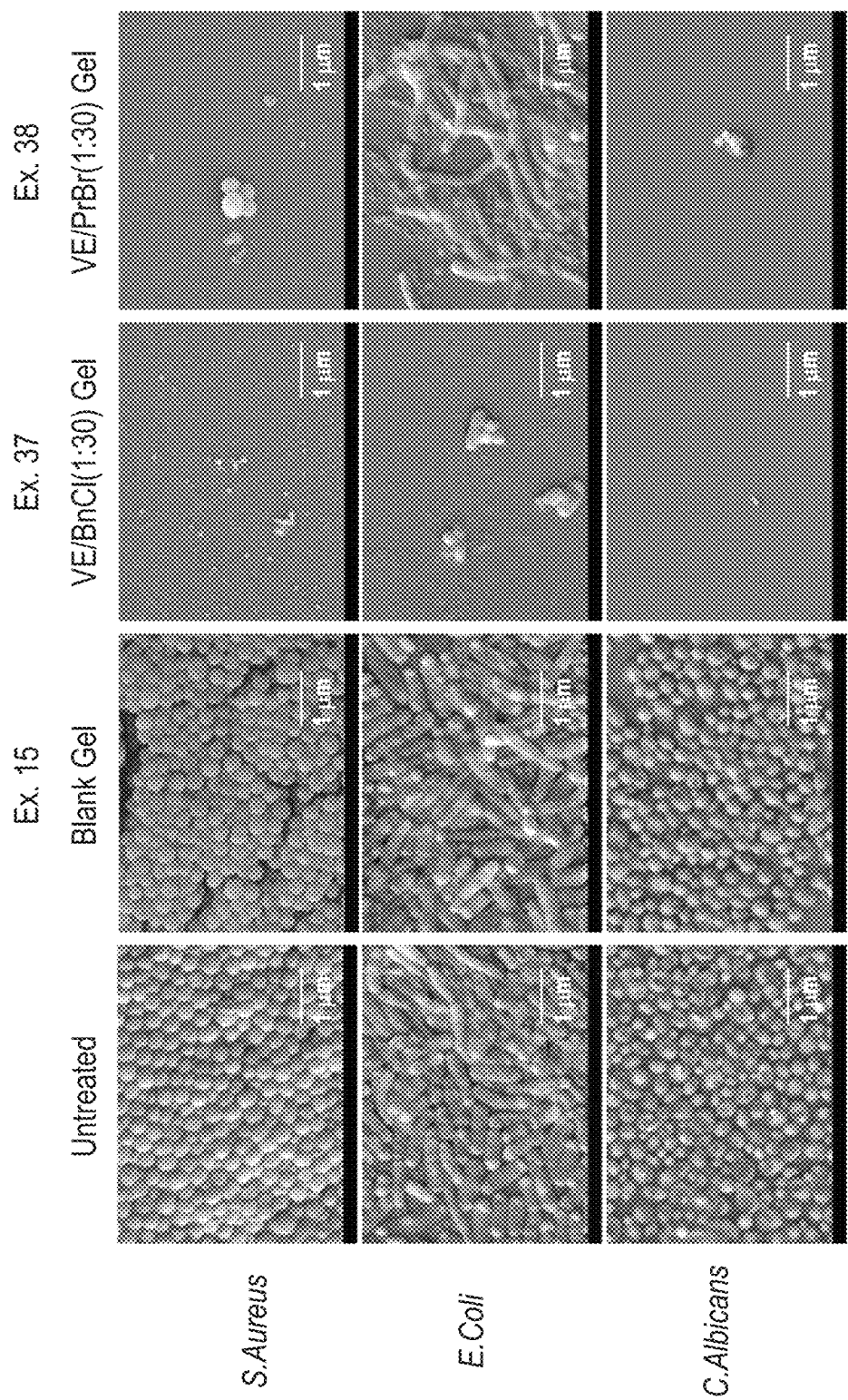
FIG. 30 is a series of SEM images of *S. aureus, E. coli*, and *C. albicans* biofilms after treatment with:
  a) blank hydrogel Example 15 containing 4 wt. % VitE1.25-PEG(20k)-VitE1.25,
  b) cationic polymer loaded hydrogel Example 37 containing 4 wt. % VitE1.25-PEG(20k)-VitE1.25 and 0.0156 wt. % VE/BnCl (1:30), and
  c) Example 38 containing 4 wt. % VitE1.25-PEG(20k)-VitE1.25 and 0.0625 wt. % VE/PrBr(1:30).

The persistence of microbial biomass after treatment was quantified using the crystal violet assay. Any portion of the biofilm that remains can act as a dormant zone harboring pockets of microbes that stay protected from antimicrobial agents. Furthermore, there can also be subpopulations of resistant cells referred to as 'persisters' that may reside in the residual biofilm. The ability of the cationic polymer loaded hydrogels to eradicate biomass followed a trend similar to the trend in reduction of cell viability of the microbes residing in the biofilms That is, VE/BnCl (1:30) had better antimicrobial action than VE/PrBr(1:30) against *E. coli*, and the two cationic polymers displayed similar efficiency against *S. aureus* and *C. albicans* biofilms SEM imaging demonstrates that biofilms treated with VE/BnCl (1:30)-loaded hydrogel (Example 37) showed extensive cell destruction and clearance (FIG. 30). Only ruptured cell fragments with the absence of intact cells remain for *S. aureus* and *C. albicans*. The images also correlate well to the quantification assays of cell viability and biomass where VE/BnCl (1:30) hydrogel is significantly more effective in eradicating *E. coli*, biofilm compared to the VE/PrBr(1:30) counterpart.

CONCLUSIONS

Biodegradable and biocompatible vitamin E-functionalized "ABA"-type triblock copolymers were formed by organocatalyzed ring opening of cyclic carbonate monomers bearing a covalently bound form of a vitamin E compound. The block copolymers form physically cross-linked hydrogels and organogels without the addition of reagents or chemical reactions. The rheological properties of the gels can be readily tunable in facile manner by varying the polymer concentration or composition. Gel stiffness, indicated by the storage modulus G', can vary from 1000 to 12000 Pa depending on the polymer composition and/or concentration. A wide array of pharmaceutical compounds, including small molecule drugs, biomolecules and cosmetics/dietary products can be loaded into the gels during the gel formation process. These gels function as depots for delivery of drugs having controlled release profiles. With the ease of formulation and tunability, these soft physical gels serve as an attractive candidate for an extensive range of pharmaceutical-driven applications.

As one example, a biocompatible and biodegradable herceptin loaded hydrogel prepared with VitE1.25-PEG (20k)-VitE1.25 was successfully employed as an injectable local delivery material for the antibody. Rheological properties and porosity of the loaded hydrogel can be adjusted by varying the polymer composition and polymer concentration. Histological examination reveals that the hydrogel does not induce chronic inflammatory response, and is able to degrade in vivo over time. The hydrogel matrix provides sustained release of herceptin, and localizes the antibody within the tumor site. In vivo anti-tumor efficacy is significantly enhanced using a single subcutaneous injection of herceptin-loaded hydrogel at a site close to the tumor as compared to herceptin solution. Herceptin-loaded hydrogel injected once at a distal site away from the tumor is comparable to that of weekly intravenous administration of herceptin solution over 4 weeks. Herceptin treatment using the hydrogel requires less frequent injections, thereby providing greater convenience and improved patient compliance. These results suggest that the vitamin E-functionalized hydrogels hold promise for subcutaneous delivery of antibodies.

The cationic polymer loaded hydrogels are able to eradicate the biomass and greatly reduce viability of microbes residing in biofilms. Taken together, the results suggest that the cationic polymer loaded hydrogels can be used to eliminate both planktonic and biofilm microbes.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A gel-forming block copolymer having a structure in accordance with formula (1):

wherein
d' is a positive number having a value of about 100 to about 600,
each K' is an independent divalent linking group selected from the group consisting of O, NH, S, and combinations thereof,
each $P^a$ is an independent monocarbonate or polycarbonate chain comprising 1 to about 10 vitamin-bearing subunits, wherein each of the vitamin-bearing subunits comprises a carbonate backbone portion and a side chain linked to the carbonate backbone portion, the side chain comprising a covalently bound form of a vitamin,
$Z^a$ is a first end group selected from the group consisting of hydrogen and groups comprising 1 to about 15 carbons, and
$Z^b$ is a second end group selected from the group consisting of hydrogen and groups comprising 1 to about 15 carbons.

2. The gel-forming block copolymer of claim 1, wherein each K' is O.

3. The gel-forming block copolymer of claim 1, wherein each K' is NH.

4. The gel-forming block copolymer of claim 1, wherein each K' is S.

5. The gel-forming block copolymer of claim 1, wherein each $P^a$ consists essentially of 1 to about 8 vitamin-bearing subunits.

6. The gel-forming block copolymer of claim 1, wherein the vitamin is selected from the group consisting of vitamin E compounds, vitamin D compounds, and combinations thereof.

7. The gel-forming block copolymer of claim 1, wherein each of the vitamin-bearing subunits comprises an alpha-tocopheryl moiety.

8. The gel-forming block copolymer of claim 1, wherein each of the vitamin-bearing subunits comprises an ergocalcipheryl moiety.

9. The gel-forming block copolymer of claim 1, wherein $Z^a$ is hydrogen and $Z^b$ is hydrogen.

10. The gel-forming block copolymer of claim 1, wherein the vitamin-bearing subunits of the gel-forming block copolymer have the structure:

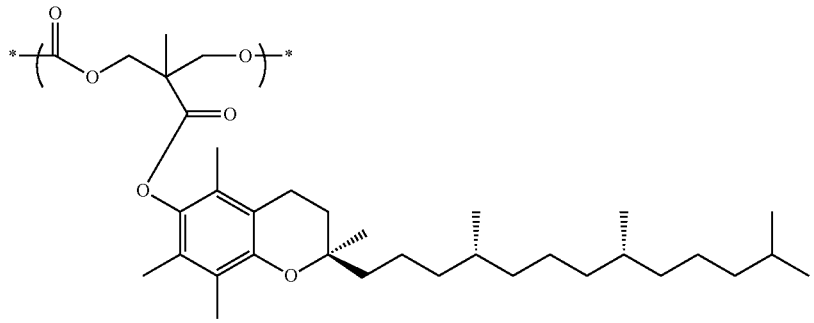

11. The gel-forming block copolymer of claim 1, wherein the vitamin-bearing subunits of the gel-forming block copolymer have the structure:

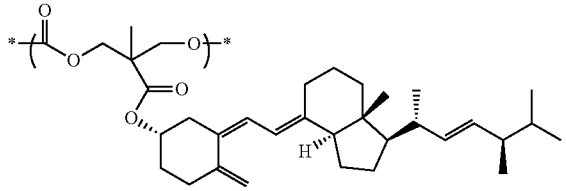

12. The gel-forming block copolymer of claim 1, wherein the gel-forming block copolymer has a structure according to formula (1-A):

wherein
the carbonate backbone atoms are numbered 1 to 6 in each carbonate subunit,
d' is a positive number having a value of about 100 to about 600,
each m' is an independent positive number having a value of 2 to about 20,
each $L^d$ is independently a single bond or a divalent linking group comprising 1 to about 15 carbons,
each V is an independent moiety comprising a covalently bound form of a vitamin,
each R' is an independent monovalent radical selected from the group consisting of hydrogen, halogens, methyl, and ethyl,
each R" is an independent monovalent radical selected from the group consisting of hydrogen and alkyl groups comprising 1 to 6 carbons,
each t is an independent positive integer having a value of 0 to 2,
each t' is an independent positive integer having a value of 0 to 2,
no carbonate subunit has t=0 and t'=0,
$Z^a$ is a first end group selected from the group consisting of hydrogen and groups comprising 1 to about 15 carbons, and
$Z^b$ is a second end group selected from the group consisting of hydrogen and groups comprising 1 to about 15 carbons.

13. The gel-forming block copolymer of claim 12, wherein $Z^a$ is hydrogen and $Z^b$ is hydrogen.

14. The gel-forming block copolymer of claim 12, wherein each t is 1 and each t' is 1.

15. The gel-forming block copolymer of claim 12, wherein each R' is hydrogen.

16. The gel-forming block copolymer of claim 12, wherein each t is 1, each t' is 1, and each R' is hydrogen.

17. The gel-forming block copolymer of claim 1, wherein the gel-forming block copolymer has a structure according to formula (1-B):

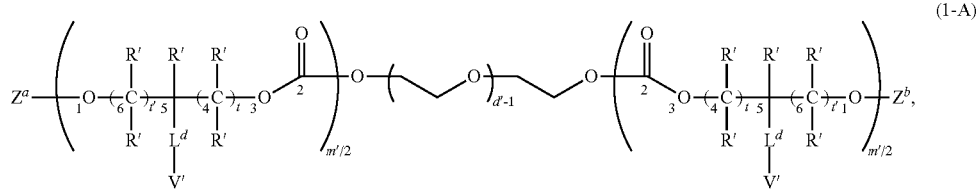

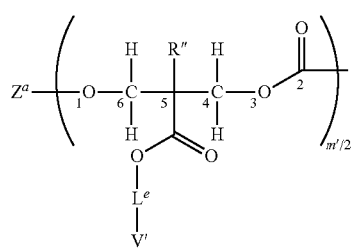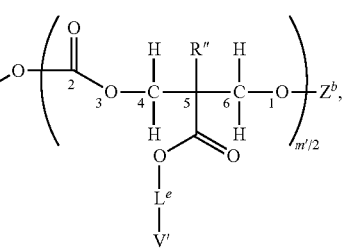 (1-B)

wherein
- the carbonate backbone atoms are numbered 1 to 6 in each carbonate subunit,
- d' is a positive number having a value of about 100 to about 600,
- each m' is an independent positive number having a value of 2 to about 20,
- each $L^e$ is independently a single bond or a divalent linking group comprising 1 to about 15 carbons,
- each V' is an independent moiety comprising a covalently bound form of a vitamin,
- each R' is an independent monovalent radical selected from the group consisting of hydrogen, halogens, methyl, and ethyl,
- each R" is an independent monovalent radical selected from the group consisting of hydrogen and alkyl groups comprising 1 to 6 carbons,
- $Z^a$ is a first end group selected from the group consisting of hydrogen and groups comprising 1 to about 15 carbons, and
- $Z^b$ is a second end group selected from the group consisting of hydrogen and groups comprising 1 to about 15 carbons.

18. The gel-forming block copolymer of claim 17, wherein $Z^a$ is hydrogen and $Z^b$ is hydrogen.

19. The gel-forming block copolymer of claim 17, wherein R" is methyl.

20. The gel-forming block copolymer of claim 17, wherein R" is ethyl.

* * * * *